United States Patent
Park et al.

(10) Patent No.: US 10,074,811 B2
(45) Date of Patent: Sep. 11, 2018

(54) COMPOUND AND ORGANIC LIGHT EMITTING DEVICE COMPRISING SAME

(71) Applicant: SAMSUNG DISPLAY CO., LTD., Yongin-si, Gyeonggi-do (KR)

(72) Inventors: Junha Park, Yongin-si (KR); Youngkook Kim, Yingin-si (KR); Munki Sim, Yongin-si (KR); Eunyoung Lee, Yongin-si (KR); Hyoyoung Lee, Yongin-si (KR); Eunjae Jeong, Yongin-si (KR); Seokhwan Hwang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 59 days.

(21) Appl. No.: 15/178,338

(22) Filed: Jun. 9, 2016

(65) Prior Publication Data

US 2017/0125696 A1   May 4, 2017

(30) Foreign Application Priority Data

Nov. 4, 2015   (KR) .......................... 10-2015-0154759

(51) Int. Cl.
| H01L 51/00 | (2006.01) |
| C07D 471/04 | (2006.01) |
| C07D 471/14 | (2006.01) |
| H01L 27/32 | (2006.01) |
| H01L 51/50 | (2006.01) |

(52) U.S. Cl.
CPC ........ *H01L 51/0072* (2013.01); *C07D 471/04* (2013.01); *C07D 471/14* (2013.01); *H01L 27/3248* (2013.01); *H01L 51/005* (2013.01); *H01L 51/0052* (2013.01); *H01L 51/0058* (2013.01); *H01L 51/0067* (2013.01); *H01L 51/0073* (2013.01); *H01L 51/0077* (2013.01); *H01L 51/006* (2013.01); *H01L 51/0054* (2013.01); *H01L 51/0061* (2013.01); *H01L 51/0085* (2013.01); *H01L 51/506* (2013.01); *H01L 51/5072* (2013.01)

(58) Field of Classification Search
CPC ............... H01L 51/006; H01L 51/0061; H01L 51/0067; H01L 51/0072
See application file for complete search history.

(56) References Cited

U.S. PATENT DOCUMENTS

| 5,645,948 A | 7/1997 | Shi et al. |
| 2004/0053069 A1 | 3/2004 | Sotoyama et al. |
| 2013/0112920 A1 | 5/2013 | Stoessel et al. |
| 2013/0207048 A1 | 8/2013 | Schwaiger et al. |
| 2014/0103325 A1 | 4/2014 | Shin et al. |
| 2014/0167028 A1* | 6/2014 | Sekiguchi ............ C07D 487/06 257/40 |
| 2014/0183466 A1* | 7/2014 | Lee ....................... H01L 51/006 257/40 |

FOREIGN PATENT DOCUMENTS

| EP | 3214085 A2 * | 9/2017 |
| JP | 10-17860 A | 1/1998 |
| JP | 11-87067 A | 3/1999 |
| JP | 4060669 B2 | 3/2008 |
| JP | 2012-0138672 | 6/2012 |
| KR | 10-0525408 B1 | 11/2005 |
| KR | 10-2012-0061056 A | 6/2012 |
| KR | 10-2013-0139988 A | 12/2013 |
| WO | WO 2012/007086 A1 | 1/2012 |
| WO | WO 2016/068640 A2 | 5/2016 |

OTHER PUBLICATIONS

Partial English translation of relevant parts of WO 2016/068640 A2 dated May 6, 2016, listed above (1 page).
Pandey et al., "Synthesis of Biologically Active Pyridoimidazole/Imidazobenzothiazole Annulated Polyheterocycles Using Cyanuric Chloride in Water," Royal Society of Chemistry Advances, 2014, vol. 4, pp. 26757-26770, DOI: 10.1039/c4ra03415e.
Fan et al., "One-pot Sequential Reactions Featuring a Copper-catalyzed Amination Leading to Pyrido[2',1':2,3]imidazo[4,5-c]quinolines and Dihydropyrido[2',1':2,3]imidazo[4,5-c]quinolines," Chemistry: An Asian Journal, 2015, vol. 10, pp. 1281-1285, DOI: 10.1002/asia.201500266.
EPO Extended Search Report dated Sep. 9, 2016, for corresponding European Patent Application No. 16181518.8 (9 pages).
Adachi, C. et al., Confinement of charge carries and molecular excitons within 5nmthick emitter layer in organic electroluminescent devices with a double heterostructure, Applied Physics Letters, 1990, pp. 531-533, vol. 57, No. 6, AIP Publishing LLC.

(Continued)

*Primary Examiner* — Melissa A Rioja
(74) *Attorney, Agent, or Firm* — Lewis Roca Rothgerber Christie LLP

(57) ABSTRACT

An organic light-emitting device including a first electrode; a second electrode facing the first electrode; and an organic layer that is between the first electrode and the second electrode and includes an emission layer, wherein the organic layer includes a compound represented by Formula 1:

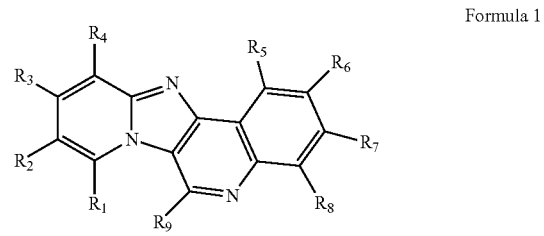

Formula 1

When compounds represented by Formula 1 are used as an electron transport material, excellent I-V-L characteristics may be obtained.

18 Claims, 1 Drawing Sheet

(56) References Cited

OTHER PUBLICATIONS

Johansson, N. et al., Solid-State Amplified Spontaneous Emission in Some Spiro-Type Molecules: A New Concept for the Design of Solid-State Lasing Molecules, Advanced Materials, 1998, pp. 1136-1141, vol. 10, No. 14, Wiley-VCH Verlag GmbH, Weinheim, Germany.
Sakamoto, Y. et al., Synthesis, Characterization, and Electron-Transport Property of Perfluorinated Phenylene Dendrimers, Journal of the American Chemical Society, 2000, pp. 1832-1833, vol. 122, No. 8, American Chemical Society.
Tang, C.W. et al., Organic electroluminescent diodes, Applied Physics Letters, 1987, pp. 913-915, vol. 51, No. 12, AIP Publishing LLC.
Tao, Y.T. et al., Sharp green electroluminescence from 1H-pyrazolo[3,4-b]quinoline-based light-emitting diodes, Applied Physics Letters, 2000, pp. 1575-1577, vol. 77, No. 11, American Institute of Physics.
Yamaguchi, S. et al., Diphenylamino-Substituted 2,5-Diarylsiloles for Single-Layer Organic Electroluminescent Devices, Chemistry Letters, 2001, pp. 98-99, The Chemical Society of Japan.

\* cited by examiner

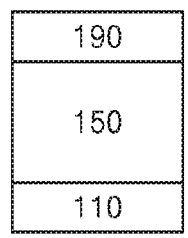

COMPOUND AND ORGANIC LIGHT EMITTING DEVICE COMPRISING SAME

CROSS-REFERENCE TO RELATED APPLICATION

This application claims priority to and the benefit of Korean Patent Application No. 10-2015-0154759, filed on Nov. 4, 2015 in the Korean Intellectual Property Office, the entire content of which is incorporated herein by reference.

BACKGROUND

1. Field

One or more aspects of example embodiments of the present disclosure are related to a compound and an organic light-emitting device including the same.

2. Description of the Related Art

Organic light-emitting devices are self-emission devices that have wide viewing angles, high contrast ratios, short response times, and/or excellent brightness, driving voltage, and/or response speed characteristics, and may produce full-color images.

An example organic light-emitting device may include a first electrode on a substrate, and a hole transport region, an emission layer, an electron transport region, and a second electrode sequentially positioned on the first electrode. Holes provided from the first electrode may move toward the emission layer through the hole transport region, and electrons provided from the second electrode may move toward the emission layer through the electron transport region. Carriers (such as holes and electrons) may recombine in the emission layer to produce excitons. These excitons may transition (e.g., radiatively decay) from an excited state to the ground state to thereby generate light.

SUMMARY

One or more aspects of example embodiments of the present disclosure are directed toward a compound having excellent electron transport capability and/or material stability that is accordingly suitable for use as an electron transport material, and an organic light-emitting device including the compound, having high efficiency, low voltage, high luminance, and/or a long lifespan.

Additional aspects will be set forth, in part, in the description that follows and, in part, will be apparent from the description, or may be learned by practice of the presented embodiments.

One or more example embodiments of the present disclosure provide a compound represented by Formula 1:

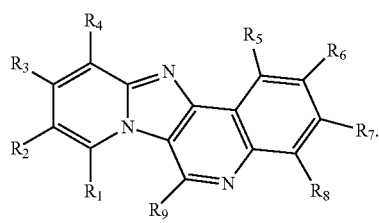

Formula 1

In Formula 1, $R_1$ to $R_9$ may each independently be selected from hydrogen, deuterium, a halogen atom, a nitro group, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group; and at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from the group consisting of:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$);

wherein $Q_{11}$ to $Q_{17}$ and $Q_{21}$ to $Q_{27}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to one or more example embodiments of the present disclosure, an organic light-emitting device includes: a first electrode; a second electrode facing the first electrode; and an organic layer that is between the first electrode and the second electrode and includes an emission layer, wherein the organic layer includes the compound described above.

According to one or more example embodiments of the present disclosure, a flat panel display apparatus includes the organic light-emitting device, wherein the first electrode of the organic light-emitting device may be electrically connected to a source electrode or a drain electrode of a thin film transistor.

BRIEF DESCRIPTION OF THE DRAWING

These and/or other aspects will become apparent and more readily appreciated from the following description of the embodiments, taken in conjunction with the drawing, which is a schematic view of an organic light-emitting device according to an embodiment of the present disclosure.

DETAILED DESCRIPTION

Reference will now be made in more detail to embodiments, examples of which are illustrated in the accompanying drawings, wherein like reference numerals refer to like elements throughout and duplicative descriptions thereof may not be provided. In this regard, the present embodiments may have different forms and should not be construed as being limited to the descriptions set forth herein. Accordingly, the embodiments are merely described below, by referring to the drawing, to explain aspects of the present description. As used herein, the term "and/or" includes any and all combinations of one or more of the associated listed items. Expressions such as "at least one of", "one of", and "selected from", when preceding a list of elements, modify the entire list of elements and do not modify the individual elements of the list.

In the drawings, the thicknesses of layers, films, panels, regions, etc., may be exaggerated for clarity. It will be understood that when an element such as a layer, film, region, or substrate is referred to as being "on" another element, it can be directly on the other element or intervening element(s) may also be present. In contrast, when an element is referred to as being "directly on" another element, no intervening elements are present.

A compound according to an embodiment of the present disclosure may be represented by Formula 1:

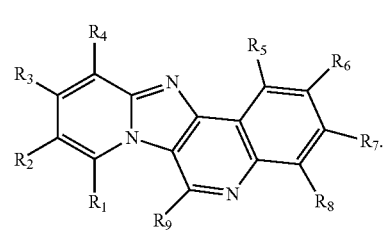

Formula 1

In Formula 1, $R_1$ to $R_9$ may each independently be selected from hydrogen, deuterium, a halogen atom, a nitro group, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from the group consisting of:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group(aryloxy), $C_6$-$C_{60}$ arylthio group(arylthio), $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$);

wherein $Q_{11}$ to $Q_{17}$ and $Q_{21}$ to $Q_{27}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

Organic single molecule materials selected from organometallic complexes may be suitable for use as electron transport materials due to their stability with respect to electrons, and their suitable or favorable electron mobility characteristics.

Among the electron transport materials available in the related art, Alq3 has the highest (e.g., high) stability and the highest (e.g., high) electron affinity. When Alq3 is used in a blue light-emitting device, however, the color purity of the device may deteriorate due to exciton diffusion-derived emission.

A Flavon (e.g., flavone) derivative and a germanium and/or silicon chloropentadiene derivative are also well known in the related art. Non-limiting examples of the organic single molecule material may include a 2-biphenyl-4-yl-5-(4-t-butylphenyl)-1,3,4-oxadiazole (PBD) derivative linked (e.g., coupled) to a spiro compound, and 2,2',2''-(benzene-1,3,5-triyl)-tris(1-phenyl-1H-benzimidazole) (TPBI), each having a hole blocking capability and an excellent electron transport capability. For example, a benzimidazole derivative is widely known as having excellent durability.

However, an organic light-emitting device with an electron transport layer including this material may exhibit a short emission lifespan, low preservative durability, and/or low reliability. This may be due to physical and/or chemical changes in the organic material, photochemical and/or electrochemical changes in the organic material, oxidation of the cathode, exfoliation, and/or a lack of durability.

Accordingly, aspects of embodiments of the present disclosure provide a compound having a novel structure, and an organic light-emitting device including the compound. The compound having a novel structure according to an embodiment of the present disclosure may have excellent electric characteristics, a high charge transport capability, a high glass transition temperature, and/or favorable anti-crystallization characteristics, and may be suitably used as an electron transport material in a red, green, blue, and/or white fluorescent and/or phosphorescent device. When the compound is used in manufacturing an organic light-emitting device, the manufactured organic light-emitting device may have high efficiency, low voltage, high brightness, and/or a long lifespan.

The compound represented by Formula 1 according to an embodiment of the present disclosure may be suitable for use as an electron transport material and/or an electron injection material for an organic light-emitting device. In Formula 1, pyrido[2',1':2,3]imidazo[4,5-c]quinoline has a heterocyclic structure, which is strong and may have high thermal stability. When a substituent is coupled to pyrido[2',1':2,3]imidazo[4,5-c]quinoline, the planarity of the molecule is maintained, enabling an electron donating capability, and thus, electronic interaction. When a substituent is linked (e.g., coupled) to a benzene ring of pyrido[2',1':2,3]imidazo[4,5-c]quinoline, the symmetry of a molecular structure may be reduced, leading to a high degree of amorphousness. Accordingly, high stability may be obtained when a thin film is formed in the device manufacturing process.

In some embodiments, $R_1$ to $R_9$ in Formula 1 may each independently be selected from hydrogen, deuterium, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, $R_1$, $R_3$, $R_4$, $R_5$, $R_7$, and $R_8$ in Formula 1 may each independently be selected from hydrogen and deuterium.

In some embodiments, $R_2$ and $R_9$ in Formula 1 may each independently be represented by one selected from Formulae 2a to 2e:

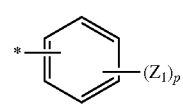

2a

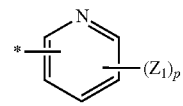

2b

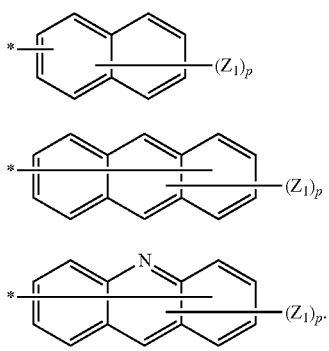

$Z_1$ may be selected from hydrogen, deuterium, a halogen atom, a cyano group, a nitro group, a hydroxyl group, a carboxyl group, a substituted or unsubstituted $C_1$ to $C_{20}$ alkyl group, a substituted or unsubstituted $C_6$ to $C_{20}$ aryl group, a substituted or unsubstituted $C_1$ to $C_{20}$ heteroaryl group, a substituted or unsubstituted monovalent non-aromatic condensed polycyclic group, and a substituted or unsubstituted monovalent non-aromatic condensed heteropolycyclic group;

when $Z_1$ is two or more, the plurality of $Z_1$ groups may be identical to or different from each other;

p may be an integer selected from 1 to 9; and

* may indicate a binding site.

In some embodiments, $R_6$ in Formula 1 may be represented by one selected from Formulae 3a to 3g:

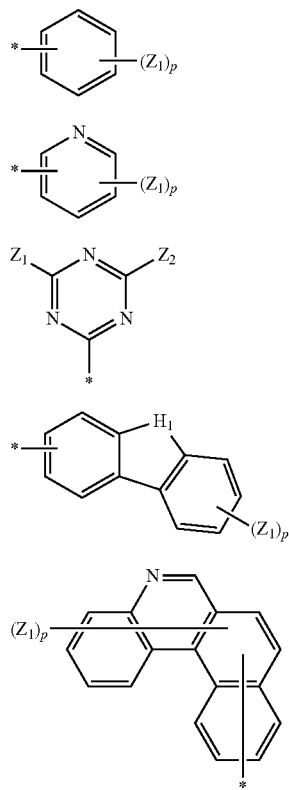

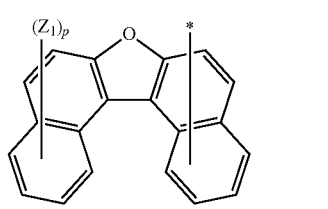

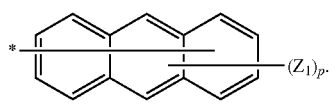

In Formulae 3a to 3g, $H_1$ may be selected from $CR_{11}R_{12}$, $NR_{13}$, O, and S, $R_{11}$ to $R_{13}$, $Z_1$, and $Z_2$ may each independently be selected from hydrogen, deuterium, a halogen atom, a cyano group, a nitro group, a hydroxyl group, a carboxyl group, a substituted or unsubstituted $C_1$ to $C_{20}$ alkyl group, a substituted or unsubstituted $C_6$ to $C_{20}$ aryl group, a substituted or unsubstituted $C_1$ to $C_{20}$ heteroaryl group, a substituted or unsubstituted monovalent non-aromatic condensed polycyclic group, and a substituted or unsubstituted monovalent non-aromatic condensed heteropolycyclic group;

when the number of $Z_1$ groups is two or more, the plurality of $Z_1$ groups may be identical to or different from each other;

p may be an integer selected from 1 to 9; and

* may indicate a binding site.

In some embodiments, the compound represented by Formula 1 may be represented by Formula 2:

Formula 2

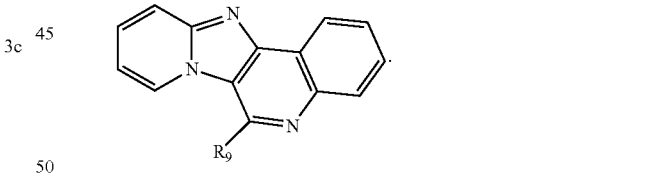

In some embodiments, the compound represented by Formula 1 may be represented by Formula 3:

Formula 3

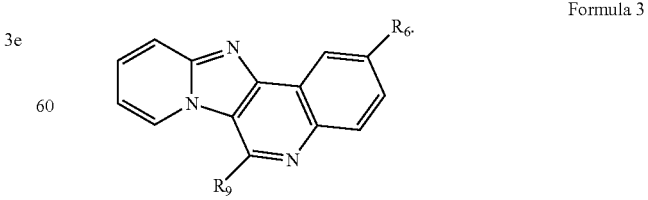

In some embodiments, the compound represented by Formula 1 may be represented by Formula 4:

Formula 4
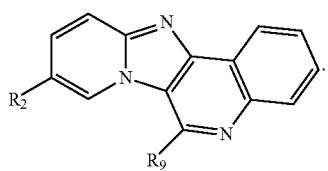
In some embodiments, the compound represented by Formula 1 may be represented by one selected from Compounds 1 to 90, but embodiments of the present disclosure are not limited thereto:
1
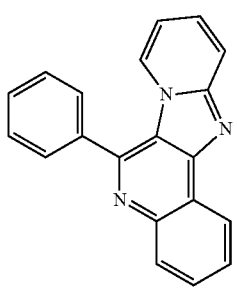
2
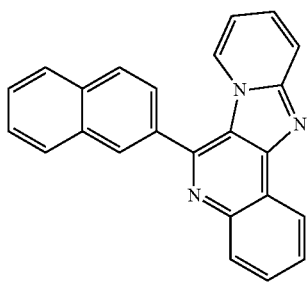
3
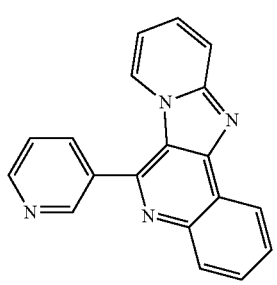
4
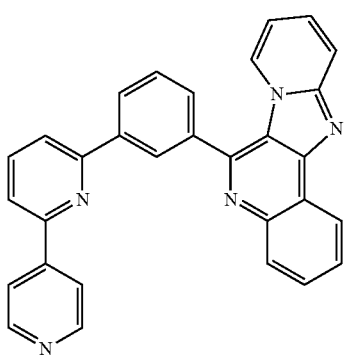
-continued
5
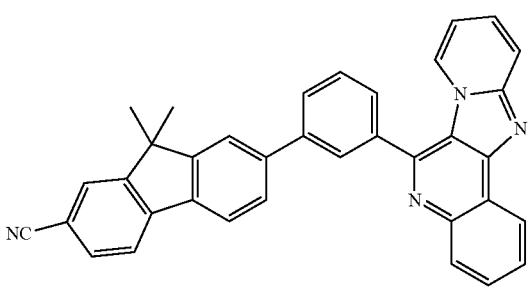
6
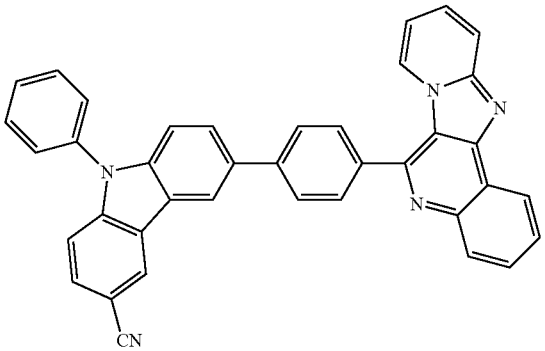
7
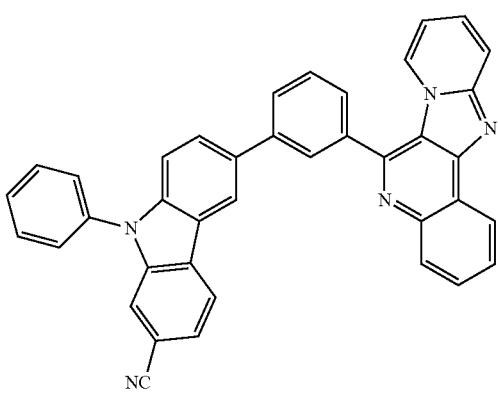
8
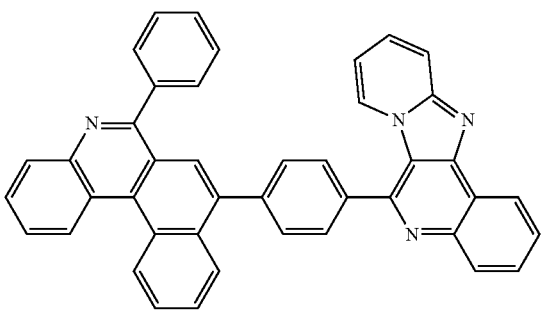

9
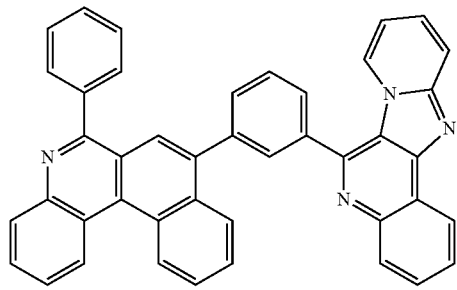
10
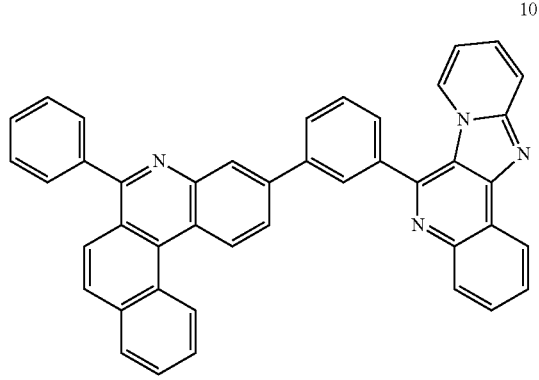
11
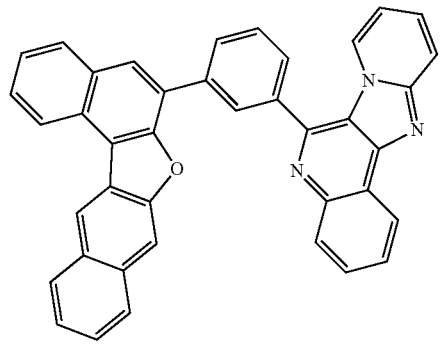
12
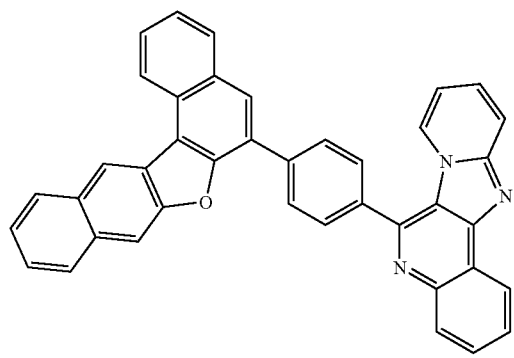
13
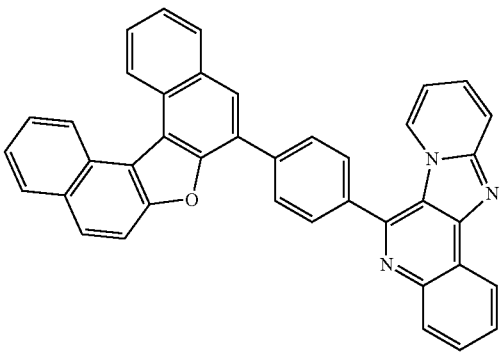
14
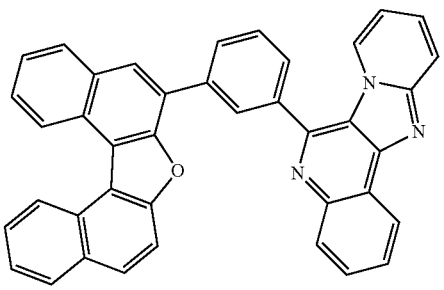
15
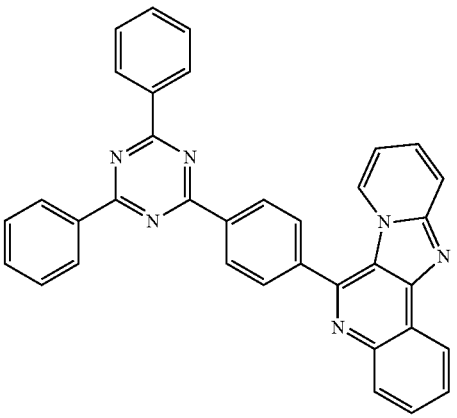
16
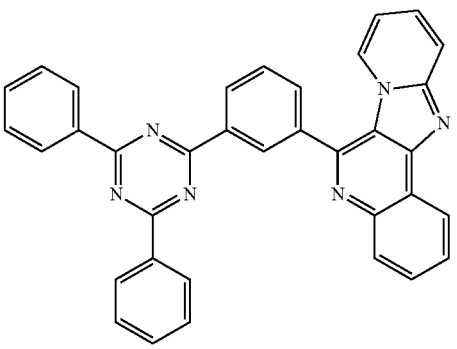

17
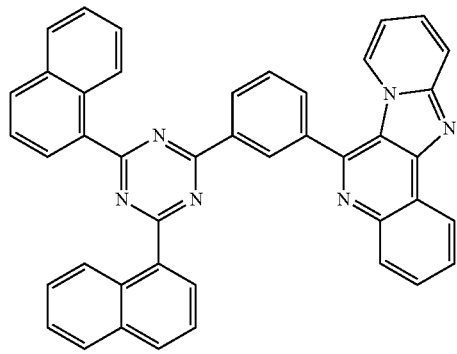
18
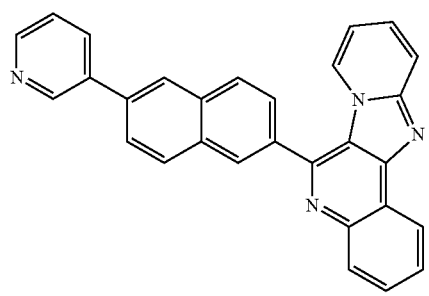
19
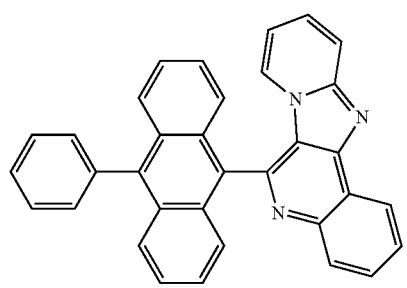
20
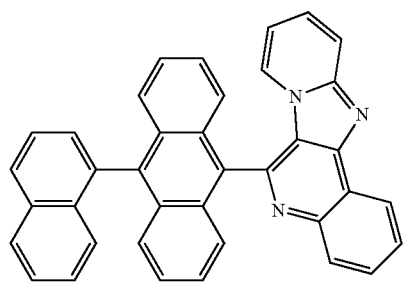
21
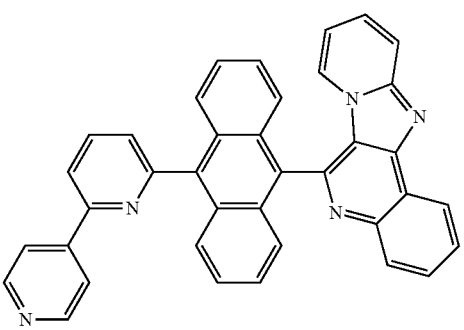
22
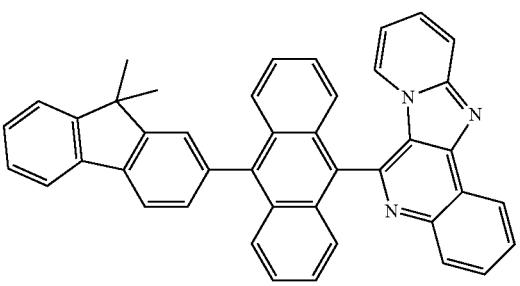
23
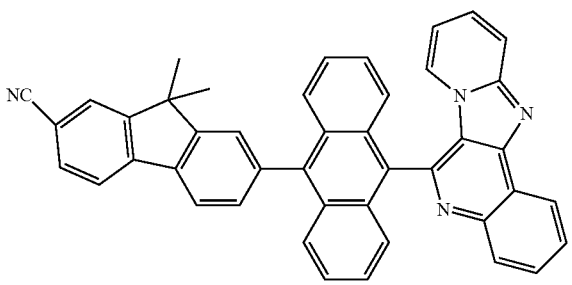
24
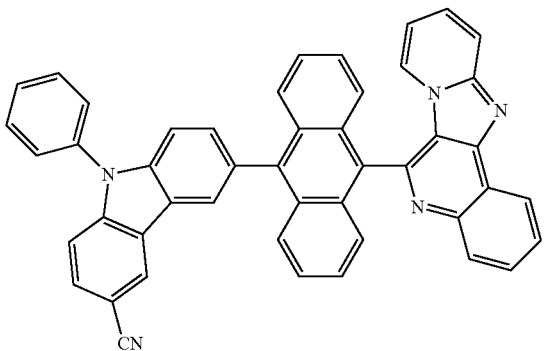
25

26
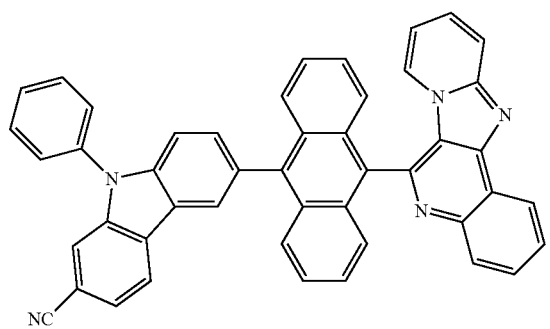
27
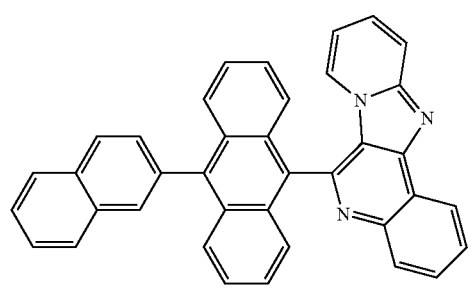
28
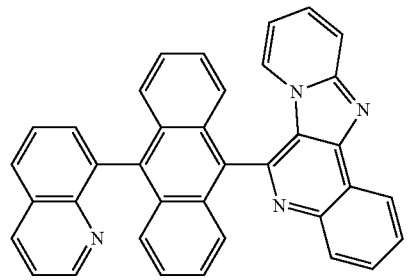
29
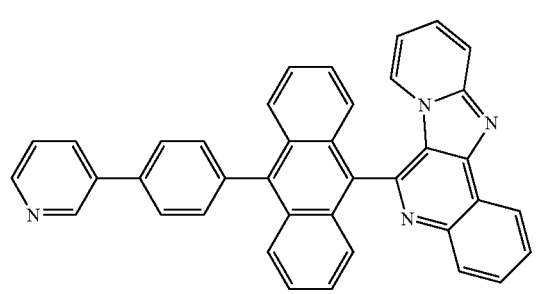
30
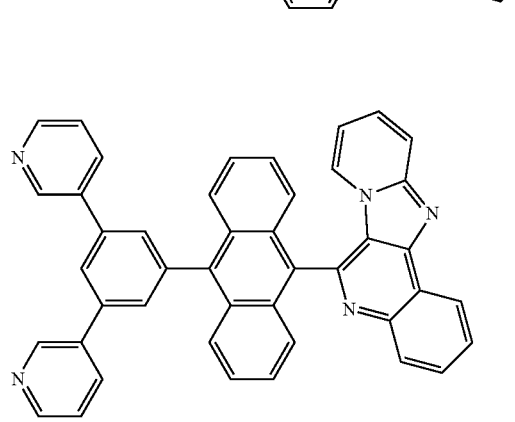
31
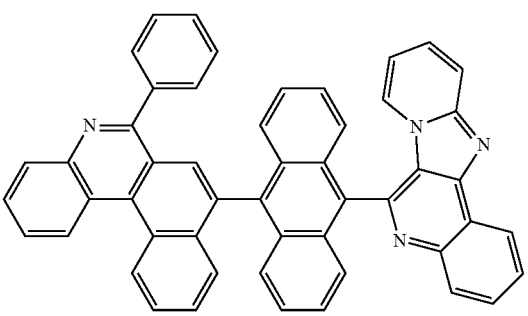
32
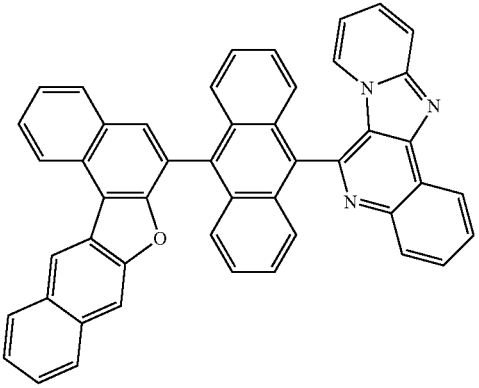
33
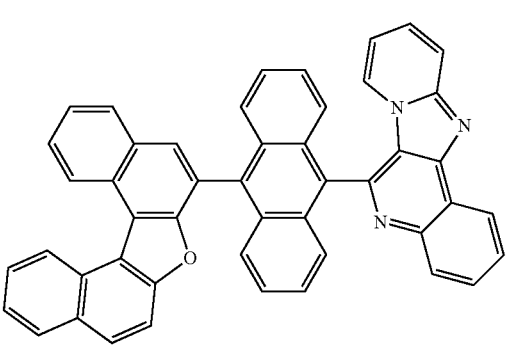
34
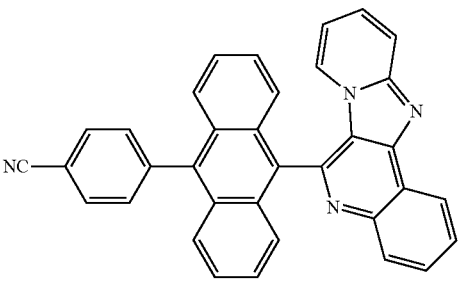
35
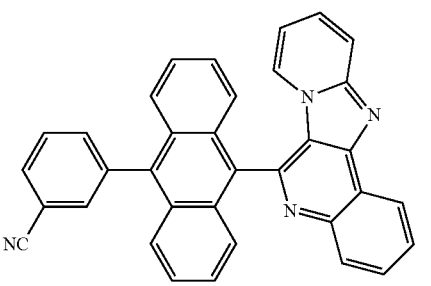

36
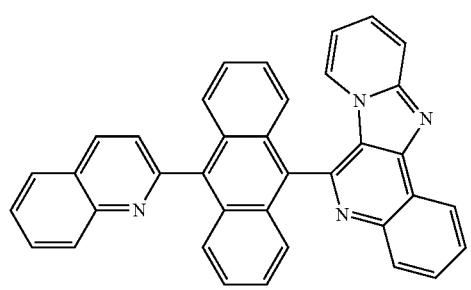
37
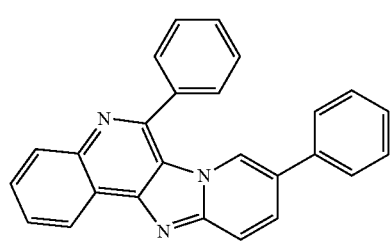
38
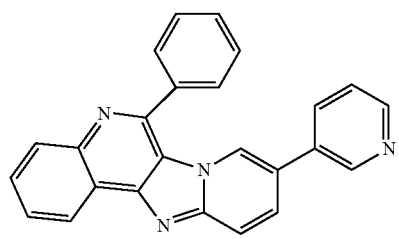
39
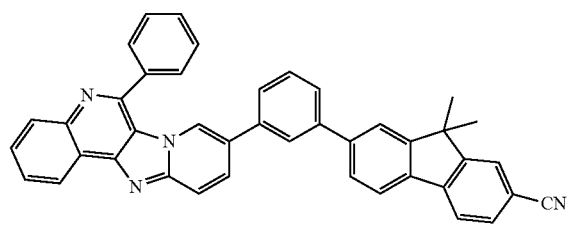
40
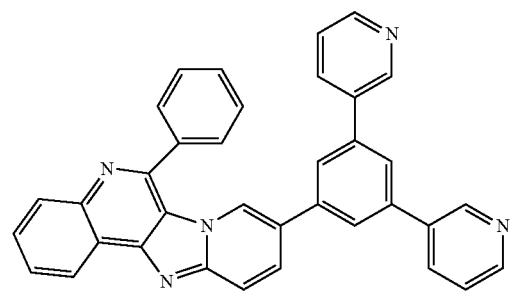
41
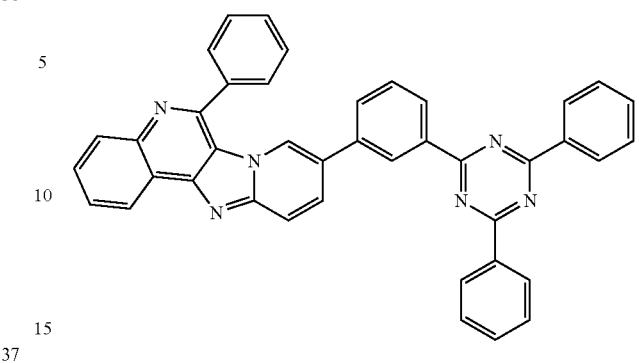
42
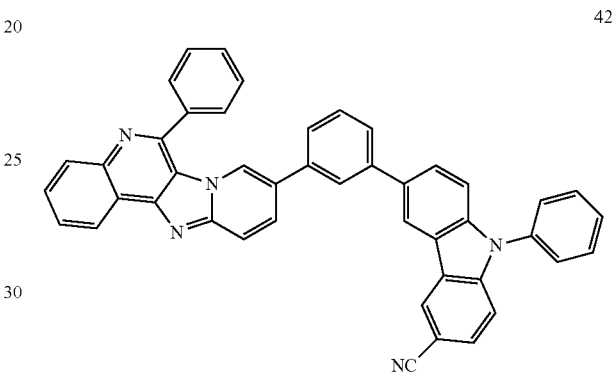
43
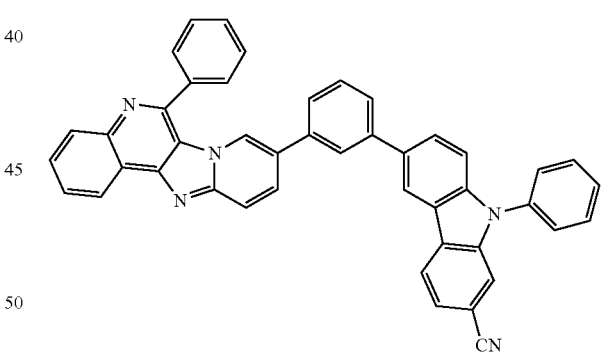
44
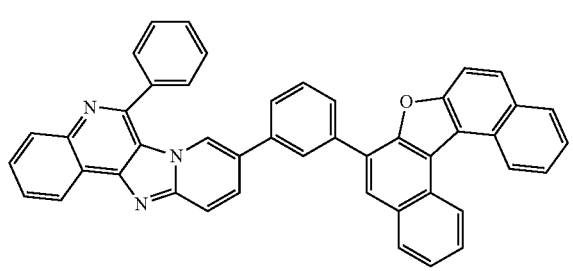

45
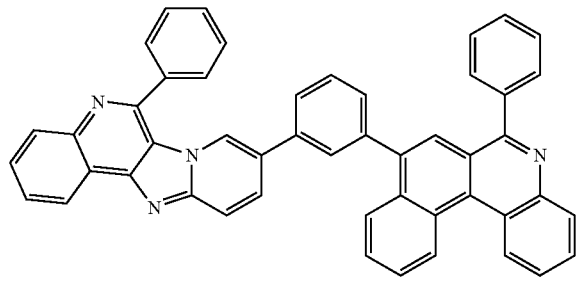
46
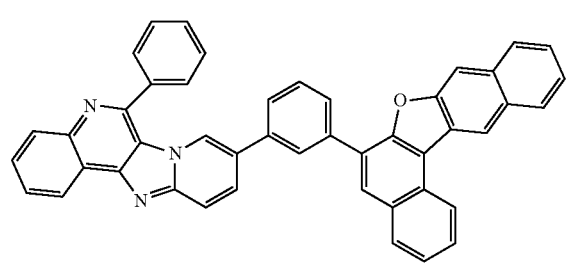
47
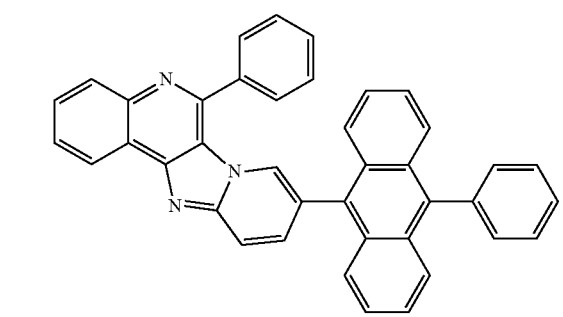
48
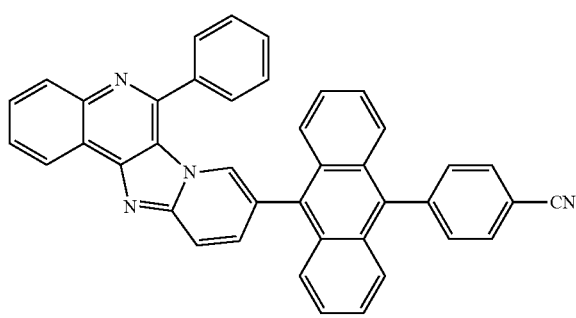
49
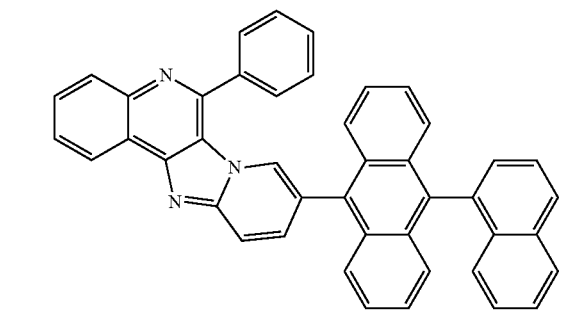
50
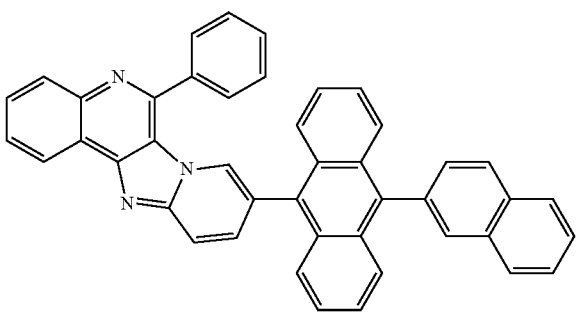
51
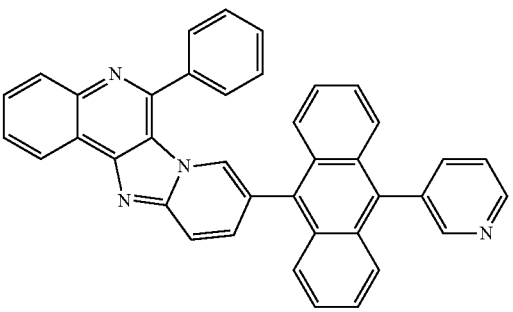
52
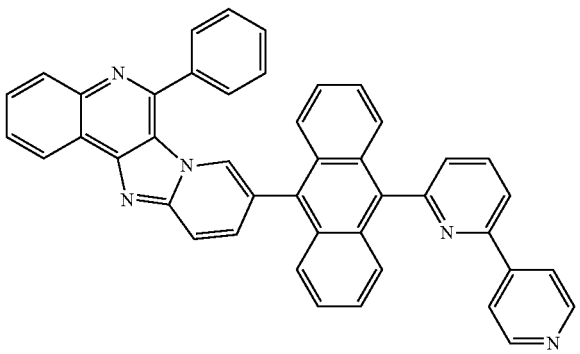
53
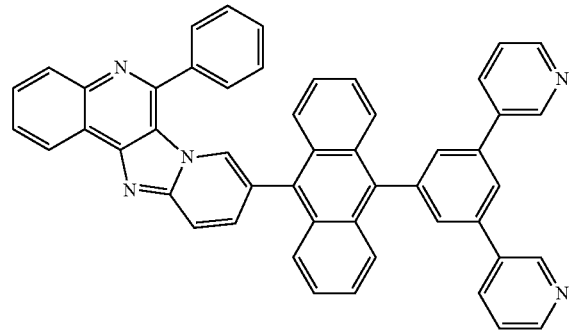

21
-continued
54
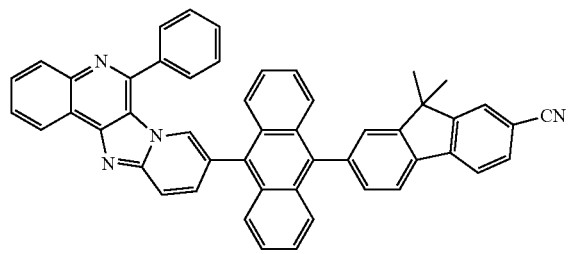
55
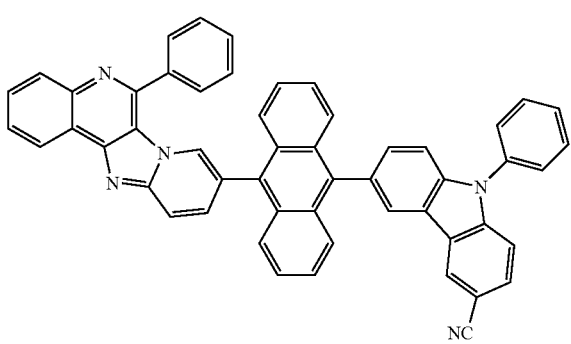
56
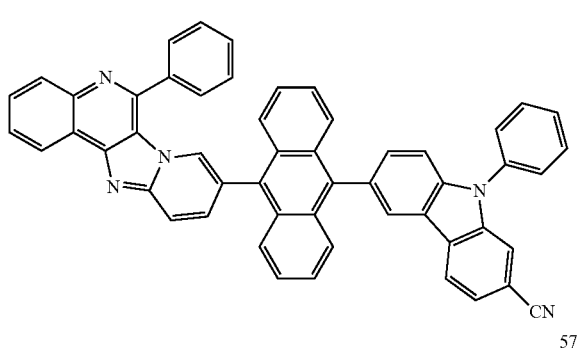
57
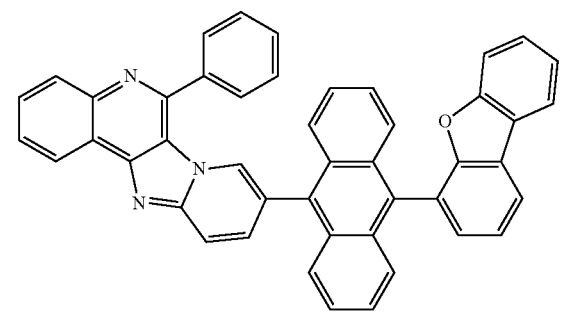
58
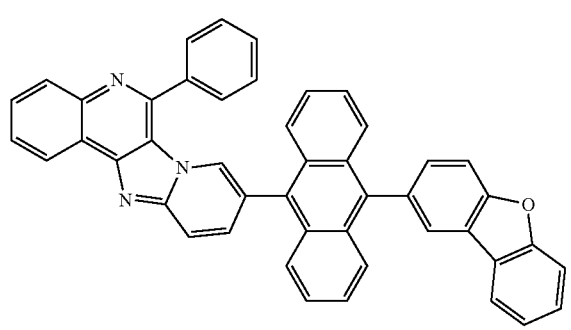
22
-continued
59
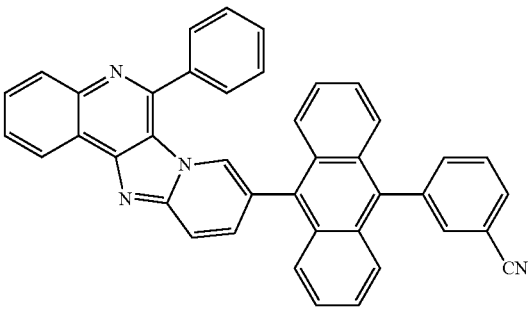
60
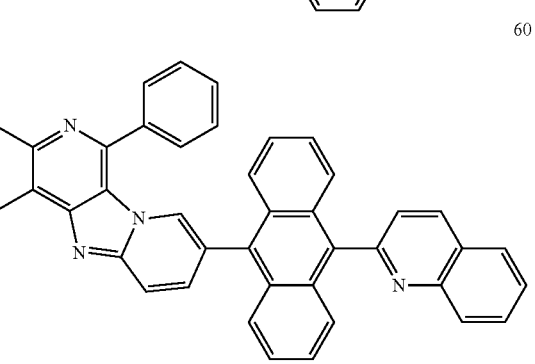
61
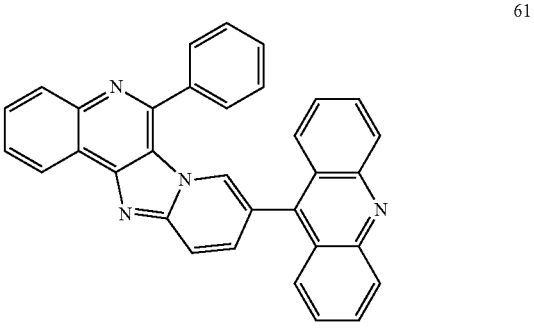
62
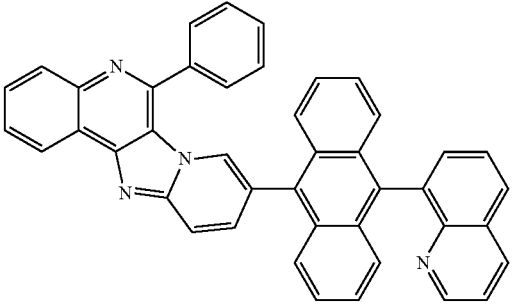
63
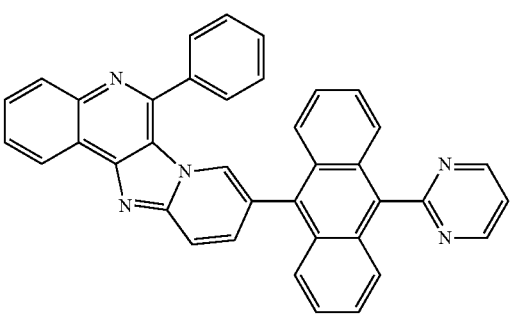

-continued
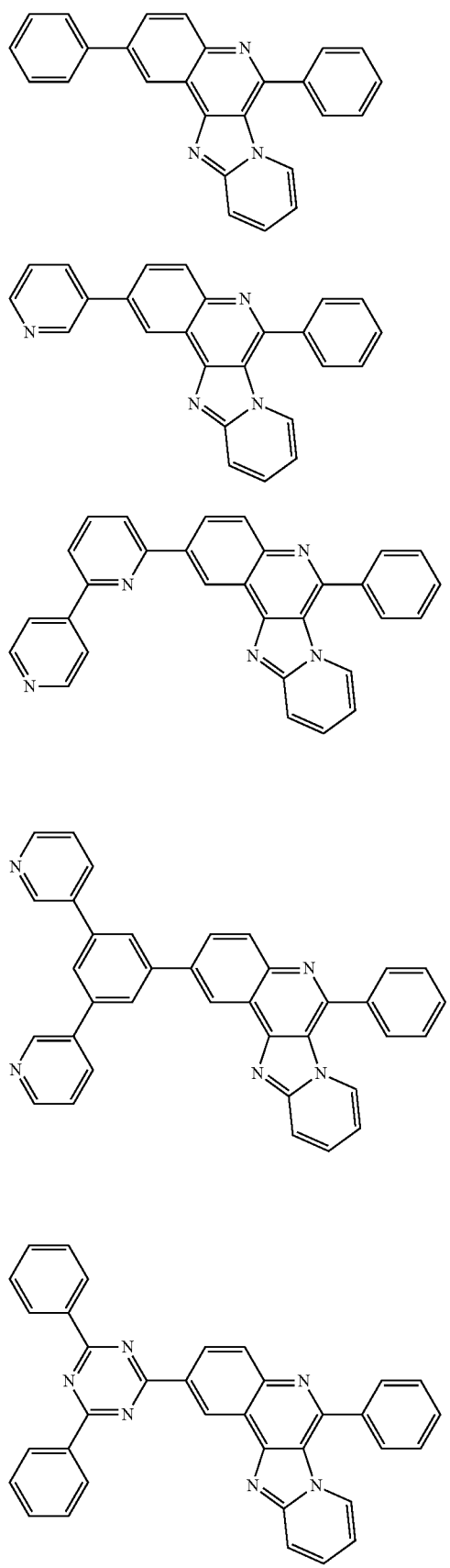
-continued
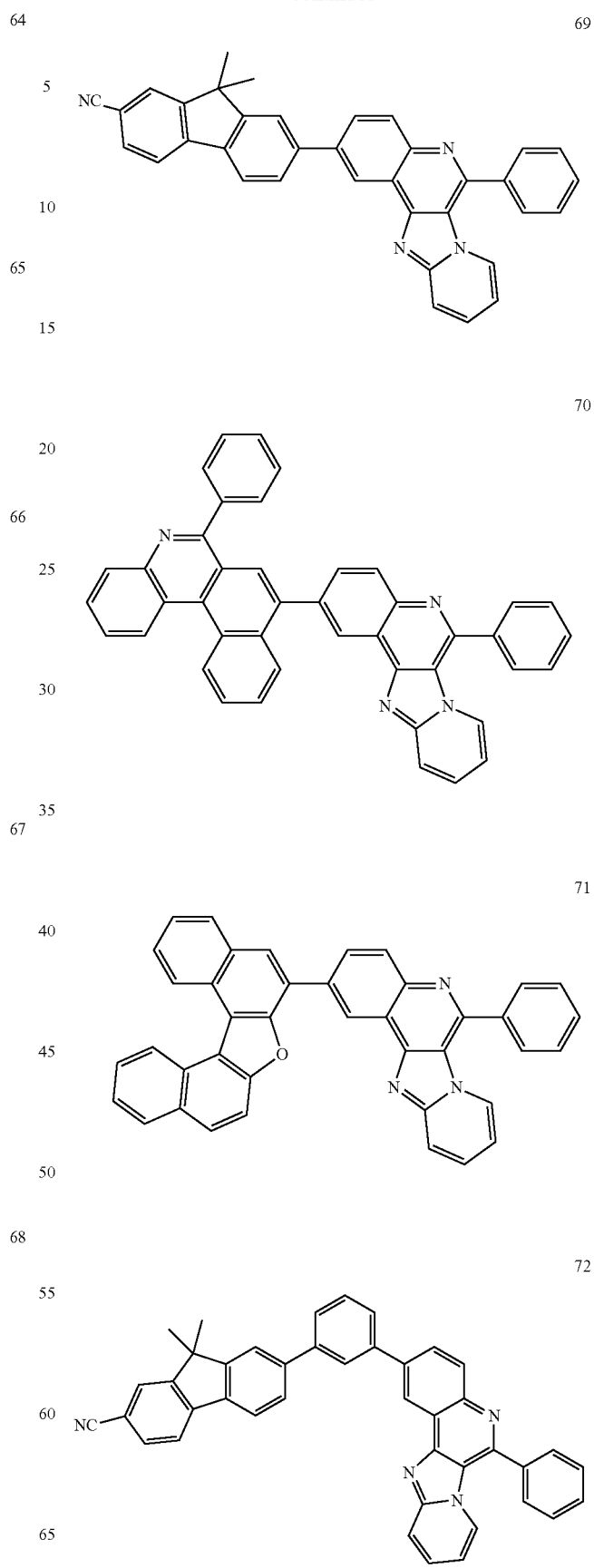

73
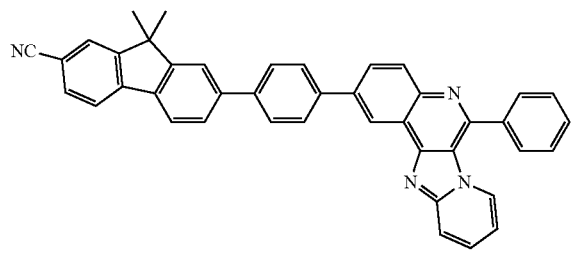
74
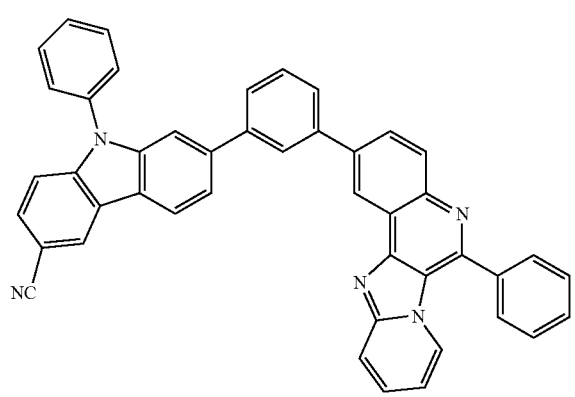
75
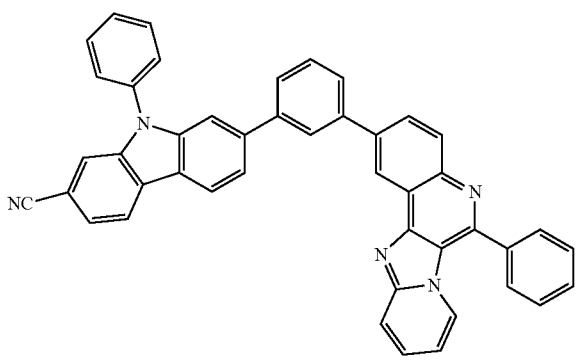
76
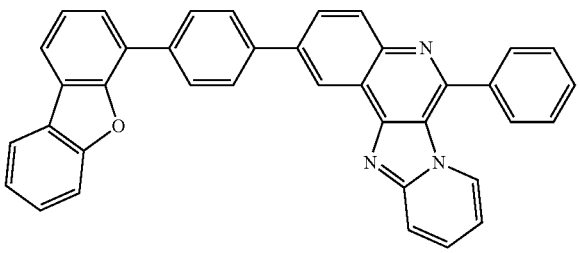
77
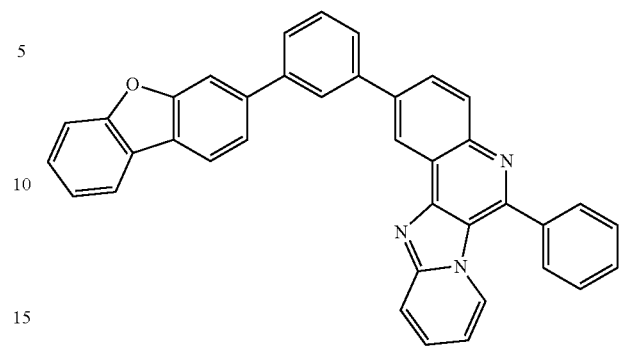
78
79
80
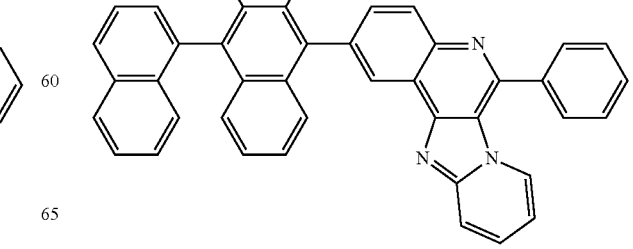

81
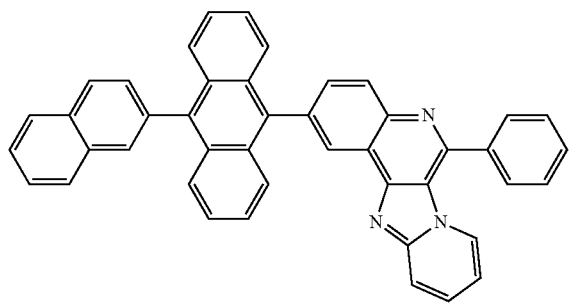
82
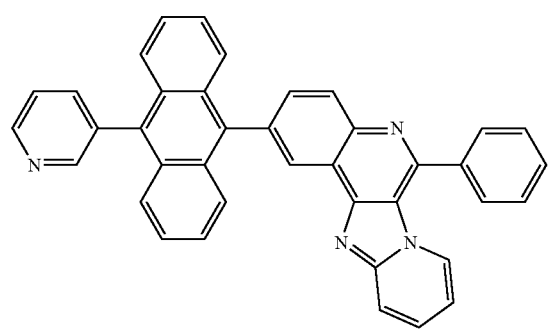
83
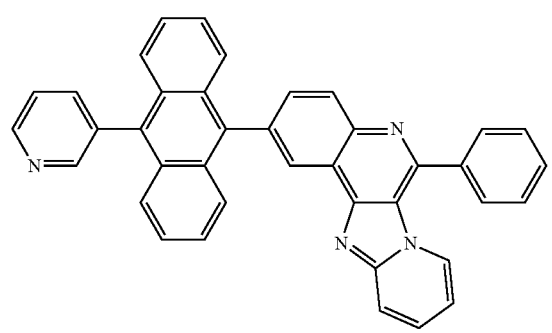
84
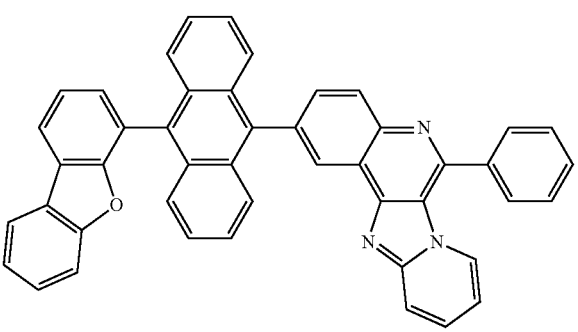
85
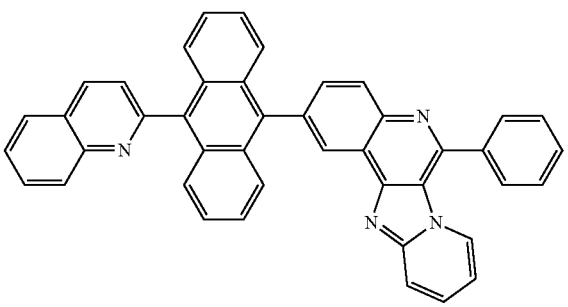
86
87
88
89
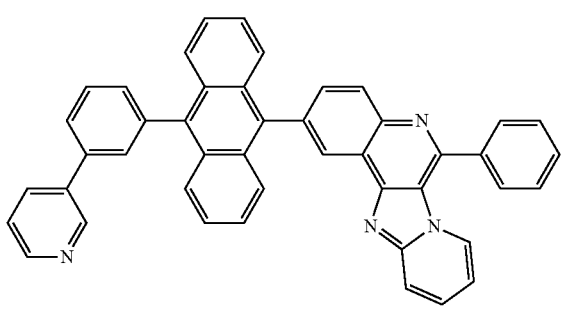

-continued

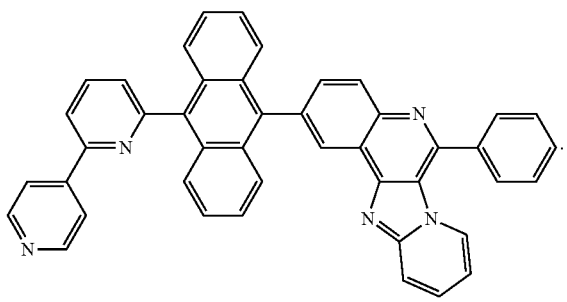

The term "organic layer" as used herein may refer to a single layer and/or a plurality of layers between the first electrode and the second electrode of an organic light-emitting device. The material included in the organic layer is not limited to being an organic material.

The drawing is a schematic view of an organic light-emitting device 10 according to an embodiment of the present disclosure. The organic light-emitting device 10 includes a first electrode 110, an organic layer 150, and a second electrode 190.

Hereinafter, the structure of an organic light-emitting device according to an embodiment of the present disclosure and a method of manufacturing an organic light-emitting device according to an embodiment of the present disclosure will be described in connection with the drawing.

In the drawing, a substrate may be under the first electrode 110 and/or on the second electrode 190. The substrate may be a glass substrate or a transparent plastic substrate, each having excellent mechanical strength, thermal stability, transparency, surface smoothness, ease of handling, and/or water-resistance.

The first electrode 110 may be formed by depositing and/or sputtering a material for forming the first electrode 110 on the substrate. When the first electrode 110 is an anode, the material for the forming first electrode 110 may be selected from materials with a high work function to facilitate hole injection. The first electrode 110 may be a reflective electrode, a semi-transmissive electrode, or a transmissive electrode. The material for forming the first electrode 110 may be a transparent and highly conductive material, and non-limiting examples of such a material may include indium tin oxide (ITO), indium zinc oxide (IZO), tin oxide ($SnO_2$), and zinc oxide (ZnO). When the first electrode 110 is a semi-transmissive electrode or a reflective electrode, at least one selected from magnesium (Mg), aluminum(Al), aluminum-lithium(Al—Li), calcium (Ca), magnesium-indium(Mg—In), and magnesium-silver (Mg—Ag) may be used as a material for forming the first electrode 110.

The first electrode 110 may have a single-layer structure, or a multi-layer structure including two or more layers. For example, the first electrode 110 may have a three-layered structure of ITO/Ag/ITO, but embodiments of the structure of the first electrode 110 are not limited thereto.

The organic layer 150 is on the first electrode 110. The organic layer 150 may include an emission layer.

The organic layer 150 may further include a hole transport region between the first electrode and the emission layer, and an electron transport region between the emission layer and the second electrode.

In some embodiments, the hole transport region may include at least one selected from a hole transport layer (HTL), a hole injection layer (HIL), a buffer layer, and an electron blocking layer, and the electron transport region may include at least one selected from a hole blocking layer (HBL), an electron transport layer (ETL), and an electron injection layer (EIL). However, embodiments of the present disclosure are not limited thereto.

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, a structure of hole injection layer/hole transport layer, a structure of hole injection layer/hole transport layer/buffer layer, a structure of hole injection layer/buffer layer, a structure of hole transport layer/buffer layer, or a structure of hole injection layer/hole transport layer/electron blocking layer, wherein layers of each structure are sequentially stacked from the first electrode 110 in each stated order, but embodiments of the present disclosure are not limited thereto.

When the hole transport region includes a hole injection layer, the hole injection layer may be formed on the first electrode 110 using one or more suitable methods selected from vacuum deposition, spin coating, casting, a Langmuir-Blodgett (LB) method, ink-jet printing, laser-printing, and laser-induced thermal imaging.

When the hole injection layer is formed by vacuum deposition, for example, the vacuum deposition may be performed at a deposition temperature of about 100 to about 500° C., at a vacuum degree of about $10^{-8}$ to about $10^{-3}$ torr, and at a deposition rate of about 0.01 to about 100 Å/sec, depending on the compound to be deposited in the hole injection layer, and the structure of the hole injection layer to be formed.

When the hole injection layer is formed by spin coating, the spin coating may be performed at a coating rate of about 2,000 rpm to about 5,000 rpm, and at a temperature of about 80° C. to 200° C., depending on the compound to be deposited in the hole injection layer, and the structure of the hole injection layer to be formed.

When the hole transport region includes a hole transport layer, the hole transport layer may be formed on the first electrode 110 or on the hole injection layer using one or more suitable methods selected from vacuum deposition, spin coating, casting, a LB method, ink-jet printing, laser-printing, and laser-induced thermal imaging. When the hole transport layer is formed by vacuum deposition and/or spin coating, the deposition and coating conditions used for the hole transport layer may be similar to the deposition and coating conditions used for the hole injection layer.

The hole transport region may include m-MTDATA, TDATA, 2-TNATA, NPB, β-NPB, TPD, Spiro-TPD, Spiro-NPB, α-NPB, TAPC, HMTPD, 4,4',4''-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201, and/or a compound represented by Formula 202:

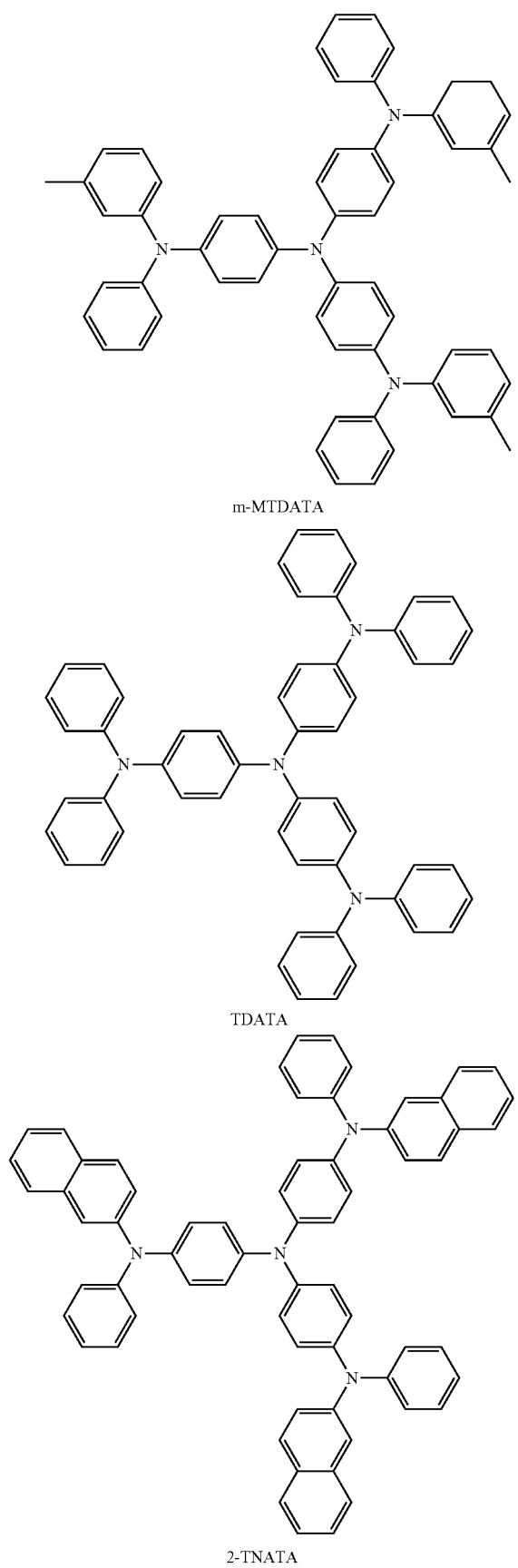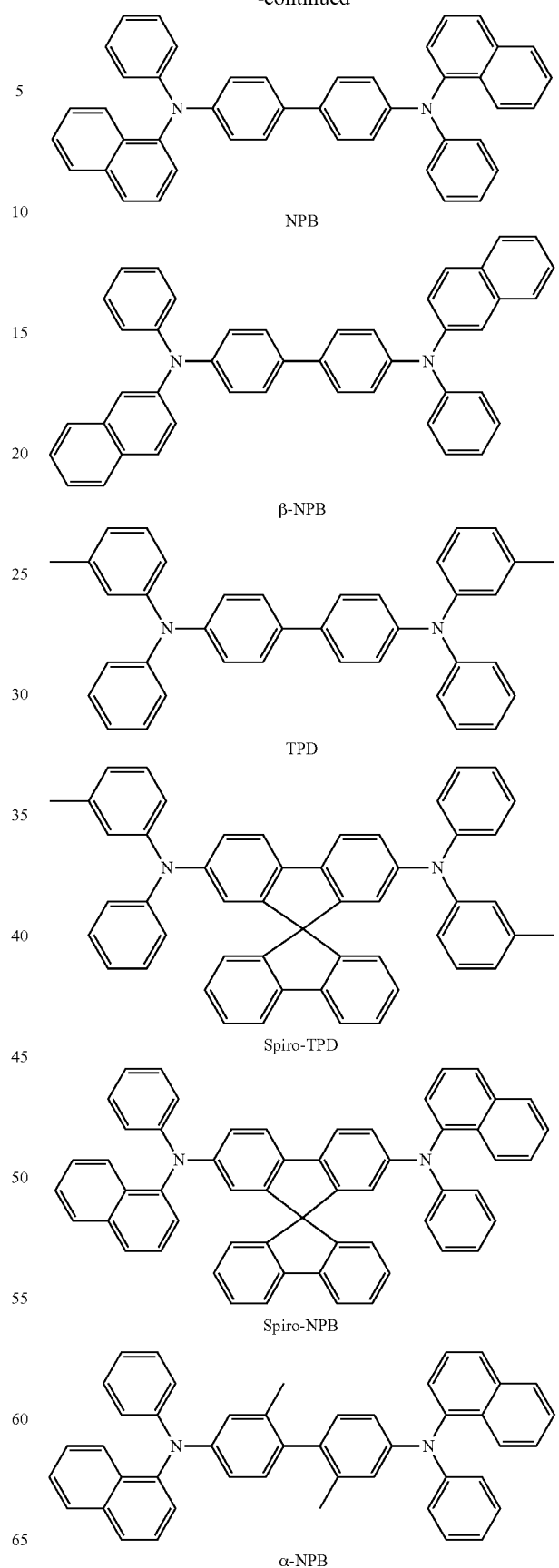

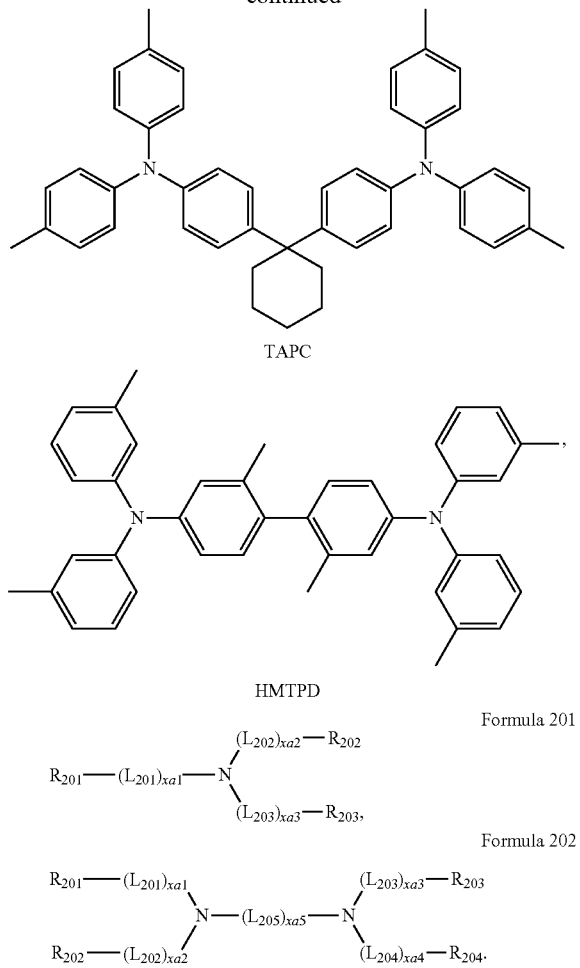

TAPC

HMTPD

Formula 201

R$_{201}$—(L$_{201}$)$_{xa1}$—N(L$_{202}$)$_{xa2}$—R$_{202}$ / (L$_{203}$)$_{xa3}$—R$_{203}$,

Formula 202

R$_{201}$—(L$_{201}$)$_{xa1}$ \ N—(L$_{205}$)$_{xa5}$—N / (L$_{203}$)$_{xa3}$—R$_{203}$
R$_{202}$—(L$_{202}$)$_{xa2}$ / \ (L$_{204}$)$_{xa4}$—R$_{204}$.

In Formulae 201 and 202,

L$_{201}$ to L$_{205}$ may each independently be selected from a substituted or unsubstituted C$_6$-C$_{60}$ arylene group, a substituted or unsubstituted C$_1$-C$_{60}$ heteroarylene group, a substituted or unsubstituted divalent non-aromatic condensed polycyclic group, and a substituted or unsubstituted divalent non-aromatic condensed heteropolycyclic group;

xa1 to xa4 may each independently be selected from 0, 1, 2, and 3;

xa5 may be selected from 1, 2, 3, 4, and 5; and

R$_{201}$ to R$_{204}$ may each independently be selected from a substituted or unsubstituted C$_3$-C$_{10}$ cycloalkyl group, a substituted or unsubstituted C$_2$-C$_{10}$ heterocycloalkyl group, a substituted or unsubstituted C$_3$-C$_{10}$ cycloalkenyl group, a substituted or unsubstituted C$_2$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formulae 201 and 202,

L$_{201}$ to L$_{205}$ may each independently be selected from the group consisting of:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may each independently be selected from 0, 1, and 2;

xa5 may be selected from 1, 2, and 3; and

R$_{201}$ to R$_{204}$ may each independently be selected from the group consisting of:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a biphenyl group, a terphenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments of the present disclosure are not limited thereto.

The compound represented by Formula 201 may be represented by Formula 201A:

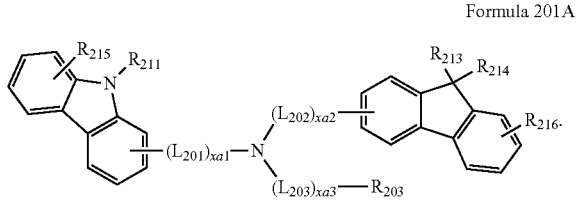

Formula 201A

For example, the compound represented by Formula 201 may be represented by Formula 201A-1, but embodiments of the present disclosure are not limited thereto:

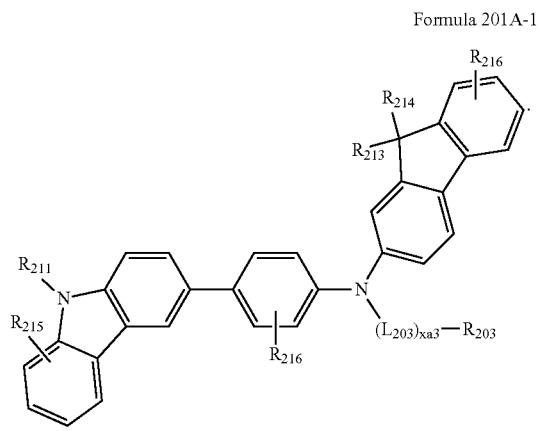

Formula 201A-1

For example, the compound represented by Formula 202 may be represented by Formula 202A, but embodiments of the present disclosure are not limited thereto:

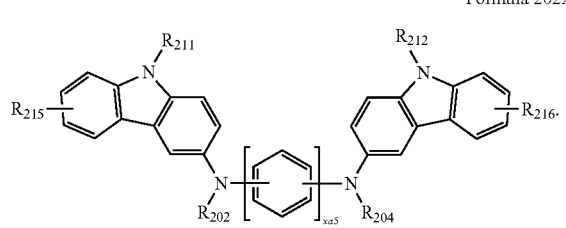

Formula 202A $L_{201}$ to $L_{203}$, xa1 to xa3, xa5, and $R_{202}$ to $R_{204}$ in Formulae 201A, 201A-1, and 202A may each be the same as described above, $R_{211}$ and $R_{212}$ may each be the same as described herein in connection with $R_{203}$, and $R_{213}$ to $R_{216}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

For example, in Formulae 201A, 201A-1, and 202A, $L_{201}$ to $L_{203}$ may each independently be selected from the group consisting of:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may each independently be selected from 0 and 1;

$R_{203}$, $R_{211}$, and $R_{212}$ may each independently be selected from the group consisting of:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ may each independently be selected from the group consisting of:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ may each independently be selected from the group consisting of:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xa5 may be selected from 1 and 2.

$R_{213}$ and $R_{214}$ in Formulae 201A and 201A-1 may be linked (e.g., coupled) to form a saturated or unsaturated ring.

The compound represented by Formula 201 and the compound represented by Formula 202 may each be or include at least one selected from Compounds HT1 to HT20, but embodiments of the present disclosure are not limited thereto.

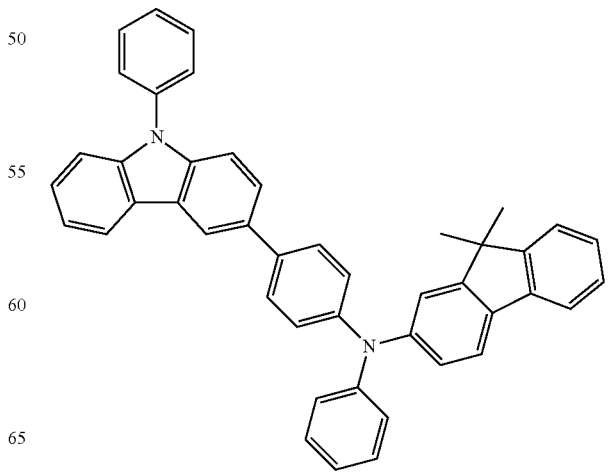

HT1

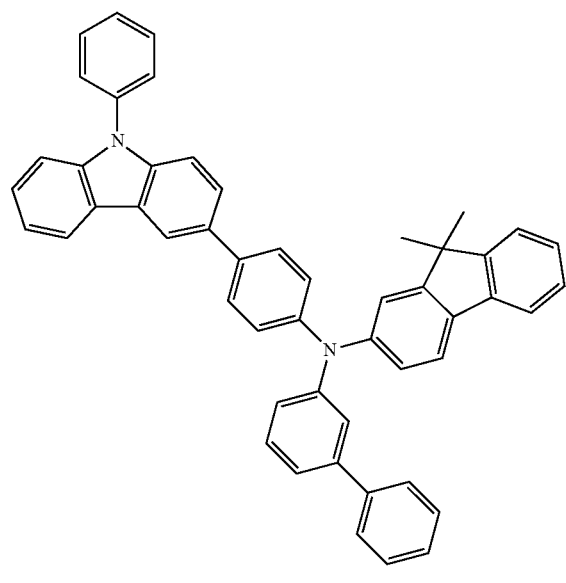
HT2
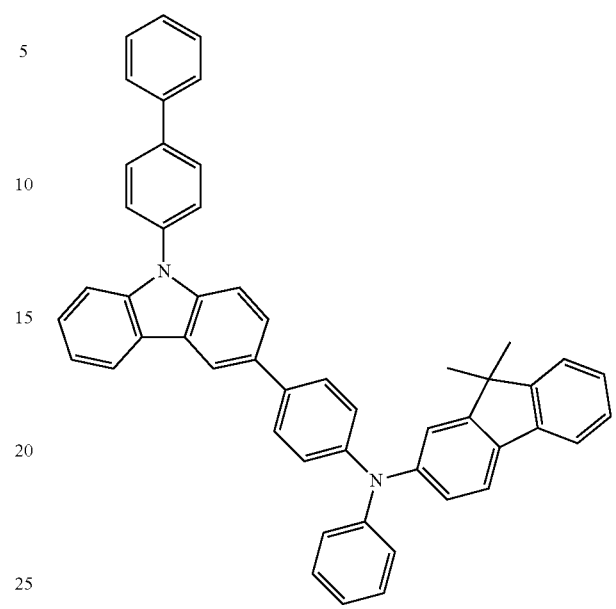
HT4
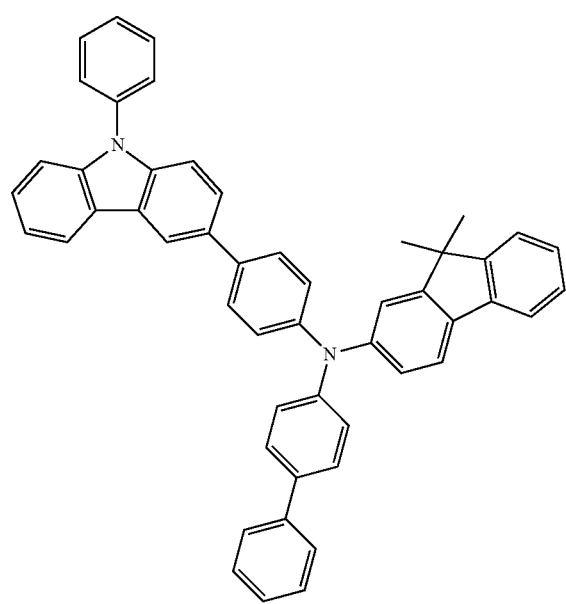
HT3
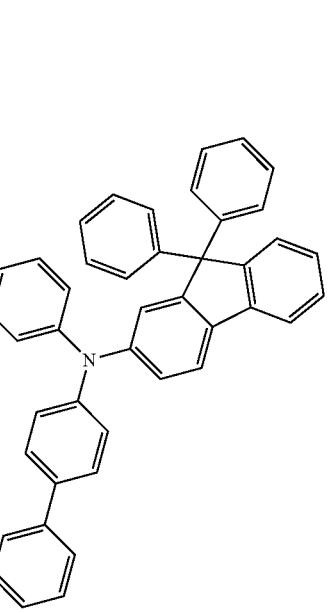
HT5

HT6
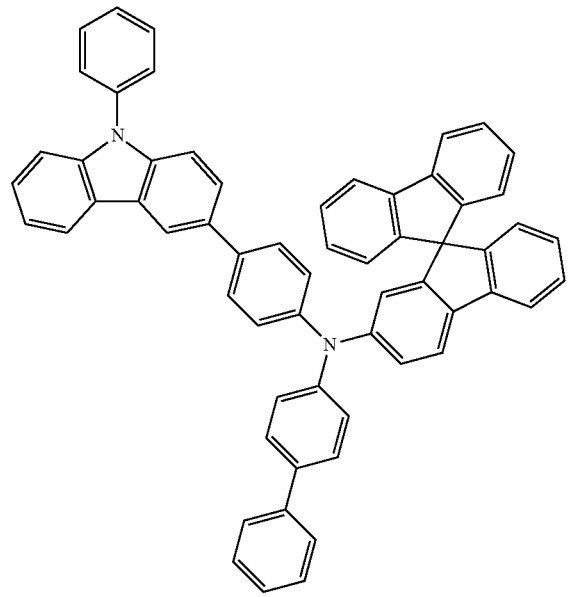
HT8
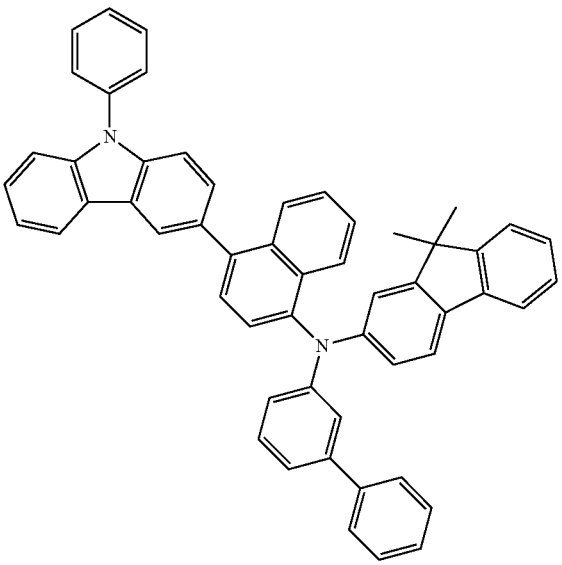
HT7
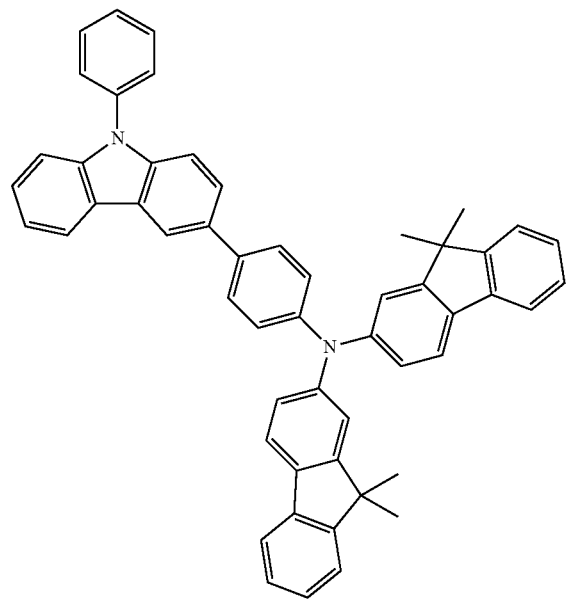
HT9
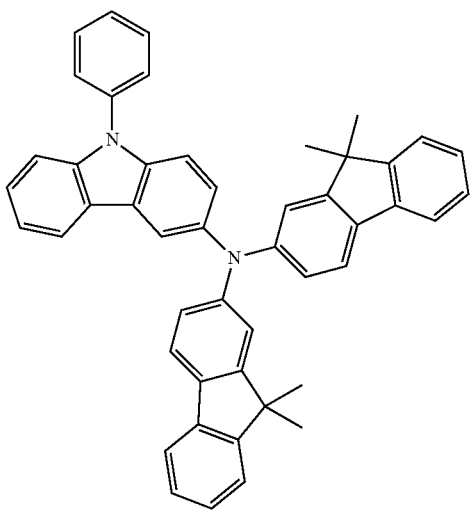

HT10
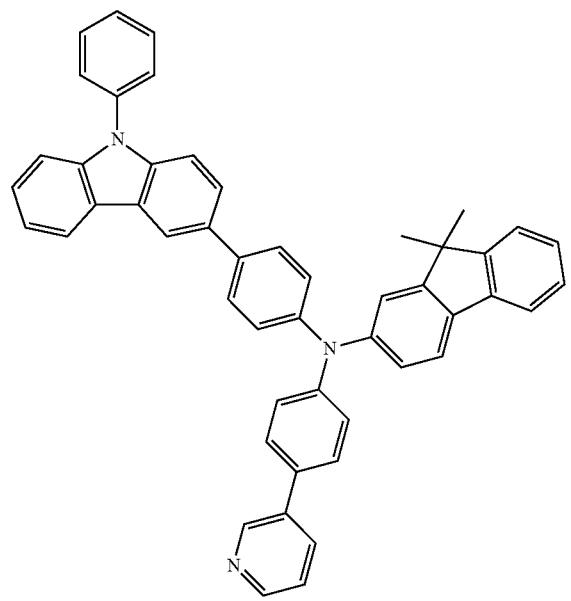
HT12
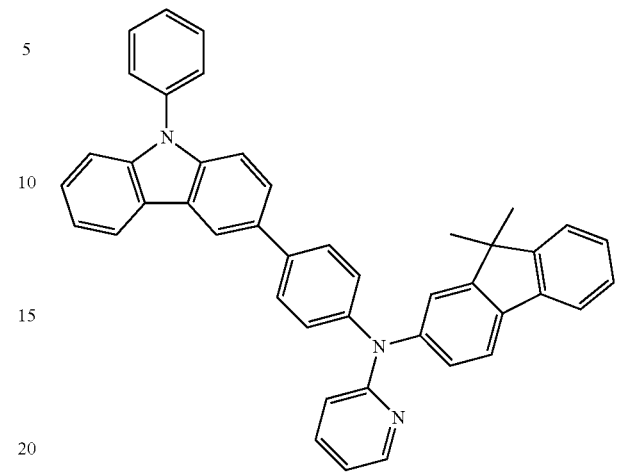
HT13
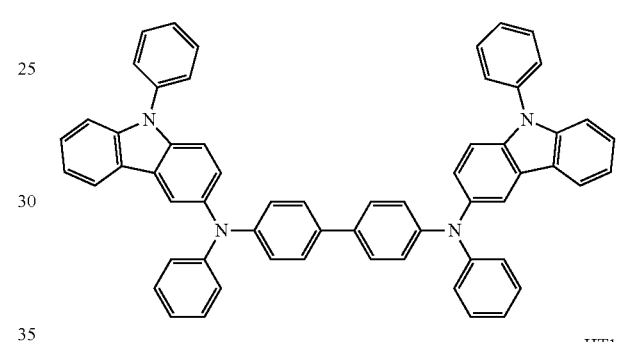
HT14
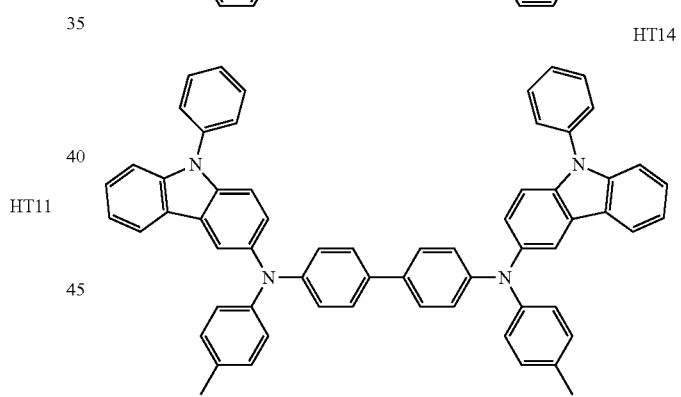
HT11
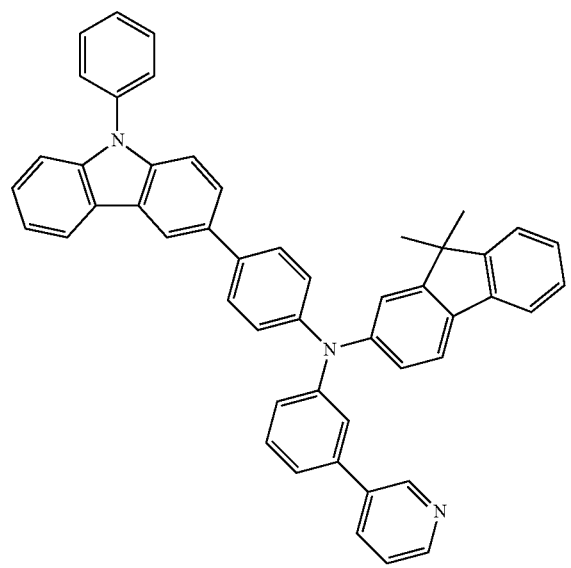
HT15
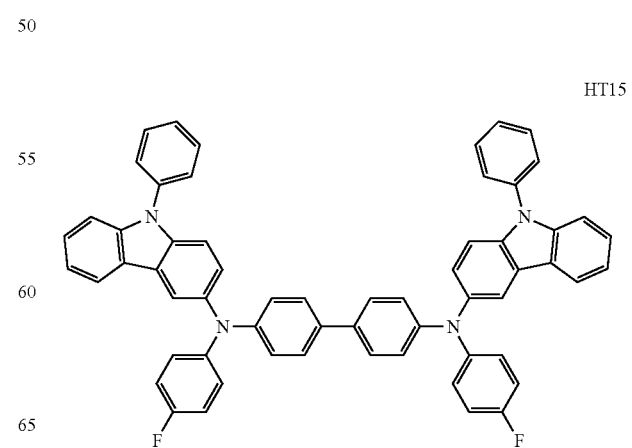

HT16

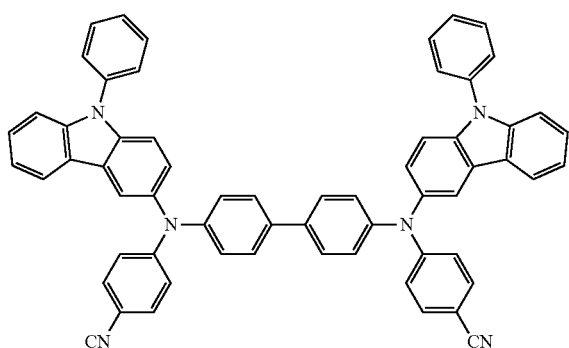

HT20

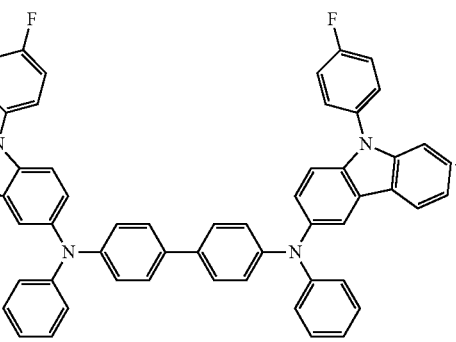

HT17

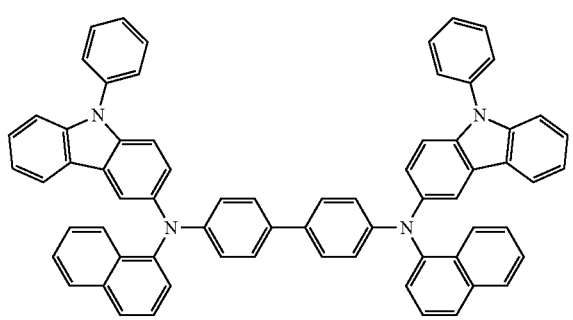

The thickness of the hole transport region may be about 100 Å to about 10,000 Å, and in some embodiments, about 100 Å to about 1,000 Å. When the hole transport region includes a hole injection layer and a hole transport layer, the thickness of the hole injection layer may be about 100 Å to about 10,000 Å, and in some embodiments, about 100 Å to about 1,000 Å; the thickness of the hole transport layer may be about 50 Å to about 2,000 Å, and in some embodiments, about 100 Å to about 1,500 Å. When the thicknesses of the hole transport region, the hole injection layer, and the hole transport layer are each within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments of the present disclosure are not limited thereto. Non-limiting examples of the p-dopant may include a quinone derivative (such as tetracyanoquinonedimethane (TCNQ) and/or 2,3,5,6-tetrafluoro-tetracyano-1,4-benzoquinonedimethane (F4-TCNQ)); a metal oxide (such as a tungsten oxide and/or a molybdenum oxide), and Compound HT-D1, but embodiments of the present disclosure are not limited thereto:

HT18

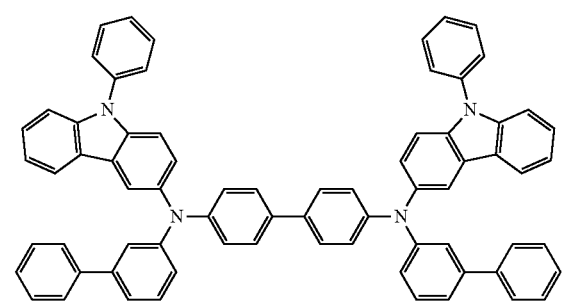

HT19

Compound HT-D1

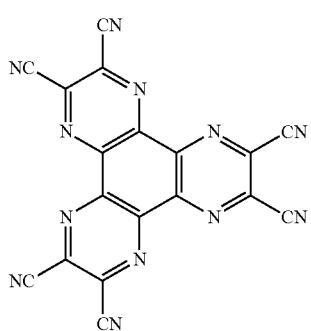

F4-TCNQ

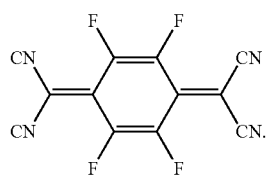

The hole transport region may include a buffer layer, in addition to an electron blocking layer, a hole injection layer, and a hole transport layer. Since the buffer layer may compensate for an optical resonance distance according to a wavelength of light emitted from the emission layer (e.g., be used to adjust the optical resonance distance to match the wavelength of light emitted from the emission layer), the light-emission efficiency of a formed organic light-emitting device may be improved. Materials that are included in the hole transport region may also be used in the buffer layer. The electron blocking layer may prevent or reduce injection of electrons from the electron transport region.

An emission layer may be formed on the first electrode 110 or on the hole transport region using one or more methods selected from vacuum deposition, spin coating, casting, a LB method, ink-jet printing, laser-printing, and laser-induced thermal imaging. When an emission layer is formed by vacuum deposition and/or spin coating, the deposition and coating conditions for the emission layer may be similar to those used for the hole injection layer.

When the organic light-emitting device 10 is a full color organic light-emitting device, the emission layer may be patterned into a red emission layer, a green emission layer, or a blue emission layer, according to a sub pixel. In some embodiments, the emission layer may have a stacked structure including a red emission layer, a green emission layer, and a blue emission layer, or may include a red-light emission material, a green-light emission material, and a blue-light emission material, which are mixed with each other in a single layer to thereby emit white light.

The emission layer may include a host and/or a dopant.

For example, the host may include at least one selected from TPBi, TBADN, ADN (also referred to as "DNA"), CBP, CDBP, and TCP:

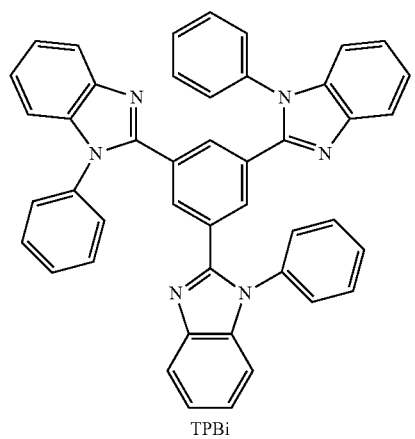

TPBi

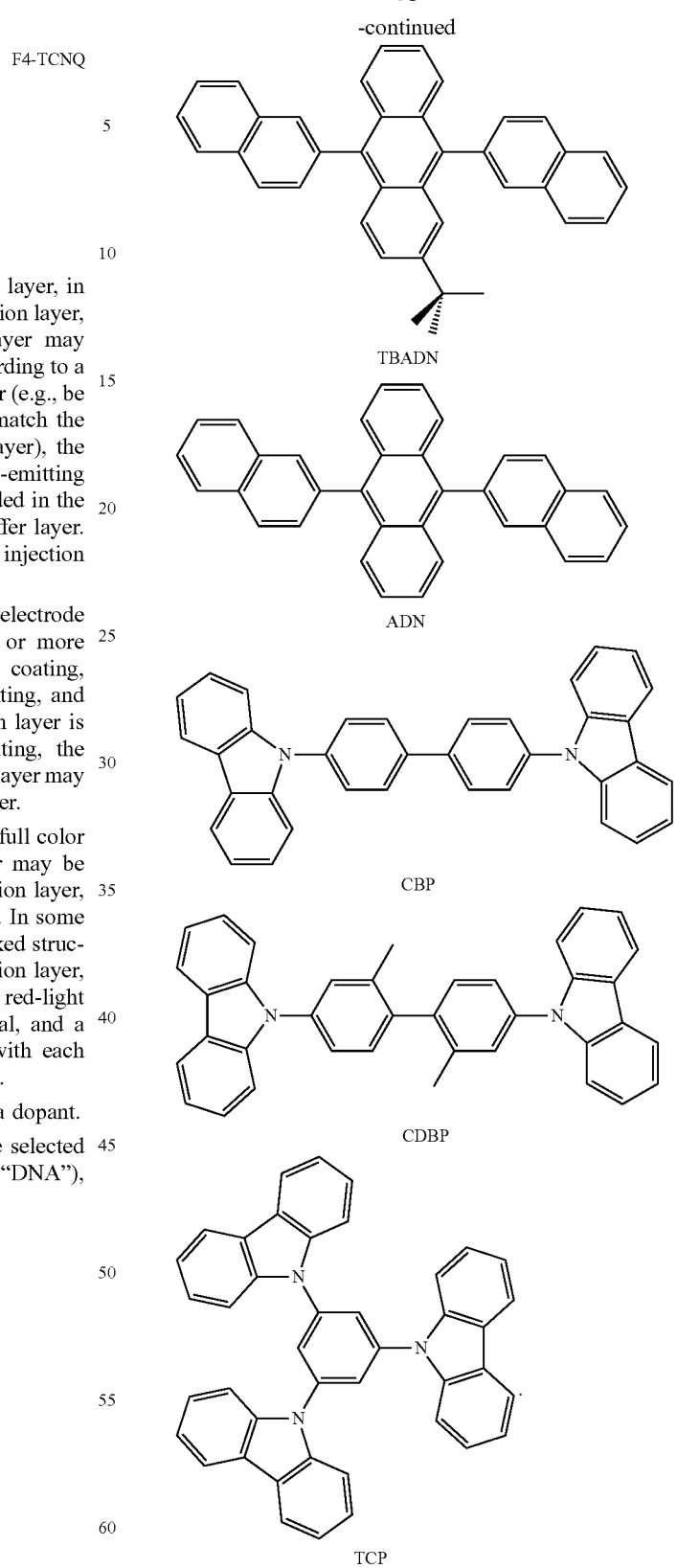

In some embodiments, the host may include a compound represented by Formula 301:

$$Ar_{301}-[(L_{301})_{xb1}-R_{301}]_{xb2}.$$

Formula 301

In Formula 301, $Ar_{301}$ may be selected from the group consisting of:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, monovalent non-aromatic condensed heteropolycyclic group, and —Si($Q_{301}$)($Q_{302}$)($Q_{303}$) (wherein $Q_{301}$ to $Q_{303}$ may each independently be selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

$L_{301}$ may be selected from the group consisting of:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

$R_{301}$ may be selected from the group consisting of:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3; and xb2 may be selected from 1, 2, 3, and 4.

For example, in Formula 301, $L_{301}$ may be selected from the group consisting of:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and $R_{301}$ may be selected from the group consisting of:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but embodiments of the present disclosure are not limited thereto.

For example, the host may include a compound represented by Formula 301A:

Formula 301A

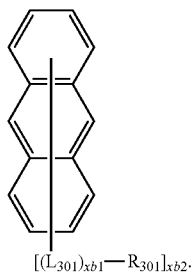

$[(L_{301})_{xb1}$—$R_{301}]_{xb2}$.

The substituents of Formula 301A may be the same as described above.

The compound represented by Formula 301 may be or include at least one selected from Compounds H1 to H42, but embodiments of the present disclosure are not limited thereto:

H1

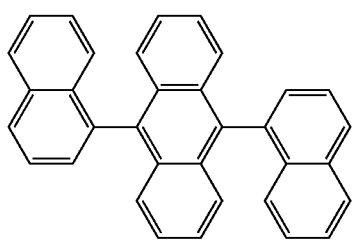

H2

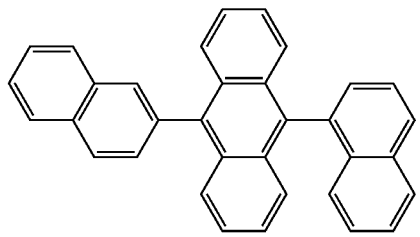

H3

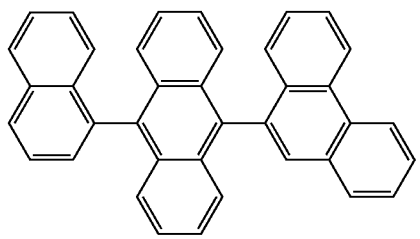

H4

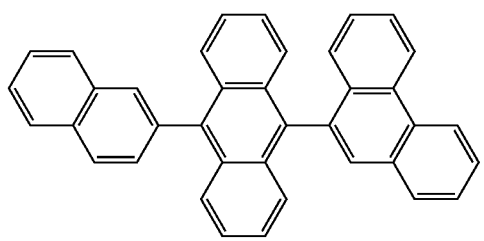

H5

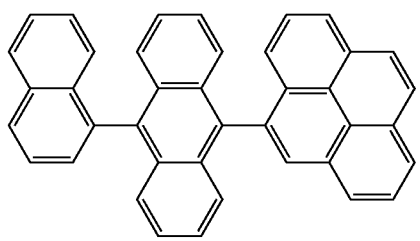

H6

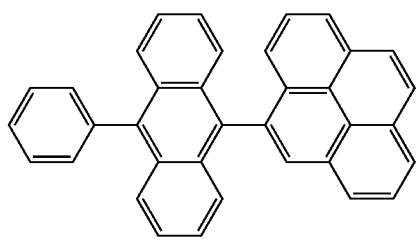

H7

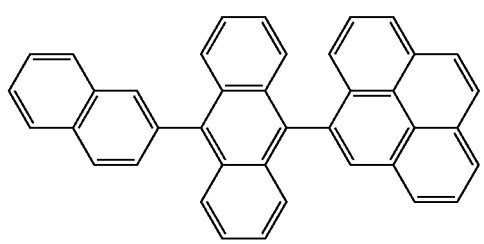

H8
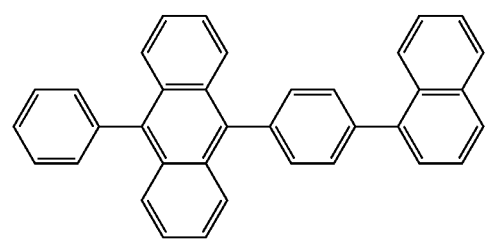
H9
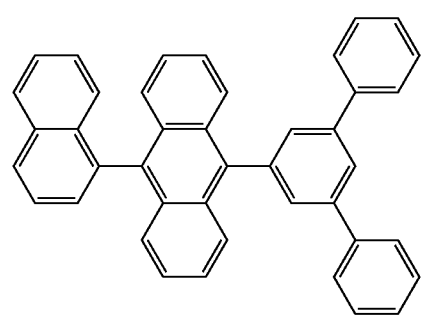
H10
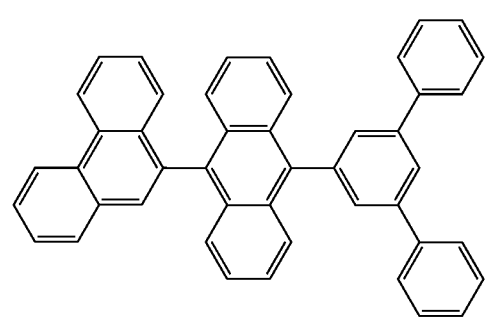
H11
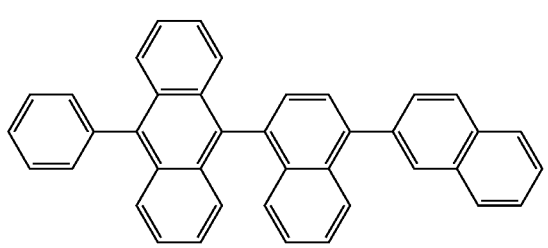
H12
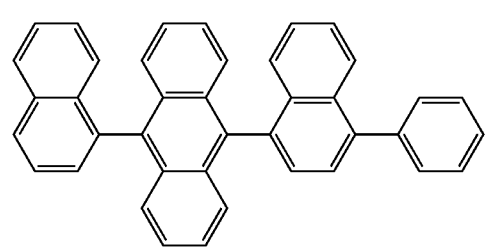
H13
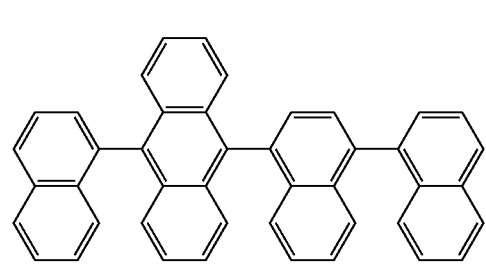
H14
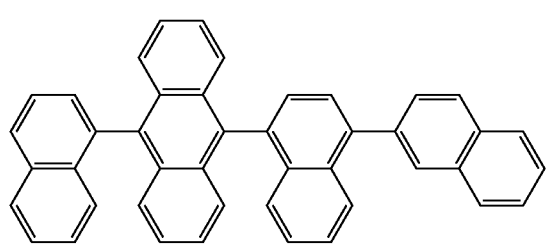
H15
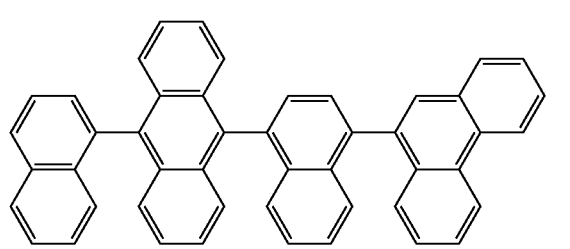
H16
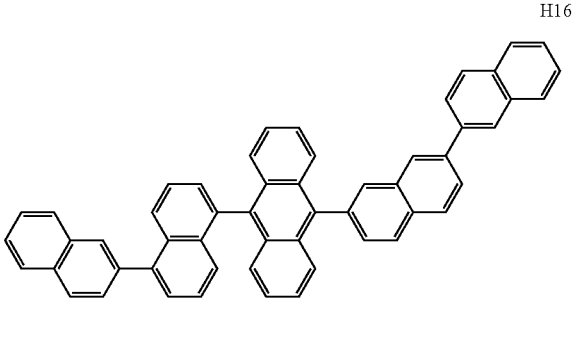
H17
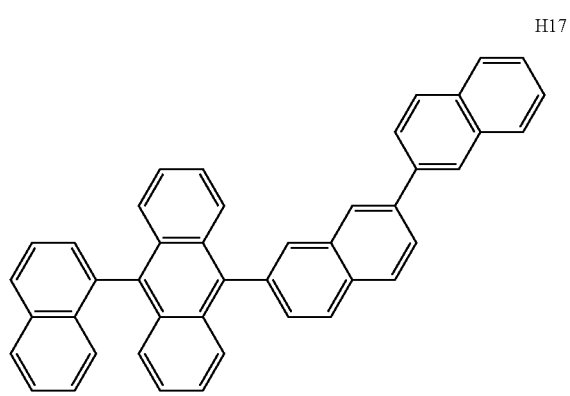
H18
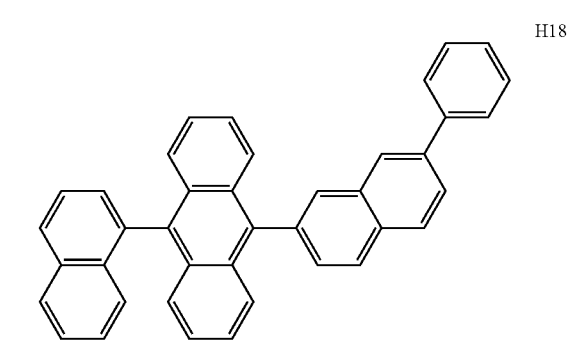

-continued
H19
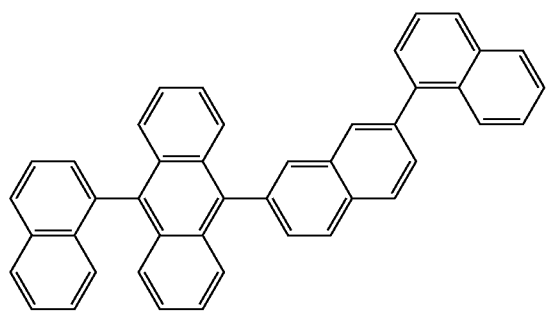
H20
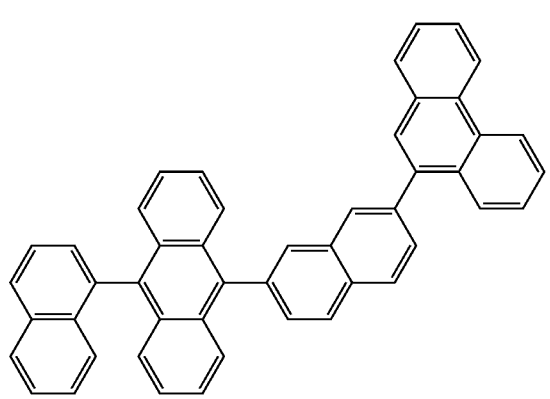
H21
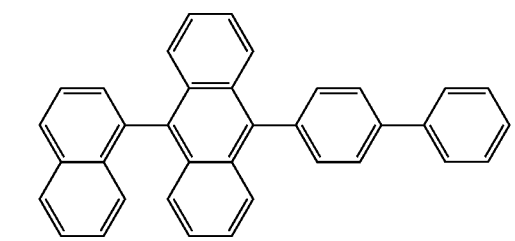
H22
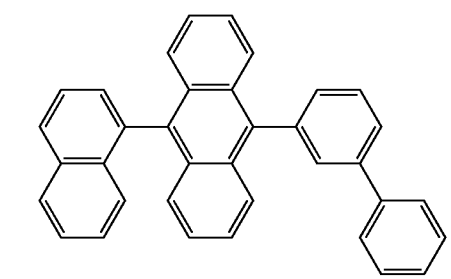
H23
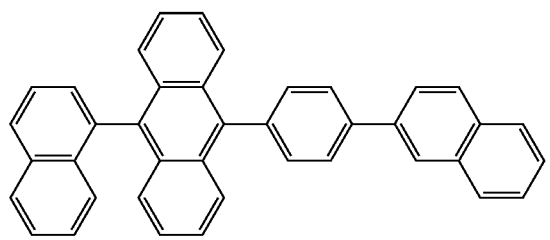
-continued
H24
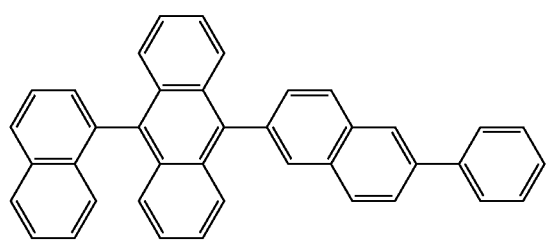
H25
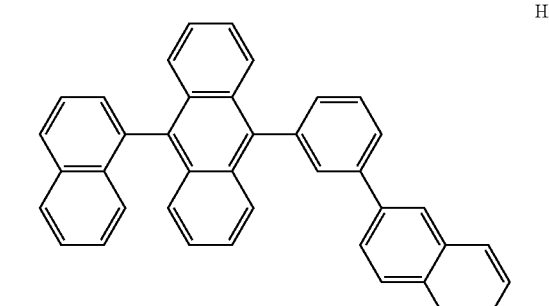
H26
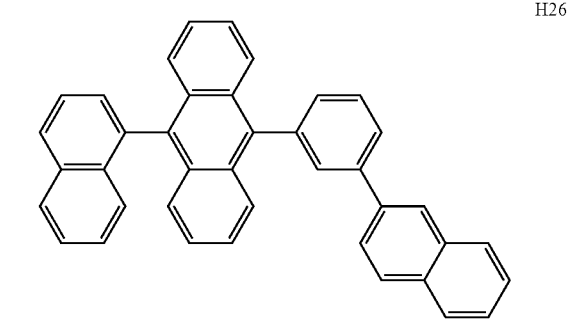
H27
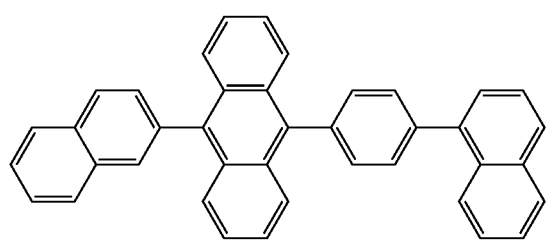
H28
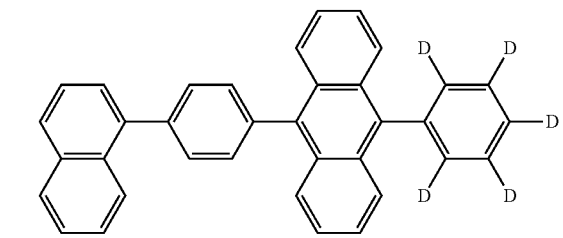

H29
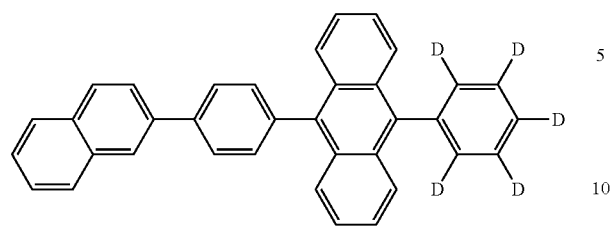
H30
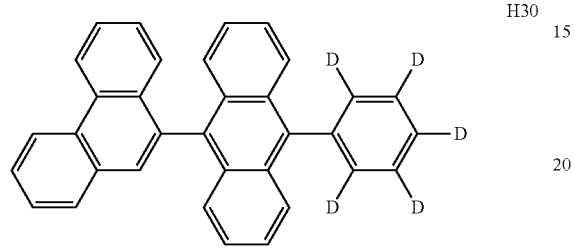
H31
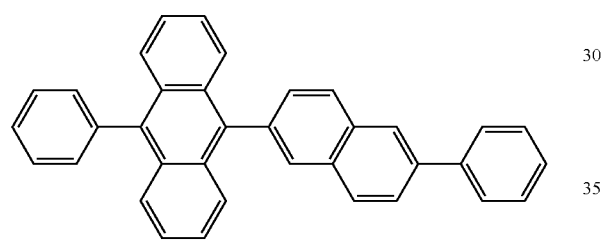
H32
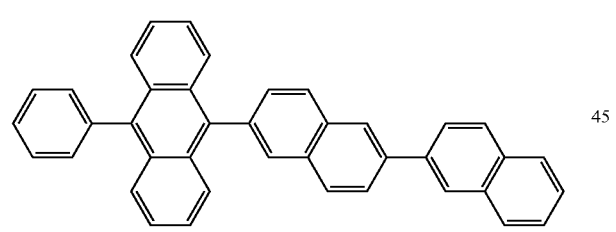
H33
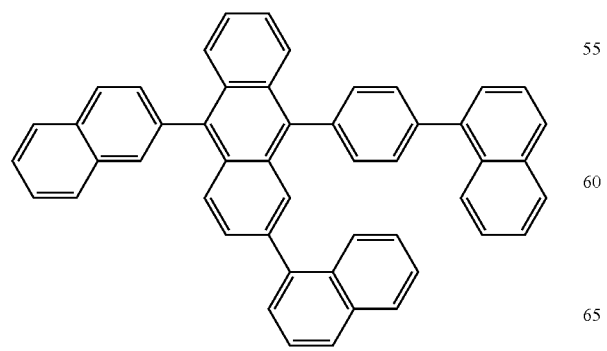
H34
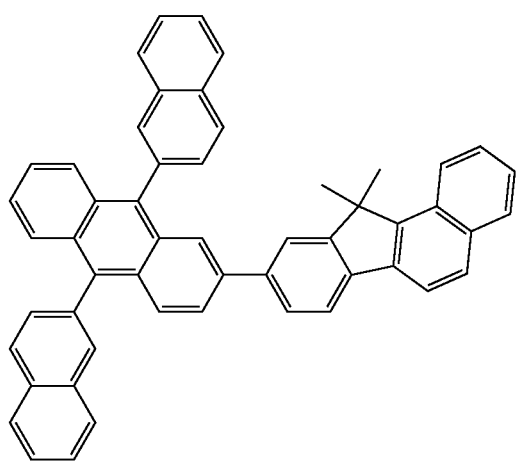
H35
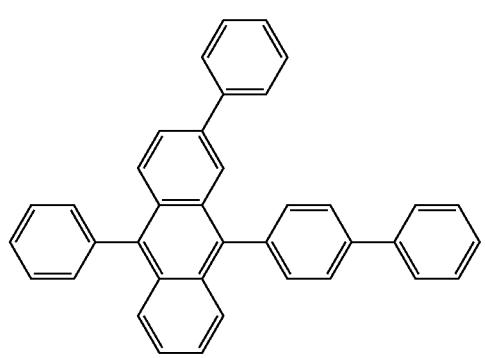
H36
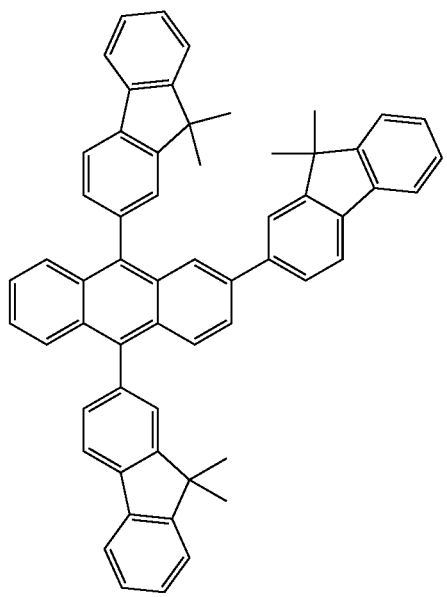

H37
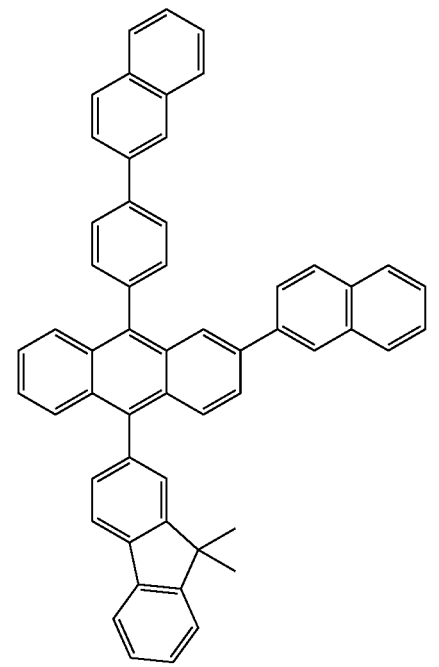
H38
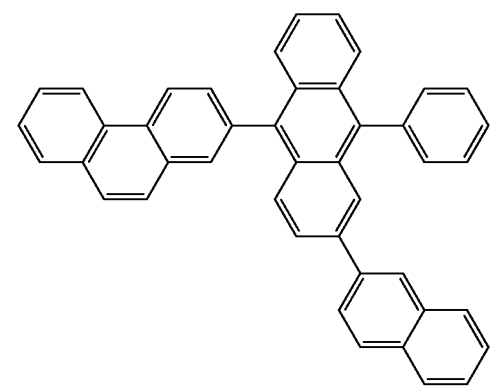
H39
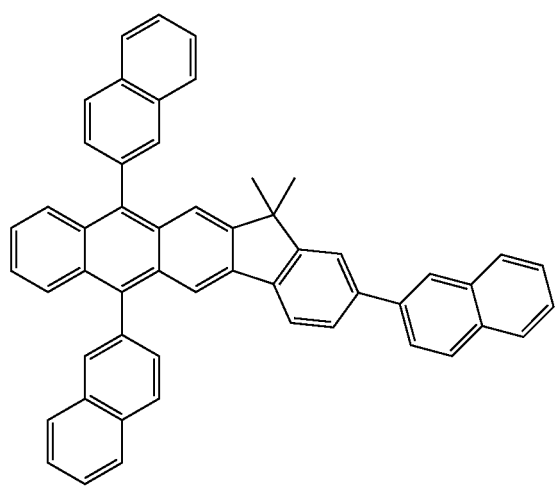
H40
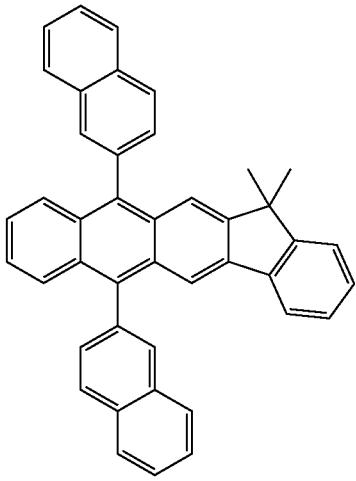
H41
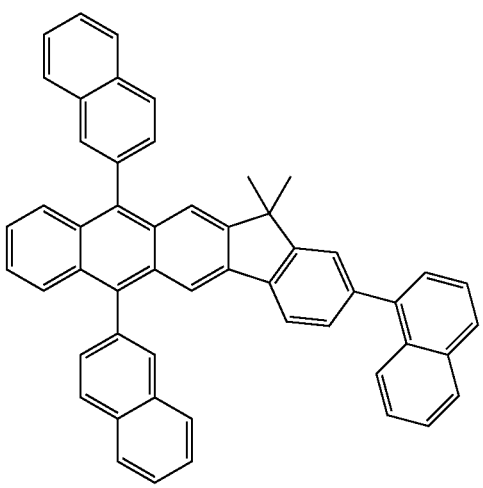
H42
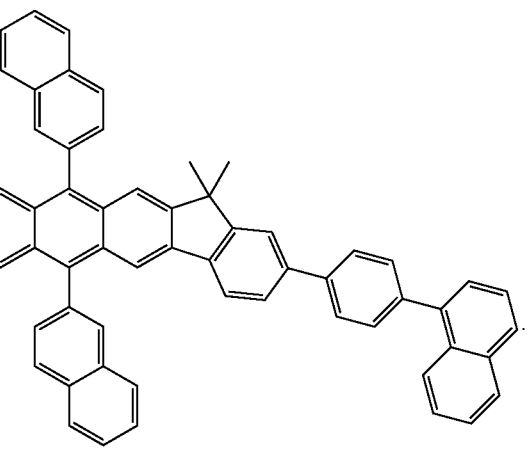
In some embodiments, the host may be or include at least one selected from Compounds H43 to H49, but embodiments of the present disclosure are not limited thereto:

H43
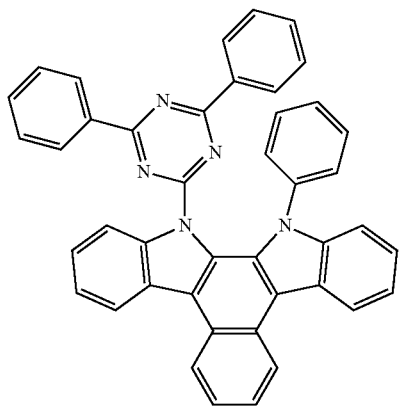
H44
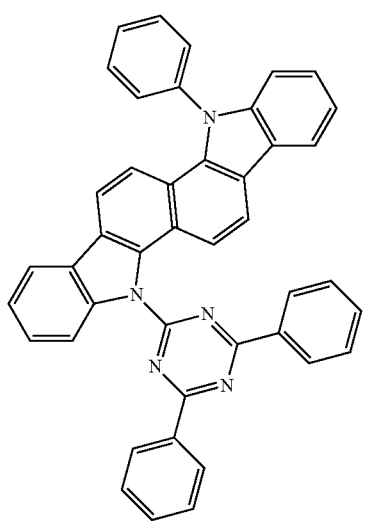
H45
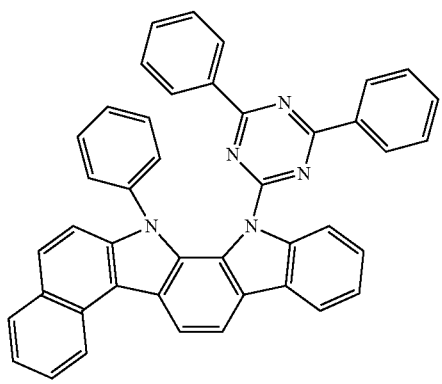
H46
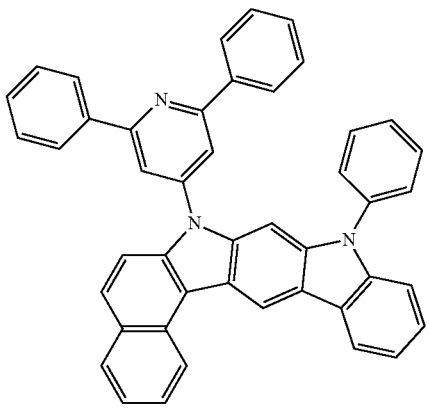
H47
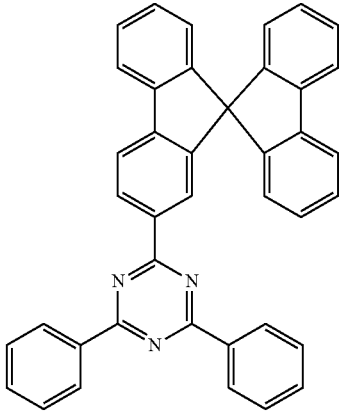
H48
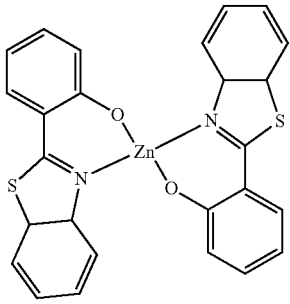
H49
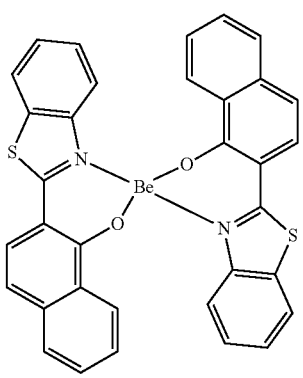
The dopant may include a fluorescent dopant and/or a phosphorescent dopant available in the related art.
The phosphorescent dopant may include an organometallic complex represented by Formula 401:

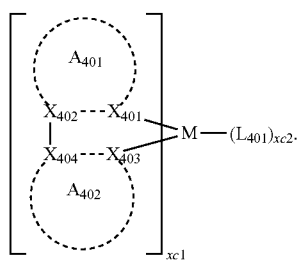

Formula 401

In Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may each independently be selected from nitrogen (N) and carbon (C);

rings $A_{401}$ and $A_{402}$ may each independently be selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene; and at least one substituent of the substituted benzene, substituted naphthalene, substituted fluorene, substituted spiro-fluorene, substituted indene, substituted pyrrole, substituted thiophene, substituted furan, substituted imidazole, substituted pyrazole, substituted thiazole, substituted isothiazole, substituted oxazole, substituted isoxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazole, substituted benzimidazole, substituted benzofuran, substituted benzothiophene, substituted isobenzothiophene, substituted benzoxazole, substituted isobenzoxazole, substituted triazole, substituted oxadiazole, substituted triazine, substituted dibenzofuran, and substituted dibenzothiophene may be selected from the group consisting of:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_1$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$) and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$), wherein $Q_{401}$ to $Q_{407}$, $Q_{411}$ to $Q_{417}$, and $Q_{421}$ to $Q_{427}$ may each independently be the same as described herein in connection with $Q_{11}$.

$L_{401}$ may be an organic ligand;

xc1 may be selected from 1, 2, and 3; and xc2 may be selected from 0, 1, 2, and 3.

$L_{401}$ may be a monovalent, divalent, or trivalent organic ligand. For example, $L_{401}$ may be selected from a halogen ligand (for example, Cl and/or F), a diketone ligand (for example, acetylacetonate, 1,3-diphenyl-1,3-propandionate, 2,2,6,6-tetramethyl-3,5-heptandionate, and/or hexafluoroacetonate), a carboxylic acid ligand (for example, picolinate, dimethyl-3-pyrazolecarboxylate and/or benzoate), a carbon monoxide ligand, an isonitrile ligand, a cyano ligand, and a phosphorous ligand (for example, phosphine and/or phosphite), but embodiments of the present disclosure are not limited thereto.

When $A_{401}$ in Formula 401 has two or more substituents, the substituents of $A_{401}$ may be linked (e.g., coupled) to form a saturated or unsaturated ring.

When $A_{402}$ in Formula 401 has two or more substituents, the substituents of $A_{402}$ may be linked (e.g., coupled) to form a saturated or unsaturated ring.

When xc1 in Formula 401 is 2 or more, a plurality of ligands

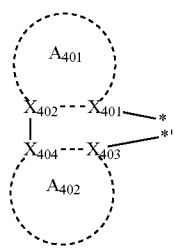

in Formula 401 may be identical to or different from each other. When xc1 in Formula 401 is 2 or more, $A_{401}$ and $A_{402}$ may each be directly connected (e.g., by a bond) or connected via a linking group (for example, a $C_1$-$C_5$ alkylene group, —N(R')— (wherein R' may be a $C_1$-$C_{10}$ alkyl group or a $C_6$-$C_{20}$ aryl group), and/or —C(=O)—) to $A_{401}$ and $A_{402}$, respectively, of a neighboring ligand.

The phosphorescent dopant may be or include at least one selected from Compounds PD1 to PD74, but embodiments of the present disclosure are not limited thereto:

PD1

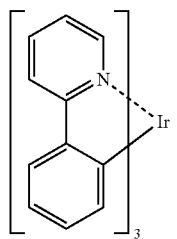

PD2

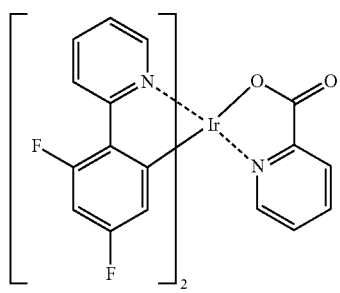

PD3

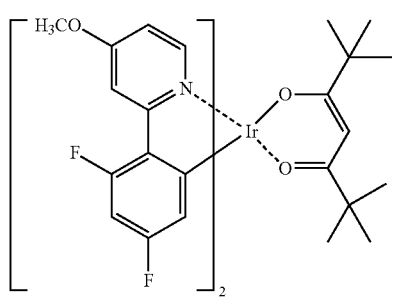

PD4

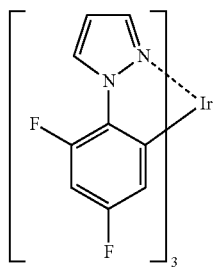

PD5

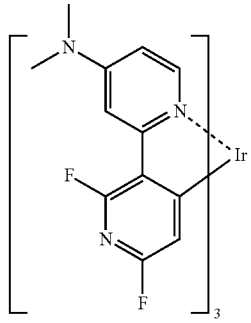

PD6

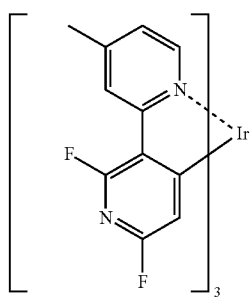

PD7

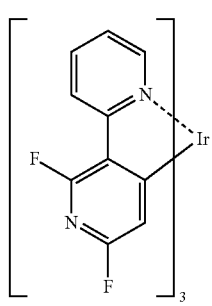

PD8

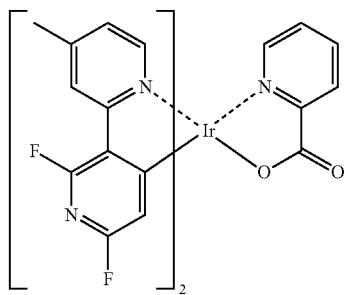

-continued
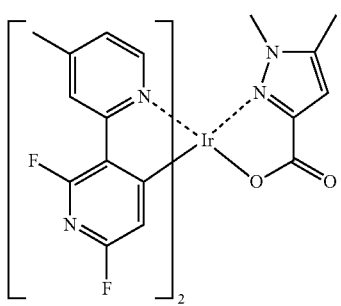
PD9
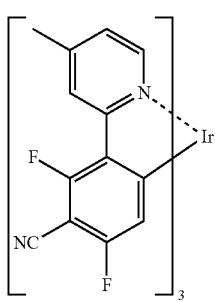
PD10
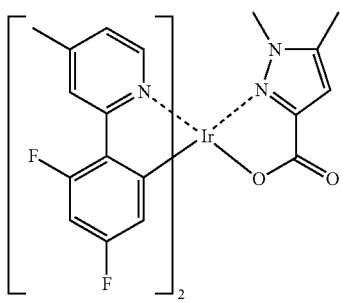
PD11
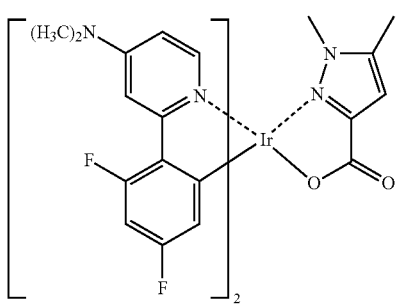
PD12
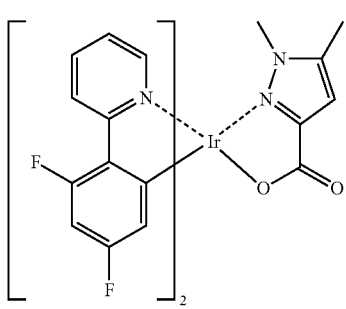
PD13
-continued
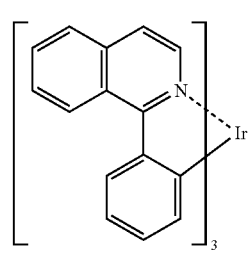
PD14
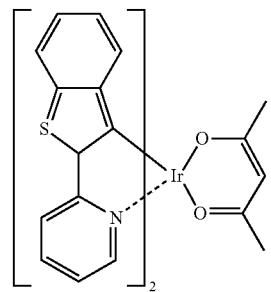
PD15
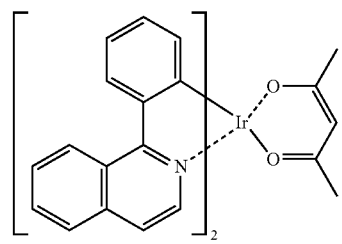
PD16
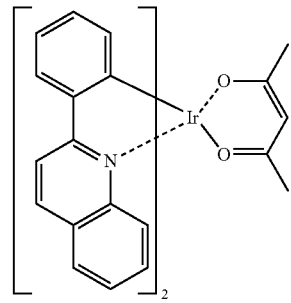
PD17
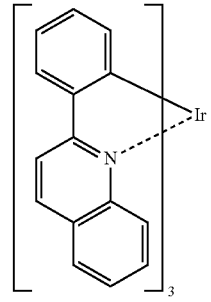
PD18

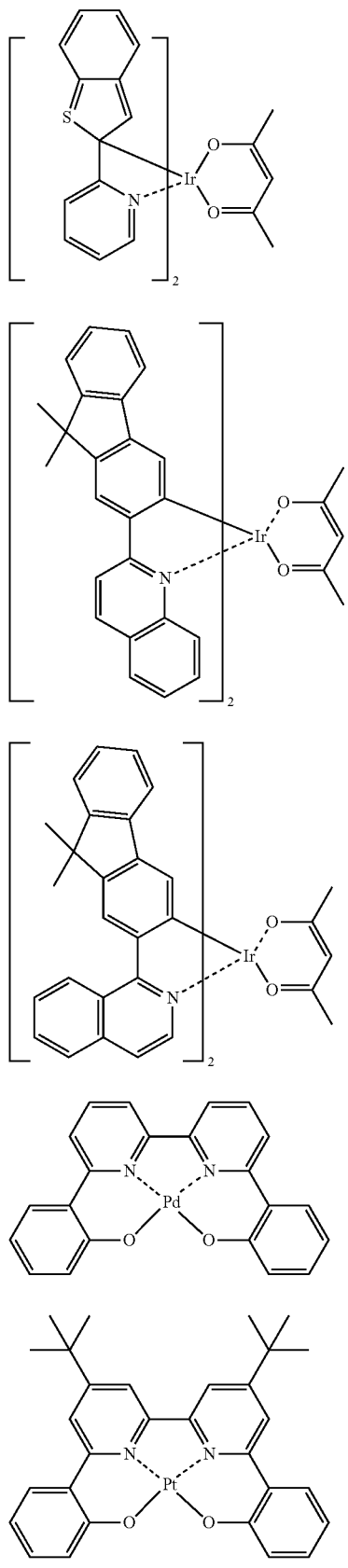
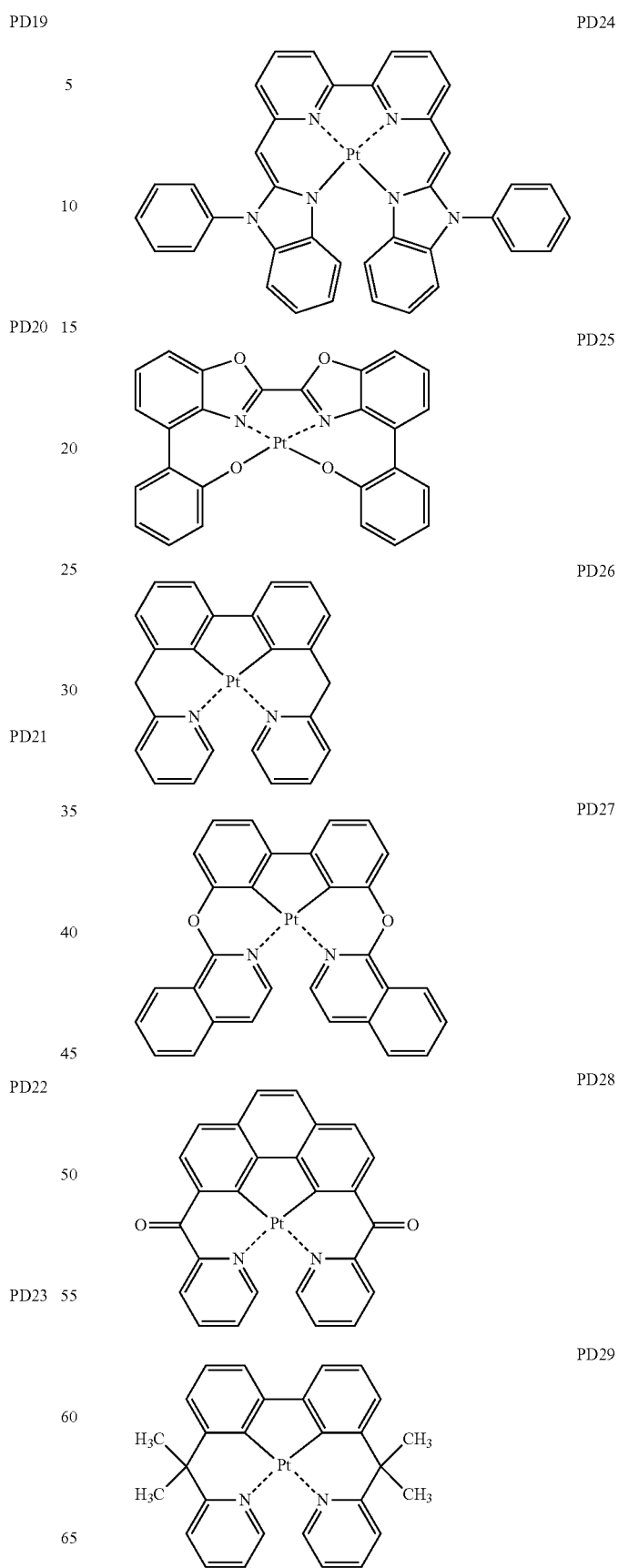

-continued
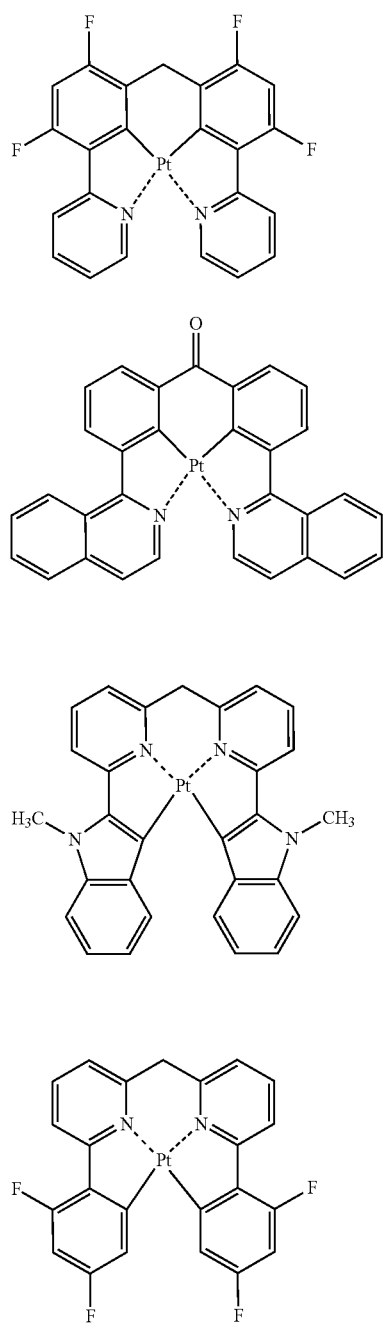
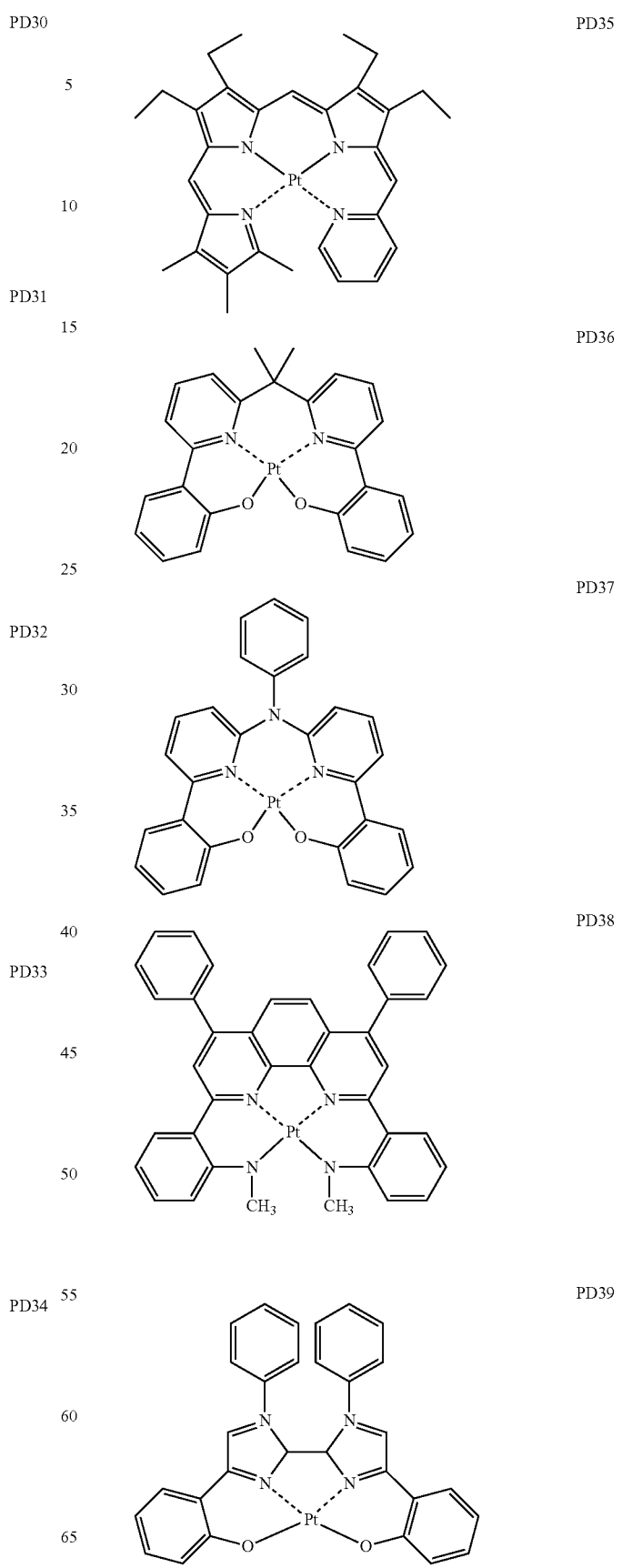

-continued
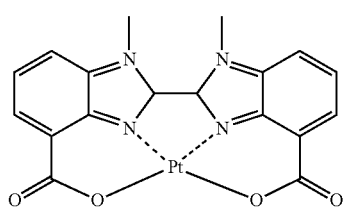
PD40
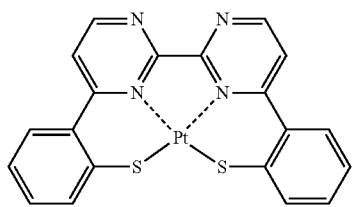
PD41
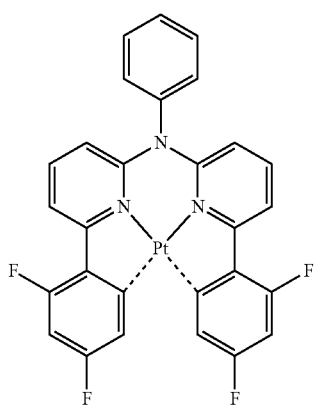
PD42
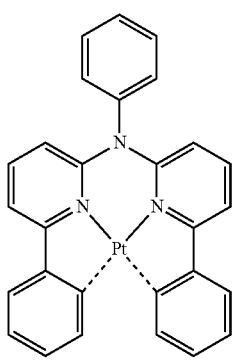
PD43
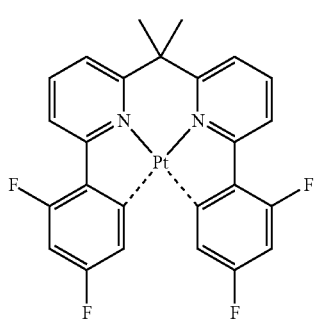
PD44
-continued
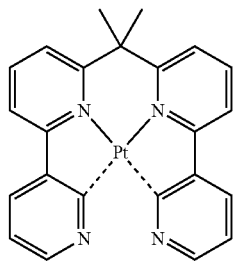
PD45
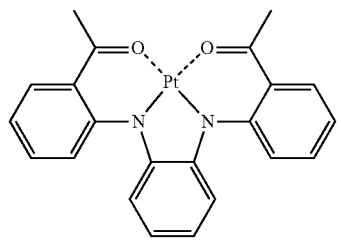
PD46
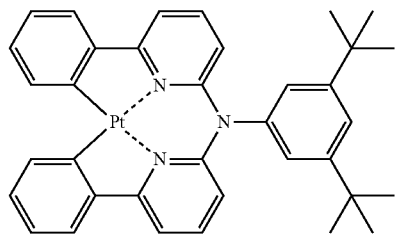
PD47
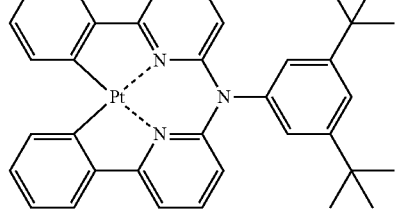
PD48
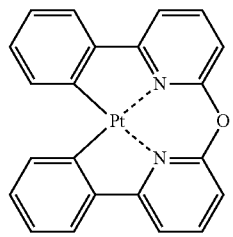
PD49
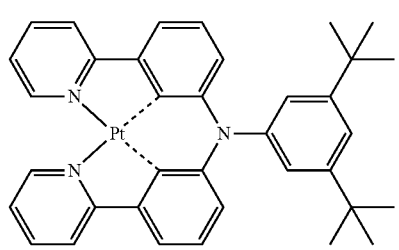
PD50

PD51 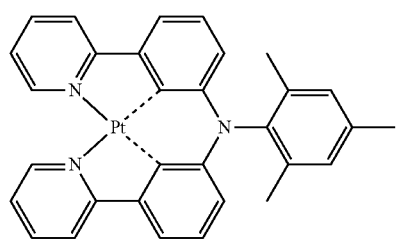
PD52 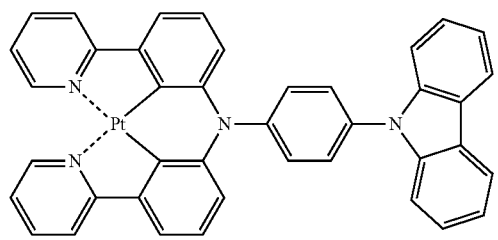
PD53 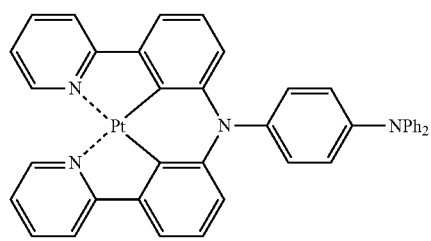
PD54 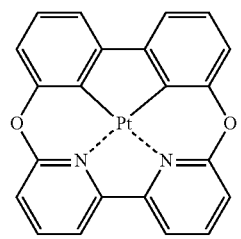
PD55 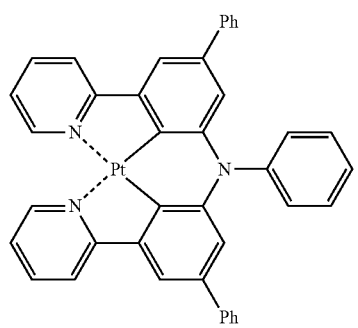
PD56 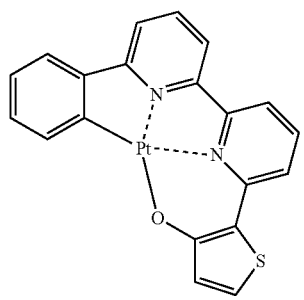
PD57 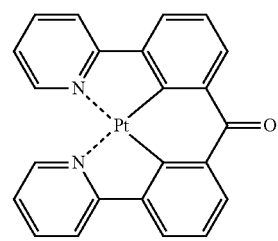
PD58 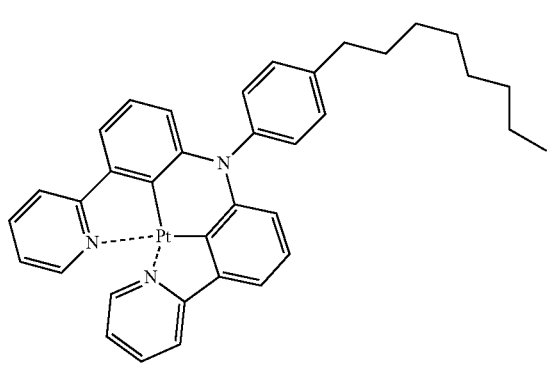
PD59 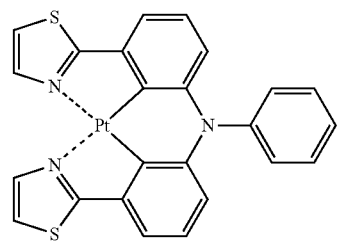
PD60 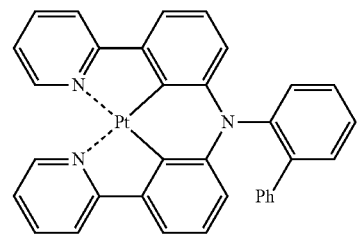
PD61 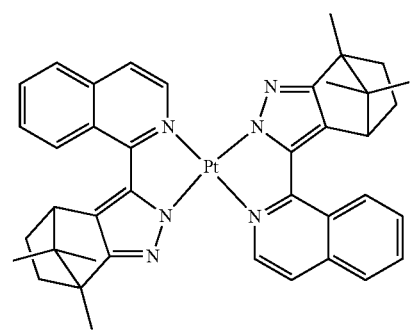

PD62 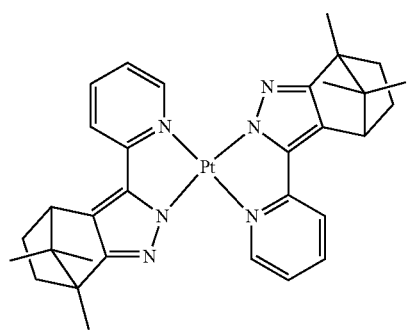
PD63 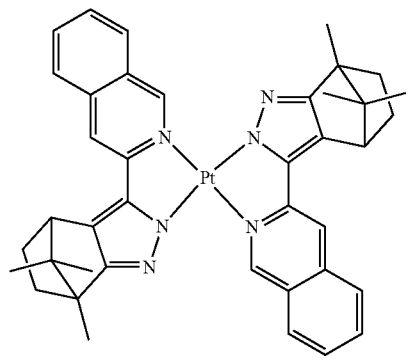
PD64 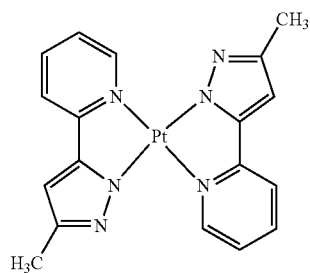
PD65 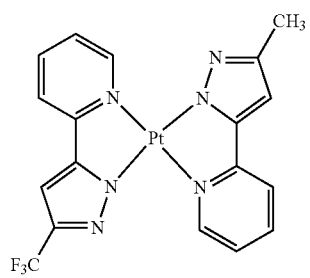
PD66 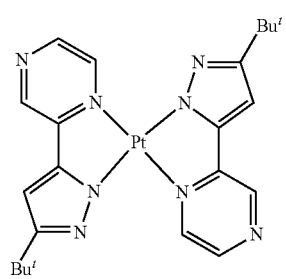
PD67 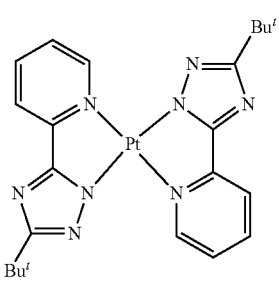
PD68 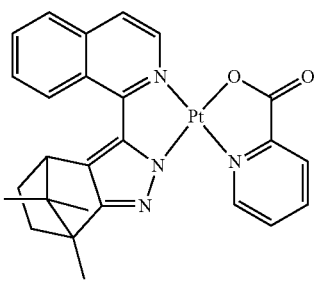
PD69 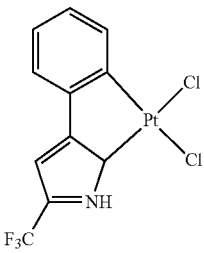
PD70 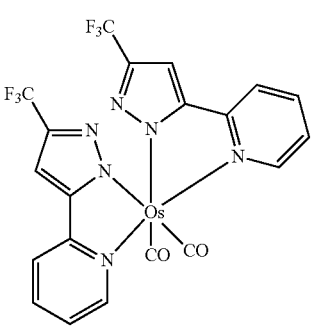
PD71 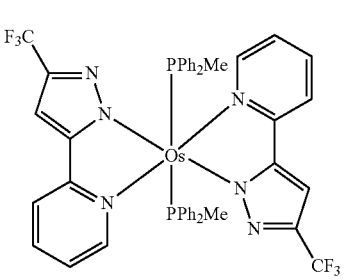

PD72
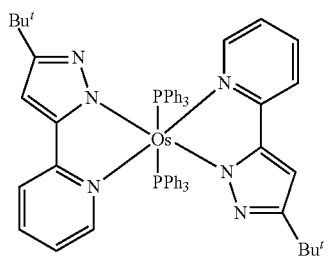
PD73
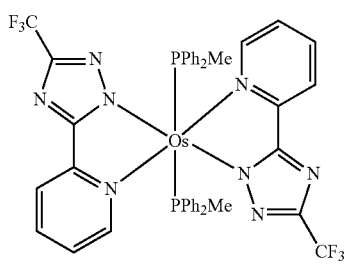
PD74
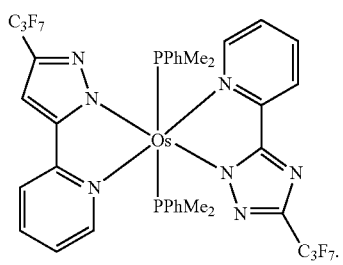
In some embodiments, the phosphorescent dopant may include PtOEP:
PtOEP
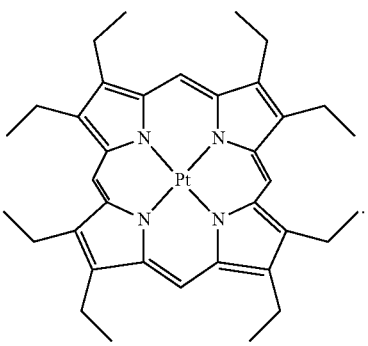
The fluorescent dopant may be or include at least one selected from DPVBi, DPAVBi, TBPe, DCM, DCJTB, Coumarin 6, and C545T:
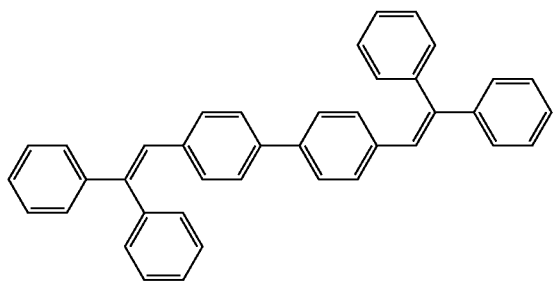
DPVBi
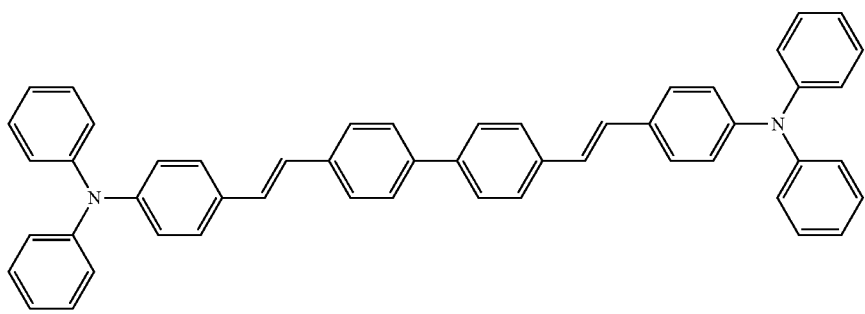
DPAVBi

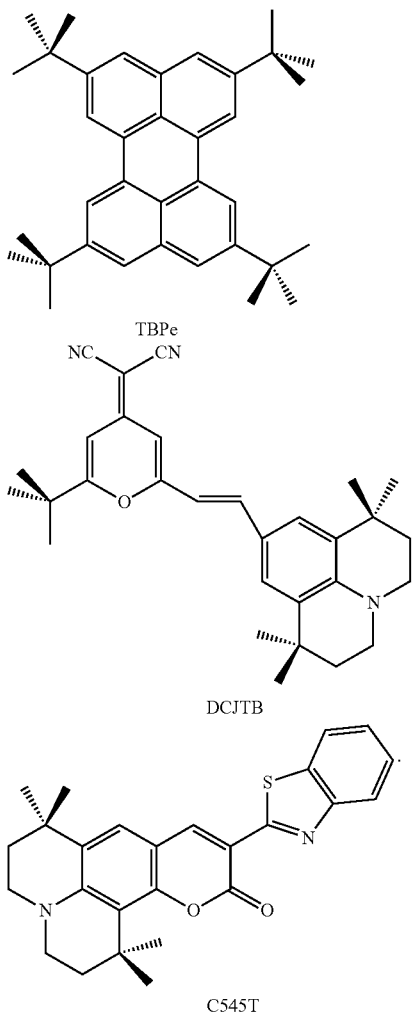

TBPe

DCJTB

C545T

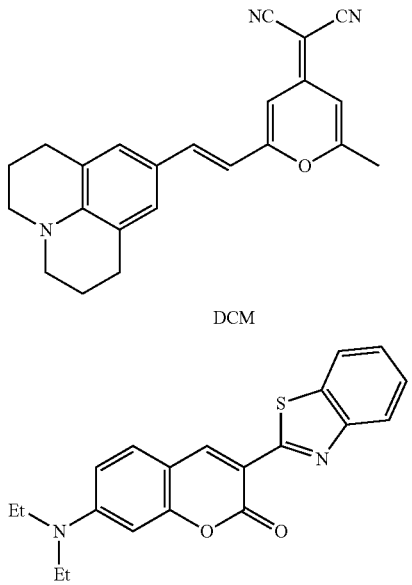

DCM

Coumarin 6

In some embodiments, the fluorescent dopant may include a compound represented by Formula 501.

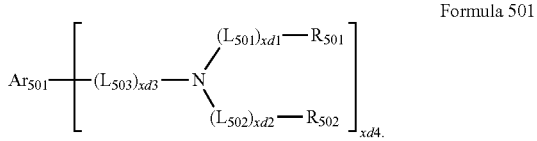

Formula 501

In Formula 501, $Ar_{501}$ may be selected from the group consisting of:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, monovalent non-aromatic condensed heteropolycyclic group, and —Si($Q_{501}$)($Q_{502}$)($Q_{503}$) (wherein $Q_{501}$ to $Q_{503}$ may each independently be selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

$L_{501}$ to $L_{503}$ may each be the same as described herein in connection with $L_{203}$;

$R_{501}$ and $R_{502}$ may each independently be selected from the group consisting of:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group; and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group;

xd1 to xd3 may each independently be selected from 0, 1, 2, and 3; and xd4 may be selected from 1, 2, 3, and 4.

The fluorescent dopant may be or include at least one selected from Compounds FD1 to FD8:

FD1

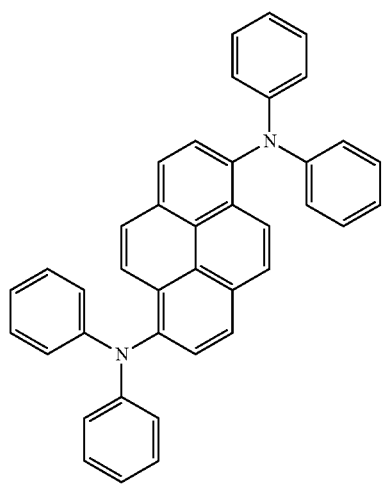

FD2

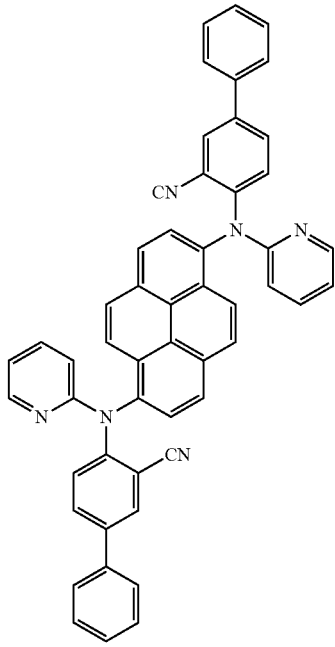

FD3

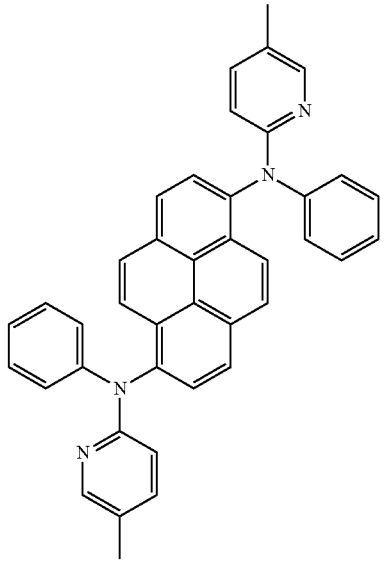

FD4

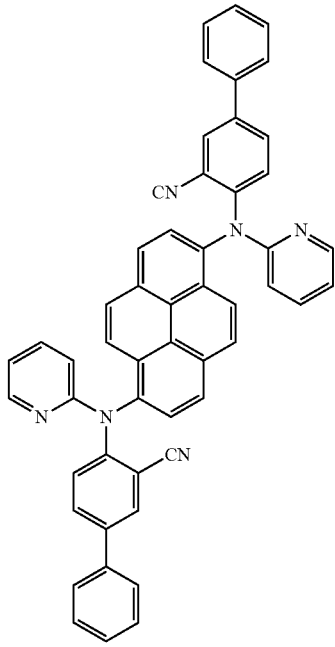

FD5

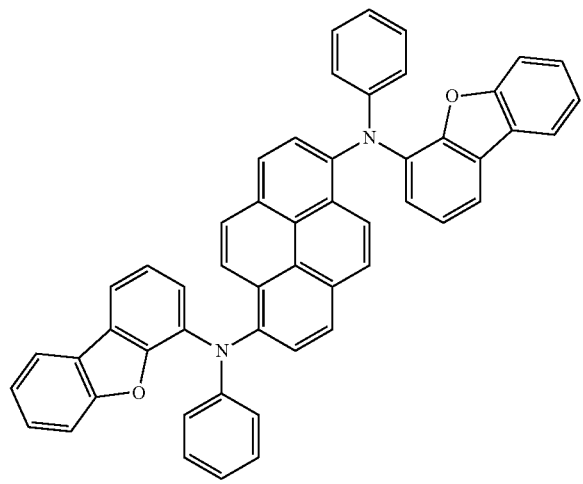

FD6

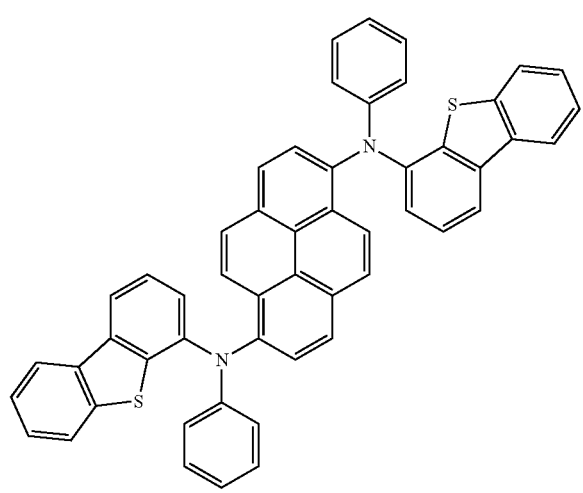

FD7

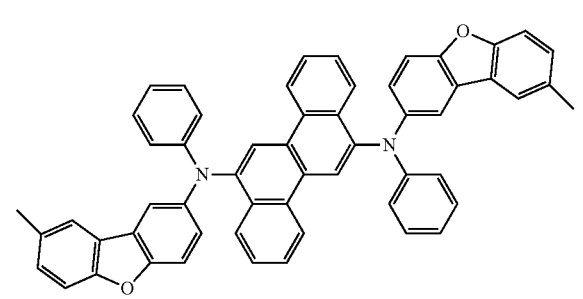

FD8

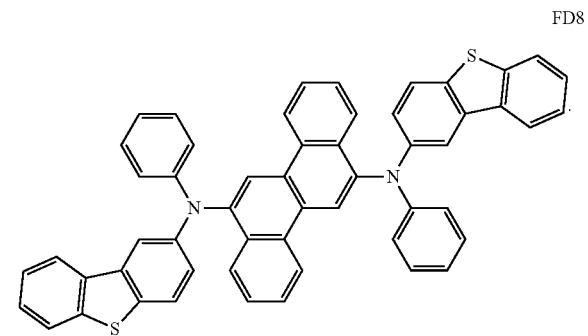

The amount of the dopant in the emission layer may be about 0.01 to about 15 parts by weight based on 100 parts by weight of the host, but embodiments of the present disclosure are not limited thereto.

The thickness of the emission layer may be about 100 Å to about 1,000 Å, and in some embodiments, about 200 Å to about 600 Å. When the thickness of the emission layer is within these ranges, excellent light-emission characteristics may be obtained without a substantial increase in driving voltage.

An electron transport region may be on the emission layer.

The electron transport region may include at least one selected from a hole blocking layer, an electron transport layer (ETL), and an electron injection layer, but embodiments of the present disclosure are not limited thereto.

In some embodiments, the electron transport region may include the compound represented by Formula 1 according to an embodiment of the present disclosure.

When the electron transport region includes a hole blocking layer, the hole blocking layer may be formed on the emission layer using one or more suitable methods selected from vacuum deposition, spin coating, casting, a Langmuir-Blodgett (LB) method, ink-jet printing, laser-printing, and/or laser-induced thermal imaging. When the hole blocking layer is formed by vacuum deposition and/or spin coating, the deposition and coating conditions used for the hole blocking layer may be similar to the deposition and coating conditions used for the hole injection layer.

The hole blocking layer may include, for example, at least one selected from BCP and Bphen, but embodiments of the present disclosure are not limited thereto:

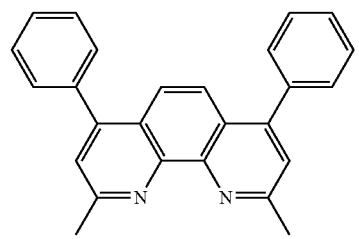

BCP

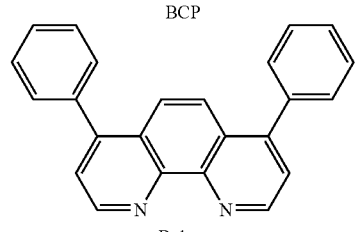

Bphen

The thickness of the hole blocking layer may be about 20 Å to about 1,000 Å, and in some embodiments, about 30 Å to about 300 Å. When the thickness of the hole blocking layer is within these ranges, the hole blocking layer may have excellent hole blocking characteristics without a substantial increase in driving voltage.

The electron transport region may be between the emission layer and the second electrode, and may include an electron transport layer and at least one layer selected from a hole blocking layer and an electron injection layer.

For example, the electron transport region may have a structure of electron transport layer/electron injection layer or a structure of hole blocking layer/electron transport layer/electron injection layer, wherein layers of each structure are sequentially stacked from the emission layer in each stated order, but embodiments of the structure thereof are not limited thereto.

According to an embodiment of the present disclosure, the organic layer 150 of the organic light-emitting device may include an electron transport region between the emission layer and the second electrode 190, and the electron transport region may include an electron transport layer. The electron transport layer may include a plurality of layers. For example, the electron transport layer may include a first electron transport layer and a second electron transport layer.

The electron transport layer may include the compound represented by Formula 1 according to an embodiment of the present disclosure.

The thickness of the electron transport layer may be about 100 Å to about 1,000 Å, and in some embodiments, about 150 Å to about 500 Å. When the thickness of the electron transport layer is within these ranges, the electron transport layer may exhibit satisfactory electron transport characteristics without a substantial increase in driving voltage.

The electron transport layer may further include, in addition to the materials described above, a metal-containing material.

The metal-containing material may include a Li complex. The Li complex may include, for example, Compound ET-D1 (lithium quinolate, LiQ) and/or ET-D2:

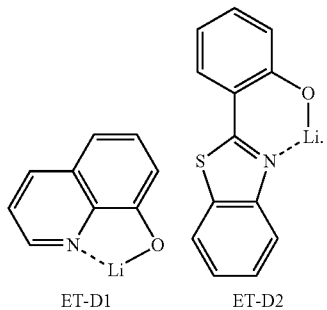

ET-D1      ET-D2

The electron transport region may include an electron injection layer that facilitates injection of electrons from the second electrode 190.

The electron injection layer may be formed on the electron transport layer using one or more methods selected from vacuum deposition, spin coating, casting, a LB method, ink-jet printing, laser-printing, and laser-induced thermal imaging. When an electron injection layer is formed by vacuum deposition and/or spin coating, the deposition and coating conditions used for the electron injection layer may be similar to those used for the hole injection layer.

The electron injection layer may include at least one selected from LiF, NaCl, CsF, $Li_2O$, BaO, and LiQ.

The thickness of the electron injection layer may be about 1 Å to about 100 Å, and in some embodiments, about 3 Å to about 90 Å. When the thickness of the electron injection layer is within these ranges, the electron injection layer may exhibit satisfactory electron injection characteristics without a substantial increase in driving voltage.

The second electrode 190 may be on the organic layer 150. The second electrode 190 may be a cathode, which is an electron injection electrode, and in this regard, the material for forming the second electrode 190 may be selected from a metal, an alloy, an electrically conductive compound, and mixtures thereof, each having a relatively low work function. Non-limiting examples of the second electrode 190 may include lithium (Li), magnesium (Mg), aluminum (Al), aluminum-lithium (Al—Li), calcium (Ca), magnesium-indium (Mg—In), and magnesium-silver (Mg—Ag). In some embodiments, the material for forming the second electrode 190 may be selected from ITO and IZO. The second electrode 190 may be a reflective electrode, a semi-transmissive electrode, or a transmissive electrode.

An organic layer according to an embodiment of the present disclosure may be formed by depositing the compound according to an embodiment of the present disclosure, or may be formed using a wet method, in which the compound according to an embodiment of the present disclosure is prepared in the form of a solution and the solution of the compound is used for coating.

An organic light-emitting device according to an embodiment of the present disclosure may be used in various flat panel display apparatuses (such as a passive matrix organic light-emitting display apparatus and/or an active matrix organic light-emitting display apparatus). For example, when the organic light-emitting device is included in an active matrix organic light-emitting display apparatus, a first electrode on a substrate acts as a pixel and may be electrically connected to a source electrode or a drain electrode of a thin film transistor. In some embodiments, the organic light-emitting device may be included in a flat panel display apparatus that emits light in opposite directions.

Hereinbefore, the organic light-emitting device has been described with reference to the drawing, but embodiments of the present disclosure are not limited thereto.

Hereinafter, definitions of compound substituents used herein will be presented. The number of carbon atoms used to restrict a substituent is not limited, and does not limit the properties of the substituent. Unless defined otherwise, the definition of the substituent is consistent with the general definition thereof.

The term "$C_1$-$C_{60}$ alkyl group" as used herein refers to a linear or branched aliphatic hydrocarbon monovalent group having 1 to 60 carbon atoms, and non-limiting examples thereof may include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group" as used herein refers to a divalent group having substantially the same structure as the $C_1$-$C_{60}$ alkyl group.

The term "$C_1$-$C_{60}$ alkoxy group" as used herein refers to a monovalent group represented by —O-$A_{101}$ (wherein $A_{101}$ is a $C_1$-$C_{60}$ alkyl group), and non-limiting examples thereof may include a methoxy group, an ethoxy group, and an isopropyloxy group.

The term "$C_2$-$C_{60}$ alkenyl group" as used herein refers to a hydrocarbon group having at least one carbon-carbon double bond in the body (e.g., middle) or at the terminus of the $C_2$-$C_{60}$ alkyl group, and non-limiting examples thereof may include an ethenyl group, a propenyl group, and a butenyl group. The term "$C_2$-$C_{60}$ alkenylene group" as used herein refers to a divalent group having substantially the same structure as the $C_2$-$C_{60}$ alkenyl group.

The term "$C_2$-$C_{60}$ alkynyl group" as used herein refers to a hydrocarbon group having at least one carbon-carbon triple bond in the body (e.g., middle) or at the terminus of the $C_2$-$C_{60}$ alkyl group, and non-limiting examples thereof may include an ethynyl group and a propynyl group. The term "$C_2$-$C_{60}$ alkynylene group" as used herein refers to a divalent group having substantially the same structure as the $C_2$-$C_{60}$ alkynyl group.

The term "$C_3$-$C_{10}$ cycloalkyl group" as used herein refers to a monovalent hydrocarbon monocyclic group having 3 to 10 carbon atoms, and non-limiting examples thereof may include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having substantially the same structure as the $C_3$-$C_{10}$ cycloalkyl group.

The term "$C_1$-$C_{10}$ heterocycloalkyl group" as used herein refers to a monovalent monocyclic group having at least one heteroatom selected from N, O, phosphorus (P), and sulfur (S) as a ring-forming atom in addition to 1 to 10 carbon atoms, and non-limiting examples thereof may include a tetrahydrofuranyl group and a tetrahydrothiophenyl group. The term "$C_1$-$C_{10}$ heterocycloalkylene group" as used herein refers to a divalent group having substantially the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one double bond in the ring thereof, and does not have aromaticity (e.g., is not aromatic), and non-limiting examples thereof may include a cyclopentenyl group, a cyclohexenyl group, and a cycloheptenyl group. The term "$C_3$-$C_{10}$ cycloalkenylene group" as used herein refers to a divalent group having substantially the same structure as the $C_3$-$C_{10}$ cycloalkenyl group.

The term "$C_2$-$C_{10}$ heterocycloalkenyl group" as used herein refers to a monovalent monocyclic group that has at least one heteroatom selected from N, O, P, and S as a ring-forming atom, 2 to 10 carbon atoms, and at least one double bond in its ring. Non-limiting examples of the $C_2$-$C_{10}$ heterocycloalkenyl group may include a 2,3-hydrofuranyl group and a 2,3-hydrothiophenyl group. The term "$C_2$-$C_{10}$ heterocycloalkenylene group" as used herein refers to a divalent group having substantially the same structure as the $C_2$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group may include a phenyl group, a biphenyl group, a terphenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused (e.g., condensed).

The term "$C_1$-$C_{60}$ heteroaryl group" as used herein refers to a monovalent group having a carbocyclic aromatic system that has at least one heteroatom selected from N, O, P, and S as a ring-forming atom, in addition to 1 to 60 carbon atoms. The term "$C_1$-$C_{60}$ heteroarylene group" as used herein refers to a divalent group having a carbocyclic aromatic system that has at least one heteroatom selected from N, O, P, and S as a ring-forming atom, in addition to 1 to 60 carbon atoms. Non-limiting examples of the $C_1$-$C_{60}$ heteroaryl group may include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused (e.g., condensed).

The term "$C_6$-$C_{60}$ aryloxy group" as used herein indicates —O-$A_{102}$ (wherein $A_{102}$ is a $C_6$-$C_{60}$ aryl group), and the term "$C_6$-$C_{60}$ arylthio group" as used herein indicates —S-$A_{103}$ (wherein $A_{103}$ is a $C_6$-$C_{60}$ aryl group).

The term "monovalent non-aromatic condensed polycyclic group" as used herein refers to a monovalent group that has two or more rings condensed (e.g., fused), only carbon atoms as ring forming atoms (for example, 8 to 60 carbon atoms), and non-aromaticity in the entire molecular structure (e.g., the entire structure is not aromatic). Non-limiting examples of the monovalent non-aromatic condensed polycyclic group may include a fluorenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group that has two or more rings condensed (e.g., fused), a heteroatom selected from N, O, P, and S in addition to carbon atoms (for example, 2 to 60 carbon atoms) as ring forming atoms, and non-aromaticity in the entire molecular structure (e.g., the entire structure is not aromatic). Non-limiting examples of the monovalent non-aromatic condensed heteropolycyclic group may include a carbazolyl group. The term "divalent non-aromatic condensed heteropolycyclic group" as used herein refers to a divalent group having substantially the same structure as the monovalent non-aromatic condensed heteropolycyclic group.

In the present specification, at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from the group consisting of:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a C₃-C₁₀ cycloalkyl group, a C₂-C₁₀ heterocycloalkyl group, a C₃-C₁₀ cycloalkenyl group, a C₂-C₁₀ heterocycloalkenyl group, a C₆-C₆₀ aryl group, a C₆-C₆₀ aryloxy group, a C₆-C₆₀ arylthio group, a C₁-C₆₀ heteroaryl group, a monovalent non-aromatic condensed polycyclic group, and a monovalent non-aromatic condensed heteropolycyclic group;

a C₃-C₁₀ cycloalkyl group, a C₂-C₁₀ heterocycloalkyl group, a C₃-C₁₀ cycloalkenyl group, a C₂-C₁₀ heterocycloalkenyl group, a C₆-C₆₀ aryl group, a C₆-C₆₀ aryloxy group, a C₆-C₆₀ arylthio group, a C₂-C₆₀ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_1$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$) and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from the group consisting of:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{11}$)($Q_{12}$), —Si($Q_{13}$)($Q_{14}$)($Q_{15}$), and —B($Q_{16}$)($Q_{17}$);

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

The expression "Ph" as used herein refers to a phenyl group, the expression "Me" as used herein refers to a methyl group, the expression "Et" as used herein refers to an ethyl group, and the expression "ter-Bu" or "Bu$^t$" as used herein refers to a tert-butyl group.

Hereinafter, an organic light-emitting device according to an embodiment of the present disclosure will be described in more detail with reference to Synthesis Examples and Examples.

SYNTHESIS EXAMPLE

Synthesis Example 1: Synthesis of Compound 5

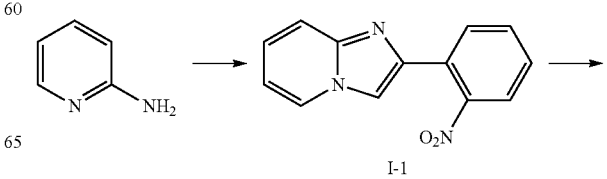

I-1

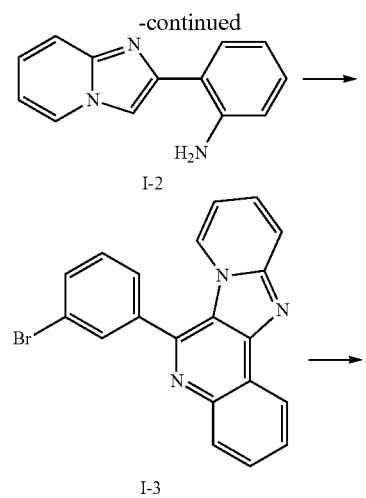

Synthesis of Intermediate I-1

2-aminopyridine (2.82 g, 30 mmol) and 2-bromo-1-(2-nitro-phenyl)-ethan-1-one (7.32 g, 30 mmol) were dissolved in ethanol (150 mL), and the mixture was stirred at a temperature of 90° C. for 12 hours. The reaction solution was cooled to room temperature, the solvent was evaporated therefrom, and the residue was neutralized using NaHCO₃ (aq). The reaction mixture was extracted three times using 60 mL of ethyl acetate, and the collected organic layer was dried using magnesium sulfate. The residual obtained by filtering the reaction and evaporating the solvent was purified by silica gel column chromatography, thereby completing the preparation of 4.31 g (yield: 60%) of Intermediate I-1. The obtained compound was identified by LC-MS.

$C_{13}H_9N_3O_2$: M+1=239.1

Synthesis of Intermediate I-2

Intermediate I-1 (4.31 g, 18 mmol), 6.37 g (54 mmol) of tin (Sn), and 10 mL (90 mmol, conc. 36.5%) of HCl were dissolved in 100 mL of ethanol, and the mixture was stirred at a temperature of 100° C. for 8 hours. The reaction solution was cooled to room temperature and filtered under reduced pressure, and 6 g of sodium hydroxide dissolved in 10 mL of water was added to the filtrate. The reaction mixture was extracted three times using 60 mL of water and 60 mL of dichloromethane, and the collected organic layer was dried using magnesium sulfate. The residual obtained by filtering the reaction and evaporating the solvent therefrom was purified by silica gel column chromatography to obtain 2.64 g (yield of 70%) of Intermediate I-2. The obtained compound was identified by LC-MS.

$C_{13}H_{11}N_3$: M+1=209.1

Synthesis of Intermediate I-3

Intermediate I-2 (2.64 g, 12.6 mmol), 3-bromo-benzaldehyde (2.33 g, 12.6 mmol), and p-TsOH (0.252 g, 1.26 mmol) were dissolved in 100 mL of toluene, and the mixture was stirred at a temperature of 100° C. for 8 hours. The reaction solution was cooled to room temperature, and extracted three times using 30 mL of water and 30 mL of ethyl acetate. The collected organic layer was dried using magnesium sulfate, and the residual obtained by filtering the reaction and evaporating the solvent therefrom was purified by silica gel column chromatography to obtain 3.58 g (yield of 76%) of Intermediate I-3. The obtained compound was identified by LC-MS. $C_{20}H_{12}BrN_3$: M+1=373.0

Synthesis of Compound 5

Intermediate I-3 (3.58 g, 9.58 mmol), 9,9-dimethyl-7-(4,4,5,5-tetramethyl-1,3,2-dioxaborolane-2-yl)-9H-fluorene-2-carbonitrile (3.31 g, 9.58 mmol), Pd(PPh₃)₄ (0.553 g, 0.48 mmol), and K₂CO₃ (3.97 g, 28.7 mmol) were dissolved in 60 mL of a mixed solution of THF/H₂O (volumetric ratio of 2:1), and the mixture was stirred at a temperature of 80° C. for 12 hours. The reaction solution was cooled to room temperature and extracted three times using 30 mL of water and 30 mL of ethyl acetate. The collected organic layer was dried using magnesium sulfate, and the residual obtained by filtering the reaction and evaporating the solvent therefrom was purified by silica gel column chromatography to obtain 3.43 g (yield of 70%) of Compound 5. The obtained compound was identified by MS-FAB and ¹H NMR.

$C_{36}H_{24}N_4$ calc. 512.20. found 512.22.

Synthesis Example 2: Synthesis of Compound 7

3.87 g (yield: 72%) of Compound 7 was obtained in substantially the same manner as Compound 5, except that 9-phenyl-6-(4,4,5,5-tetramethyl-1,3,2-dioxaborolane-2-yl)-9H-carbazole-2-carbonitrile was used instead of 9,9-dimethyl-7-(4,4,5,5-tetramethyl-1,3,2-dioxaborolane-2-yl)-9H-fluorene-2-carbonitrile. The obtained compound was identified by MS-FAB and ¹H NMR.

$C_{39}H_{23}N_5$ calc. 561.20. found 561.21.

Synthesis Example 3: Synthesis of Compound 8

3.90 g (yield: 68%) of Compound 8 was obtained in substantially the same manner as Compound 5, except that 4-bromo-benzaldehyde was used instead of 3-bromo-benzaldehyde in synthesizing Intermediate I-3, and 6-phenyl-8-(4,4,5,5-tetramethyl-1,3,2-dioxaborolane-2-yl)-benzo[k]phenanthridine was used instead of 9,9-dimethyl-7-(4,4,5,5-tetramethyl-1,3,2-dioxaborolane-2-yl)-9H-fluorene-2-carbonitrile in synthesizing Compound 5. The obtained compound was identified by MS-FAB and ¹H NMR.

$C_{43}H_{26}N_4$ calc. 598.22. found 598.21.

Synthesis Example 4: Synthesis of Compound 20

3.55 g (yield: 71%) of Compound 20 was obtained in substantially the same manner as Compound 5, except that 10-bromo-anthracene-9-carboaldehyde was used instead of 3-bromo-benzaldehyde in synthesizing Intermediate I-3, and naphthalene-1-yl-boronic acid was used instead of 9,9- dimethyl-7-(4,4,5,5-tetramethyl-1,3,2-dioxaborolane-2-yl)-9H-fluorene-2-carbonitrile in synthesizing Compound 5.
$C_{38}H_{23}N_3$ calc. 521.19. found 521.20.

Synthesis Example 5: Synthesis of Compound 26

4.63 g (yield: 73%) of Compound 26 was obtained in substantially the same manner as Compound 20, except that 9-phenyl-6-(4,4,5,5-tetramethyl-1,3,2-dioxaborolane-2-yl)-9H-carbazole-2-carbonitrile was used instead of naphthalene-1-yl-boronic acid.
$C_{38}H_{23}N_3$ calc. 661.23. found 661.22.

Synthesis Example 6: Synthesis of Compound 39

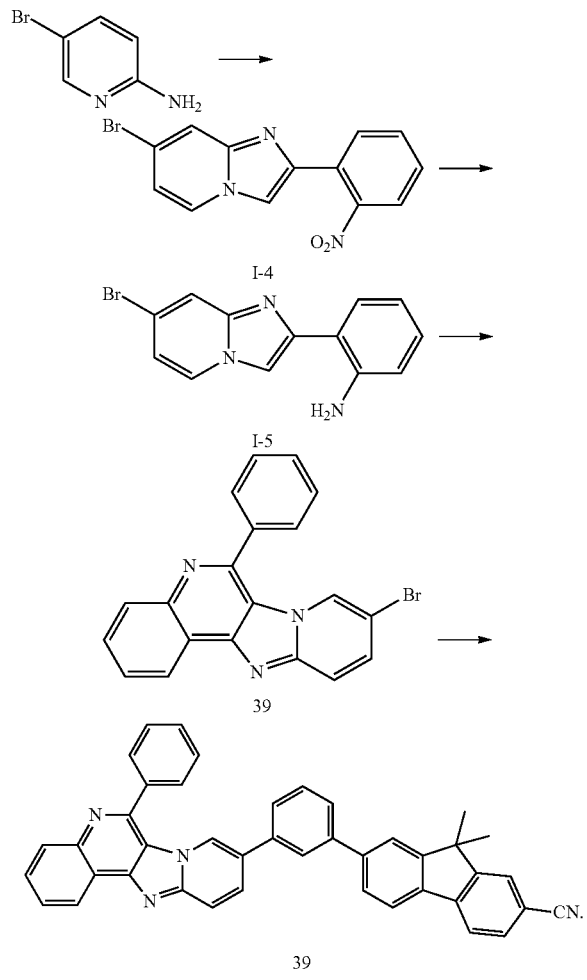

Synthesis of Intermediate I-4

6.68 g (yield: 70%) of Intermediate I-4 was prepared in substantially the same manner as Intermediate I-1, except that 5-bromopyridine-2-amine was used instead of 2-amino pyridine.
$C_{13}H_8BrN_3O_2$: M+1=317.0

Synthesis of Intermediate I-5

4.11 g (yield 68%) of Intermediate I-5 was obtained in substantially the same manner as Intermediate I-2, except that Intermediate I-4 was used instead of Intermediate I-1. The obtained compound was identified by LC-MS.
$C_{13}H_{10}BrN_3$: M+1=287.0

Synthesis of Intermediate I-6

4.06 g (yield: 76%) of Intermediate I-6 was prepared in substantially the same manner as Intermediate I-3, except that Intermediate I-5 was used instead of Intermediate I-2.
$C_{20}H_{12}BrN_3$: M+1=373.0

Synthesis of Compound 39

Intermediate I-6 (4.06 g, 10.85 mmol), 9,9-dimethyl-7-(3-(4,4,5,5-tetramethyl-1,3,2-dioxaborolane-2-yl)phenyl)-9H-fluorene-2-carbonitrile (4.57 g, 10.85 mmol), Pd(PPh$_3$)$_4$ (0.627 g, 0.543 mmol), and K$_2$CO$_3$ (4.50 g, 32.6 mmol) were dissolved in 60 mL of a mixed solution of THF/H$_2$O (volumetric ratio of 2:1), and the mixture was stirred at a temperature of 80° C. for 12 hours. The reaction solution was cooled to room temperature and extracted three times using 30 mL of water and 30 mL of ethyl acetate. The collected organic layer was dried using magnesium sulfate, and the residual obtained by filtering the reaction and evaporating the solvent therefrom was purified by silica gel column chromatography to obtain 4.60 g (yield of 72%) of Compound 39. The obtained compound was identified by MS-FAB and $^1$H NMR.
$C_{42}H_{28}N_4$ calc. 588.23. found 588.25.

Synthesis Example 7: Synthesis of Compound 44

4.72 g (yield: 70%) of Compound 44 was prepared in substantially the same manner as Compound 39, except that 2-(3-(dinaphtho[2,1-b:1',2'-d]furan-6-yl)phenyl)-4,4,5,5-tetramethyl-1,3,2-dioxaborolane was used instead of 9,9-dimethyl-7-(3-(4,4,5,5-tetramethyl-1,3,2-dioxaborolane-2-yl)phenyl)-9H-fluorene-2-carbonitrile. The obtained compound was identified by MS-FAB and $^1$H NMR.
$C_{46}H_{27}N_3O$ calc. 637.22. found 637.23.

Synthesis Example 8: Synthesis of Compound 45

4.76 g (yield: 65%) of Compound 45 was prepared in substantially the same manner as Compound 39, except that 6-phenyl-8(3-(4,4,5,5-tetramethyl-1,3,2-dioxaborolane-2-yl)benzo[k]phenanthridine was used instead of 9,9-dimethyl-7-(3-(4,4,5,5-tetramethyl-1,3,2-dioxaborolane-2-yl)phenyl)-9H-fluorene-2-carbonitrile. The obtained compound was identified by MS-FAB and $^1$H NMR.
$C_{49}H_{30}N_4$ calc. 674.25. found 674.26.

Synthesis Example 9: Synthesis of Compound 50

4.55 g (yield: 72%) of Compound 50 was prepared in substantially the same manner as Compound 39, except that 4,4,5,5-tetramethyl-2-(10-(naphthalene-2-yl)anthracene-9-yl)-1,3,2-dioxaborolane was used instead of 9,9-dimethyl-7-(3-(4,4,5,5-tetramethyl-1,3,2-dioxaborolane-2-yl)phenyl)-9H-fluorene-2-carbonitrile. The obtained compound was identified by MS-FAB and $^1$H NMR.
$C_{44}H_{27}N_3$ calc. 597.22. found 597.21.

Synthesis Example 10: Synthesis of Compound 57

4.72 g (yield: 70%) of Compound 57 was prepared in substantially the same manner as Compound 39, except that 2-(10-(dibenzo[b,d]-furan-4-yl)anthracene-9-yl)-4,4,5,5-tetramethyl-1,3,2-dioxaborolane was used instead of 9,9-dimethyl-7-(3-(4,4,5,5-tetramethyl-1,3,2-dioxaborolane-2-yl)phenyl)-9H-fluorene-2-carbonitrile. The obtained compound was identified by MS-FAB and $^1$H NMR.

$C_{46}H_{27}N_3O$ calc. 637.22. found 637.23.

Synthesis Example 11: Synthesis of Compound 71

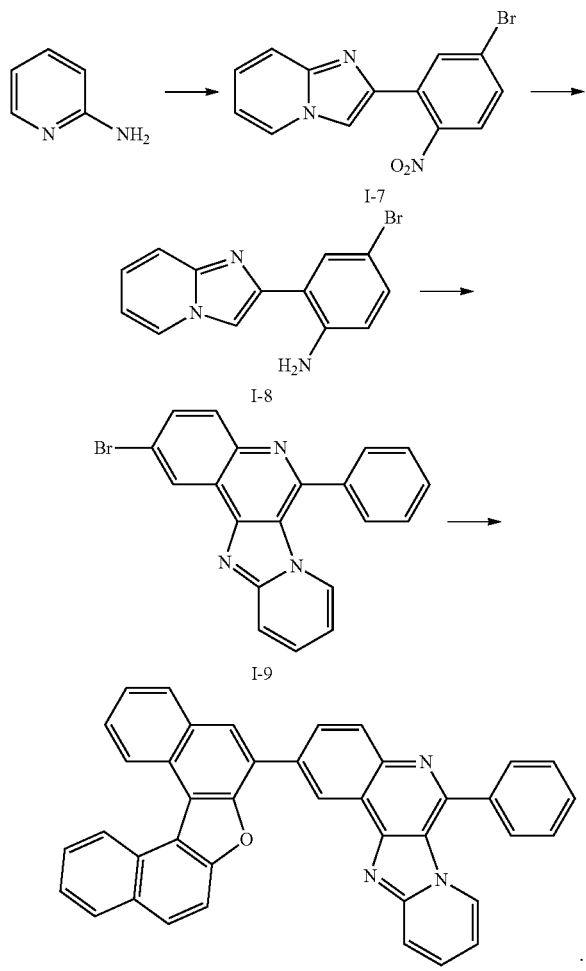

Synthesis of Intermediate I-7

6.68 g (yield: 70%) of Intermediate I-7 was prepared in substantially the same manner as Intermediate I-1, except that 2-bromo-1-(5-bromo-2-nitrophenyl)-ethan-1-one was used instead of 2-bromo-1-(2-nitro-phenyl)-ethan-1-one. The obtained compound was identified by LC-MS.

$C_{13}H_8BrN_3O_2$: M+1=317.0

Synthesis of Intermediate I-8

3.99 g (yield: 66%) of Intermediate I-8 was prepared in substantially the same manner as Intermediate I-2, except that Intermediate I-7 was used instead of Intermediate I-1. The obtained compound was identified by LC-MS.

$C_{13}H_{10}BrN_3$: M+1=287.0

Synthesis of Intermediate I-6

3.79 g (yield: 73%) of Intermediate I-6 was prepared in substantially the same manner as Intermediate I-3, except that Intermediate I-8 was used instead of Intermediate I-2. The obtained compound was identified by LC-MS.

$C_{20}H_{12}BrN_3$: M+1=373.0

Synthesis of Compound 71

Intermediate I-6 (3.79 g, 10.12 mmol), 2-(dinaphtho[2,1-b:1',2'-d]furan-6-yl)-4,4,5,5-tetramethyl-1,3,2-dioxaborolane (3.99 g, 10.12 mmol), Pd(PPh$_3$)$_4$ (0.585 g, 0.506 mmol), and K$_2$CO$_3$ (4.20 g, 30.36 mmol) were dissolved in 60 mL of a mixed solution of THF/H$_2$O (volumetric ratio of 2:1), and the mixture was stirred at a temperature of 80° C. for 12 hours. The reaction solution was cooled to room temperature and extracted three times using 30 mL of water and 30 mL of ethyl acetate. The collected organic layer was dried using magnesium sulfate, and the residual obtained by filtering the reaction and evaporating the solvent therefrom was purified by silica gel column chromatography to obtain 4.43 g (yield of 78%) of Compound 71. The obtained compound was identified by MS-FAB and $^1$H NMR.

$C_{40}H_{23}N_3O$ calc. 561.18. found 561.17.

Synthesis Example 12: Synthesis of Compound 90

4.18 g (yield: 66%) of Compound 90 was prepared in substantially the same manner as Compound 71, except that 6-(10-(4,4,5,5-tetramethyl-1,3,2-dioxaborolane-2-yl)anthracene-9-yl)-2,4'-bipyridine was used instead of 2-(dinaphtho[2,1-b:1',2'-d]furan-6-yl)-4,4,5,5-tetramethyl-1,3,2-dioxabororene. The obtained compound was identified by MS-FAB and $^1$H NMR.

$C_{44}H_{27}N_5$ calc. 625.23. found 625.22.

Additional compounds were synthesized using the same synthesis method as described above with appropriate or suitable intermediate materials, and $^1$H NMR and MS-FAB results for each of the synthetic compounds are shown in Table 1.

Methods of synthesizing compounds other than the compound shown in Table 1 may be easily recognized by one of ordinary skill in the art by referring to the synthetic pathways and source materials described above.

TABLE 1

| Compound | $^1$H NMR (CDCl$_3$, 400 MHz) δ | MS-FAB found | calc. |
|---|---|---|---|
| 5 | δ = 8.76 (d, 1H), 8.65 (d, 1H), 8.50 (t, 1H), 8.20-8.15 (m, 2H), 8.00-7.96 (m, 1H), 7.90-7.79 (m, 4H), 7.69-7.65 (m, 3H), 7.60-7.56 (m, 1H), 7.51-7.45 (m, 3H), 7.06 (t, 1H), 1.82 (s, 6H) | 512.22 | 512.20 |
| 7 | δ = 8.77-8.76 (m, 2H), 8.65 (d, 1H), 8.23-8.07 (m, 4H), 8.03-7.79 (m, 6H), 7.70-7.49 (m, 7H), 7.40 (t, 1H), 7.32-7.28 (m, 1H), 7.06 (t, 1H) | 561.21 | 561.20 |

TABLE 1-continued

| Compound | $^1$H NMR (CDCl$_3$, 400 MHz) δ | MS-FAB found | MS-FAB calc. |
|---|---|---|---|
| 8 | δ = 8.78-8.75 (m, 2H), 8.67 (d, 1H), 8.37-8.33 (m, 3H), 8.27-8.25 (m, 1H), 8.17-8.11 (m, 2H), 8.00-7.92 (m, 5H), 7.86-7.56 (m, 10H), 7.15 (t, 1H), 7.06 (t, 1H) | 598.21 | 598.22 |
| 20 | δ = 8.84-8.81 (m, 2H), 8.19 (d, 1H), 8.05-7.99 (m, 3H), 7.92-7.90 (m, 1H), 7.86-7.79 (m, 3H), 7.72-7.69 (m, 2H), 7.60-7.34 (m, 7H), 7.23-7.19 (m, 2H), 7.11 (t, 1H), 6.96 (t, 1H) | 521.20 | 521.19 |
| 26 | δ = 8.83-8.80 (m, 2H), 8.52 (d, 2H), 8.26-8.18 (m, 2H), 8.09 (d, 1H), 8.05-8.01 (m, 3H), 7.92-7.79 (m, 4H), 7.63-7.49 (m, 9H), 7.32-7.28 (m, 3H), 7.11 (t, 1H) | 661.22 | 661.23 |
| 39 | δ = 9.57 (d, 1H), 8.87-8.78 (m, 3H), 8.16 (d, 1H), 8.00-7.92 (m, 2H), 7.81-7.65 (m, 5H), 7.56-7.37 (m, 8H), 7.28-7.26 (m, 1H), 7.18 (t, 1H), 1.85 (s, 6H) | 588.25 | 588.23 |
| 44 | δ = 9.56 (d, 1H), 8.85-8.76 (m, 5H), 8.35-8.30 (m, 2H), 8.16 (d, 1H), 8.00-7.91 (m, 5H), 7.83-7.79 (m, 2H), 7.72-7.47 (m, 11H) | 637.23 | 637.22 |
| 45 | δ = 9.55 (d, 1H), 8.83-8.72 (m, 4H), 8.33-8.11 (m, 5H), 8.00-7.92 (m, 4H), 7.86-7.45 (m, 13H), 7.35-7.29 (m, 2H), 7.17 (t, 1H) | 674.26 | 674.25 |
| 50 | δ = 9.91 (d, 1H), 8.87-8.78 (m, 3H), 8.16 (d, 1H), 8.04-7.91 (m, 10H), 7.83-7.80 (m, 3H), 7.61-7.47 (m, 5H), 7.37-7.33 (m, 4H) | 597.21 | 597.22 |
| 57 | δ = 9..92 (d, 1H), 8.88-8.79 (m, 3H), 8.19 (d, 1H), 8.10-7.90 (m, 10H), 7.81 (t, 1H), 7.66 (d, 1H), 7.56-7.49 (m, 4H), 7.41-7.26 (m, 6H) | 637.23 | 637.22 |
| 71 | δ = 9.05 (d, 1H), 8.85-8.80 (m, 4H), 8.70 (d, 2H), 8.49 (s, 1H), 8.15 (d, 1H), 7.95-7.87 (m, 4H), 7.71 (d, 1H), 7.63-7.45 (m, 8H), 7.06 (t, 1H) | 561.17 | 561.18 |
| 90 | δ = 9.30 (d, 1H), 8.87-8.85 (m, 2H), 8.65-8.57 (m, 4H), 8.04-7.76 (m, 9H), 7.60-7.37 (m, 8H), 7.27-7.23 (m, 2H), 7.06 (t, 1H) | 625.22 | 625.23 |

Example 1

An anode was prepared by cutting a Corning 15 Ω/cm$^2$ (1,200 Å) ITO glass substrate to a size of 50 mm×50 mm×0.7 mm, sonicating the glass substrate using isopropyl alcohol and pure water for 5 minutes each, irradiating with UV light for 30 minutes, and exposing the substrate to ozone. The anode was loaded onto a vacuum deposition apparatus.

2-TNATA was vacuum deposited thereon to form a hole injection layer having a thickness of 600 Å, and 4,4'-bis[N-(1-naphthyl)-N-phenylamino]biphenyl (NPB) was deposited on the hole injection layer to form a hole transport layer having a thickness of 300 Å.

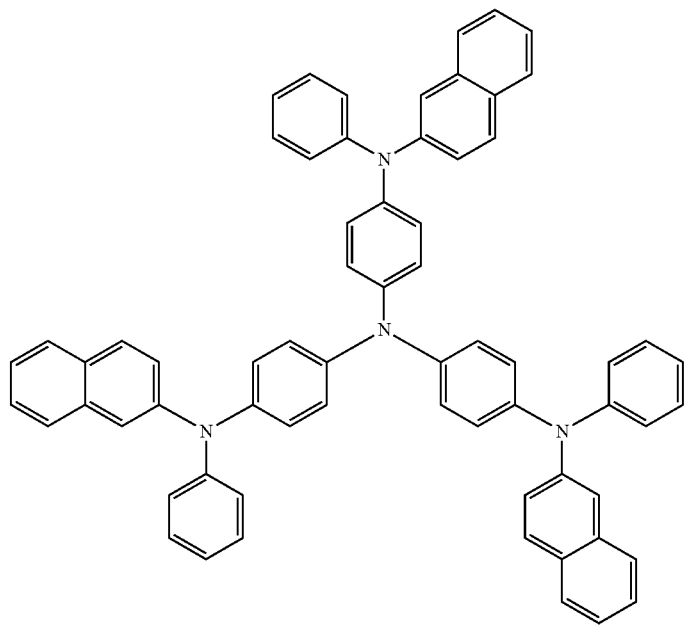

2-TNATA

-continued

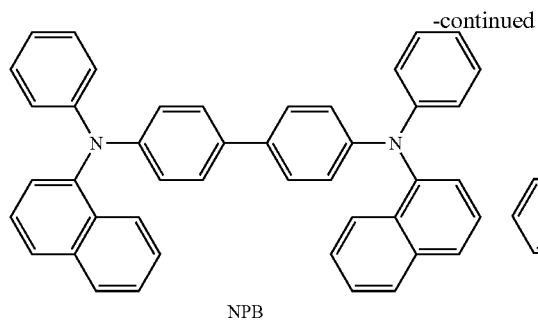

NPB

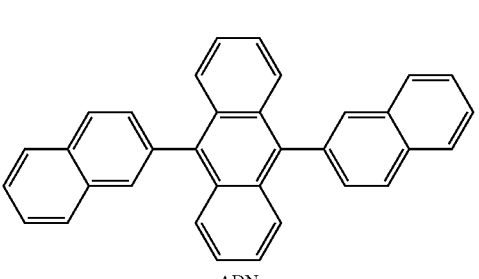

ADN

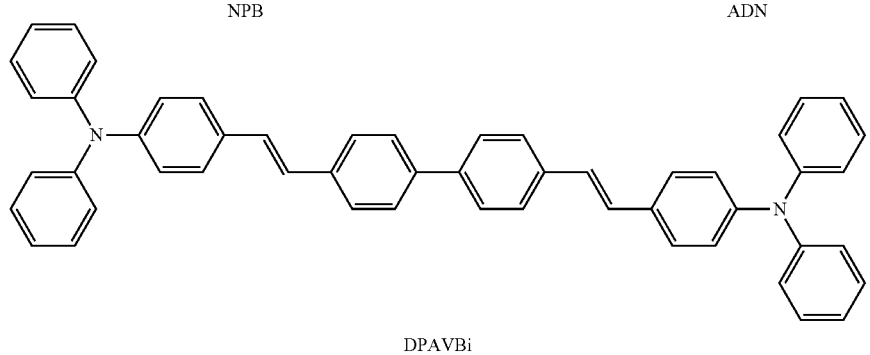

DPAVBi 9,10-di-naphthalene-2-yl-anthracene (ADN), which is a blue fluorescent host, and 4,4'-bis[2-(4-(N,N-diphenylamino)phenyl)vinyl]biphenyl (DPAVBi), which is a blue fluorescent dopant, were co-deposited on the hole transport layer at a weight ratio of 98:2 to form an emission layer having a thickness of 300 Å.

Compound 5 was deposited on the emission layer to form an electron transport layer having a thickness of 300 Å, LiF (which is a halogenated alkali metal) was deposited on the electron transport layer to form an electron injection layer having a thickness of 10 Å, and Al was vacuum deposited thereon to a thickness of 3,000 Å to form a cathode, thereby forming an LiF/Al electrode and completing the manufacturing of an organic light-emitting device.

Example 2

An organic light-emitting device was manufactured in substantially the same manner as in Example 1, except that Compound 7 was used instead of Compound 5 in forming the electron transport layer.

Example 3

An organic light-emitting device was manufactured in substantially the same manner as in Example 1, except that Compound 8 was used instead of Compound 5 in forming the electron transport layer.

Example 4

An organic light-emitting device was manufactured in substantially the same manner as in Example 1, except that Compound 20 was used instead of Compound 5 in forming the electron transport layer.

Example 5

An organic light-emitting device was manufactured in substantially the same manner as in Example 1, except that Compound 26 was used instead of Compound 5 in forming the electron transport layer.

Example 6

An organic light-emitting device was manufactured in substantially the same manner as in Example 1, except that Compound 39 was used instead of Compound 5 in forming the electron transport layer.

Example 7

An organic light-emitting device was manufactured in substantially the same manner as in Example 1, except that Compound 44 was used instead of Compound 5 in forming the electron transport layer.

Example 8

An organic light-emitting device was manufactured in substantially the same manner as in Example 1, except that Compound 45 was used instead of Compound 5 in forming the electron transport layer.

Example 9

An organic light-emitting device was manufactured in substantially the same manner as in Example 1, except that Compound 50 was used instead of Compound 5 in forming the electron transport layer.

Example 10

An organic light-emitting device was manufactured in substantially the same manner as in Example 1, except that Compound 57 was used instead of Compound 5 in forming the electron transport layer.

Example 11

An organic light-emitting device was manufactured in substantially the same manner as in Example 1, except that Compound 71 was used instead of Compound 5 in forming the electron transport layer.

Example 12

An organic light-emitting device was manufactured in substantially the same manner as in Example 1, except that Compound 90 was used instead of Compound 5 in forming the electron transport layer.

Comparative Example 1

An organic light-emitting device was manufactured in substantially the same manner as in Example 1, except that Compound 200 was used instead of Compound 5 in forming the electron transport layer:

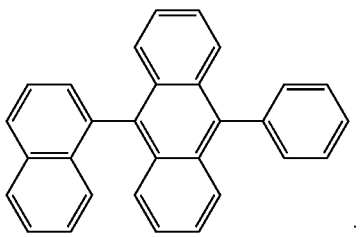

The driving voltage, luminance, and efficiency of each of the Comparative Examples and Examples at a current density of 50 mA/cm² are shown in Table 2, along with the half lifespan at a current density of 100 mA/cm².

TABLE 2

| | Material | Driving voltage (V) | Current density (mA/cm²) | Luminance (cd/m²) | Efficiency (cd/A) | Emission color | Half lifespan (hr @100 mA/cm²) |
|---|---|---|---|---|---|---|---|
| Example 1 | Compound 5 | 3.70 | 50 | 3,405 | 7.33 | blue | 615 hr |
| Example 2 | Compound 7 | 3.52 | 50 | 3,775 | 8.06 | blue | 630 hr |
| Example 3 | Compound 8 | 3.57 | 50 | 3,520 | 7.62 | blue | 660 hr |
| Example 4 | Compound 20 | 3.43 | 50 | 3,630 | 8.10 | blue | 607 hr |
| Example 5 | Compound 26 | 3.37 | 50 | 3,860 | 8.25 | blue | 652 hr |
| Example 6 | Compound 39 | 3.32 | 50 | 3,560 | 7.76 | blue | 630 hr |
| Example 7 | Compound 44 | 3.45 | 50 | 3,750 | 8.02 | blue | 637 hr |
| Example 8 | Compound 45 | 3.51 | 50 | 3,565 | 7.57 | blue | 665 hr |
| Example 9 | Compound 50 | 3.46 | 50 | 3,610 | 8.06 | blue | 628 hr |
| Example 10 | Compound 57 | 3.53 | 50 | 3,825 | 8.12 | blue | 643 hr |
| Example 11 | Compound 71 | 3.60 | 50 | 3,690 | 8.16 | blue | 675 hr |
| Example 12 | Compound 90 | 3.39 | 50 | 3,795 | 8.26 | blue | 660 hr |
| Comparative Example 1 | Compound 200 | 5.06 | 50 | 3,010 | 6.52 | blue | 325 hr |

When compounds represented by Formula 1 were used as electron transport materials, excellent I-V-L characteristics were obtained. For example, compared to Comparative Example 1, the driving voltage of each Example was decreased by 1 V or more, and the efficiency of each was substantially improved. The Example devices also exhibited longer lifespans. Accordingly, it is seen that compounds represented by Formula 1 according to an embodiment of the present disclosure are suitable for use as electron transport materials.

An organic light-emitting device according to an embodiment of the present disclosure may have high efficiency, low voltage, high luminance, and long lifespan.

It should be understood that the embodiments described herein should be considered in a descriptive sense only and not for purposes of limitation. Descriptions of features or aspects within each embodiment should typically be considered as being available for other similar features or aspects in other embodiments.

The use of "may" when describing embodiments of the present disclosure refers to "one or more embodiments of the present disclosure". In addition, as used herein, the terms "use", "using", and "used" may be considered synonymous with the terms "utilize", "utilizing", and "utilized", respectively.

As used herein, the terms "substantially", "about", and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

While one or more embodiments have been described with reference to the drawing, it will be understood by those of ordinary skill in the art that various changes in form and details may be made therein without departing from the spirit and scope of the present disclosure, as defined by the following claims and equivalents thereof.

What is claimed is:

1. A compound represented by Formula 1:

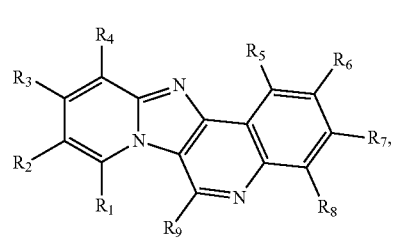

Formula 1 wherein, in Formula 1, $R_1$, $R_3$, $R_4$, $R_5$, $R_7$, and $R_8$ in Formula 1 are each independently selected from hydrogen and deuterium;

$R_2$ and $R_6$ in Formula 1 are each independently selected from hydrogen, deuterium, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group; and $R_9$ is represented by one selected from Formulae 2b to 2e:

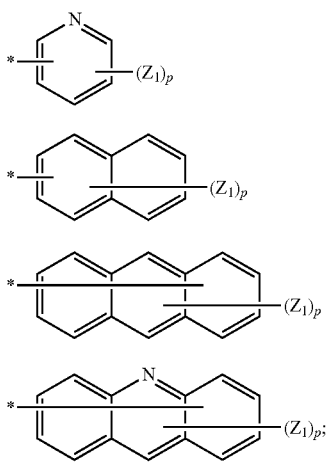

wherein, in Formulae 2b to 2e, $Z_1$ is selected from hydrogen, deuterium, a halogen atom, a cyano group, a nitro group, a hydroxyl group, a carboxyl group, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group;

when the number of $Z_1$ groups is 2 or more, a plurality of $Z_1$ groups are identical to or different from each other;

p is an integer selected from 1 to 9; and

* indicates a binding site.

2. The compound of claim 1, wherein:

$R_2$ in Formula 1 is represented by one selected from Formulae 4a to 4e:

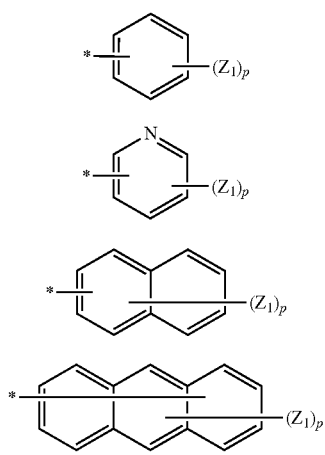
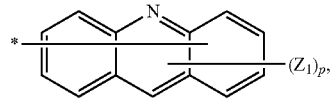

wherein, in Formulae 4a to 4e, $Z_1$ is selected from hydrogen, deuterium, a halogen atom, a cyano group, a nitro group, a hydroxyl group, a carboxyl group, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group;

when the number of $Z_1$ groups is 2 or more, a plurality of $Z_1$ groups are identical to or different from each other;

p is an integer selected from 1 to 9; and

* indicates a binding site.

3. The compound of claim 1, wherein:

$R_6$ in Formula 1 is represented by one selected from Formulae 3a to 3g:

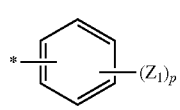
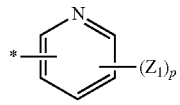
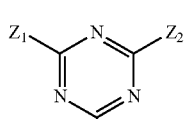
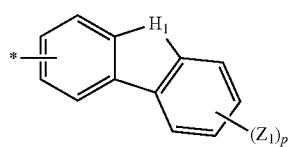
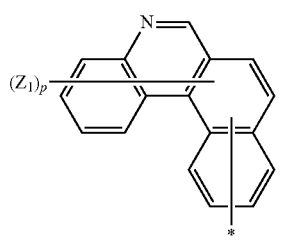
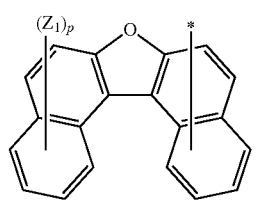

3g

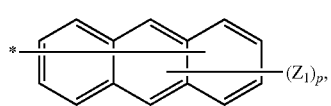

wherein, in Formulae 3a to 3g, $H_1$ is selected from $CR_{11}R_{12}$, $NR_{13}$, O, and S, $R_{11}$ to $R_{13}$, $Z_1$, and $Z_2$ are each independently selected from hydrogen, deuterium, a halogen atom, a cyano group, a nitro group, a hydroxyl group, a carboxyl group, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group;

when the number of $Z_1$ groups is 2 or more, a plurality of $Z_1$ groups are identical to or different from each other;

p is an integer selected from 1 to 9; and

* indicates a binding site.

4. The compound of claim 1, wherein the compound represented by Formula 1 is represented by Formula 2:

Formula 2

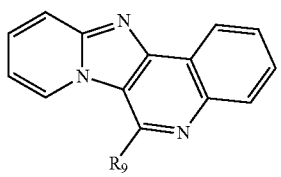

wherein $R_9$ is the same as described in Formula 1.

5. The compound of claim 1, wherein the compound represented by Formula 1 is represented by one selected from Compounds 2, 3, and 18 to 36:

2

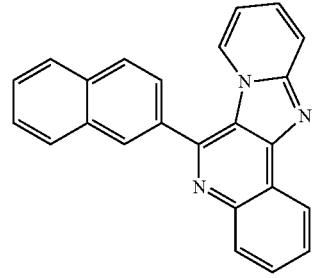

3

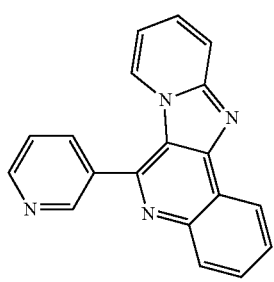

18

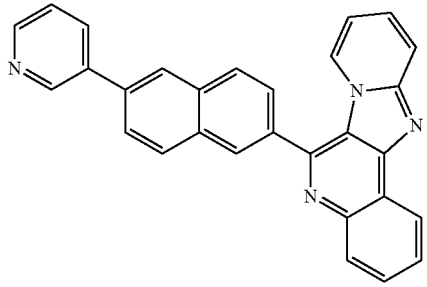

19

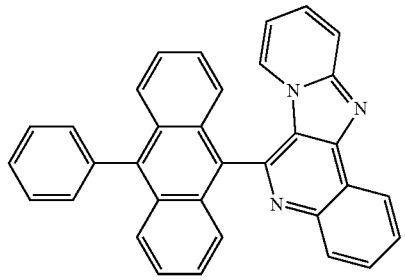

20

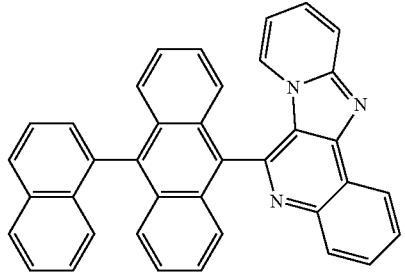

21

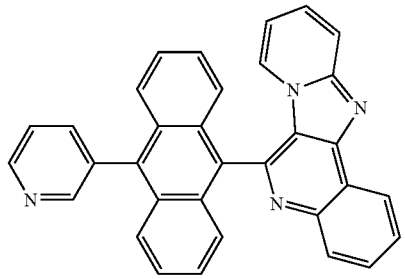

22

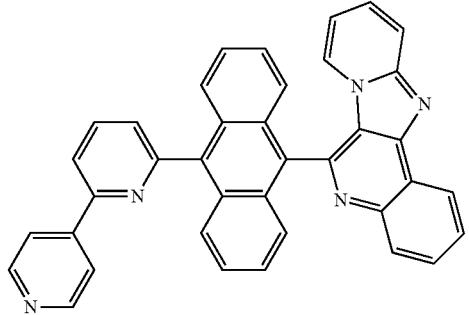

111
-continued
23
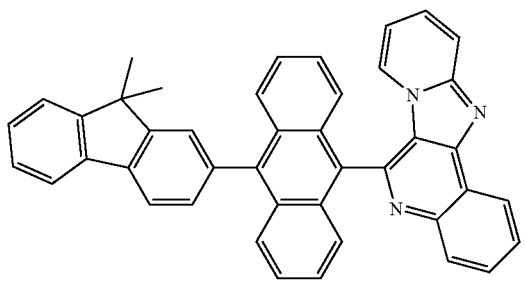
24
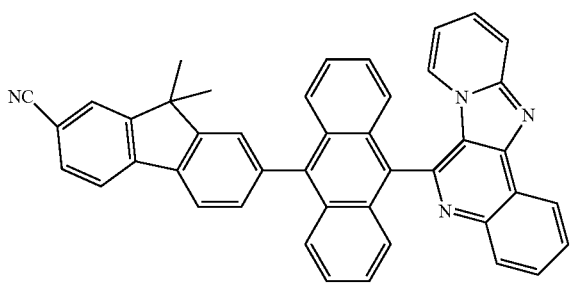
25
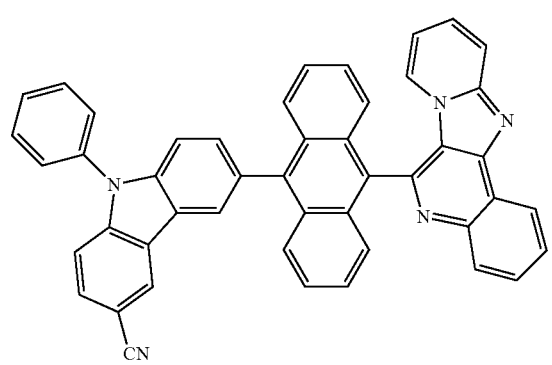
26
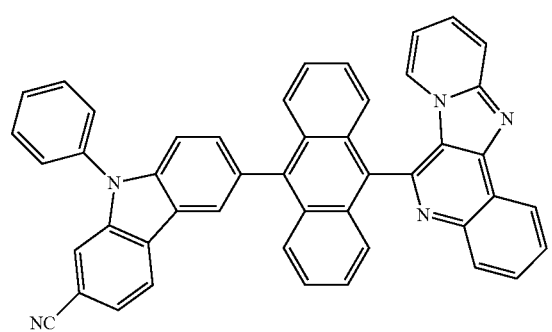
27
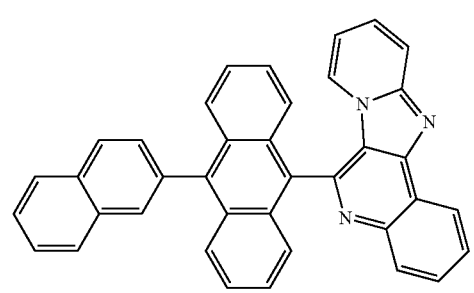
112
-continued
28
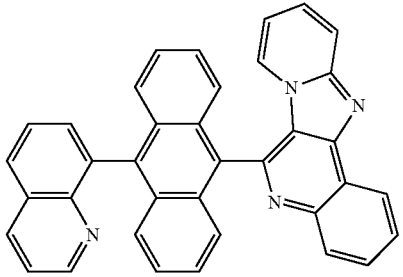
29
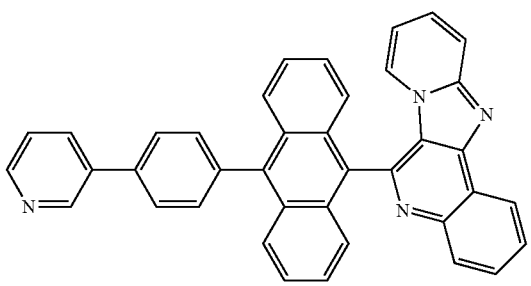
30
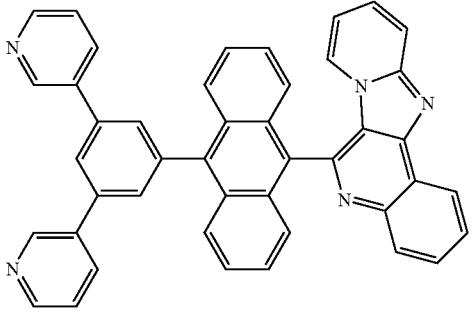
31
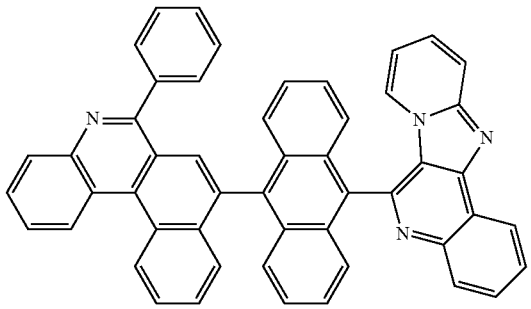
32
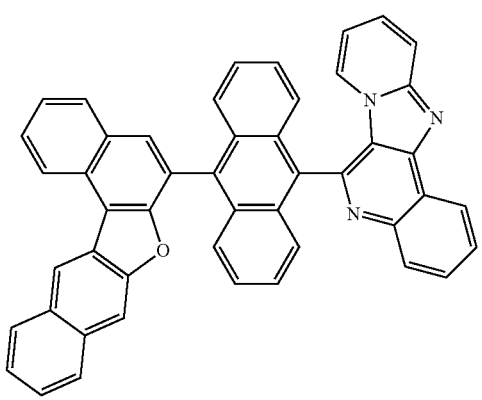

-continued

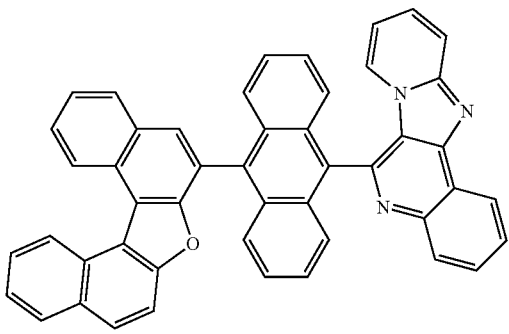

33

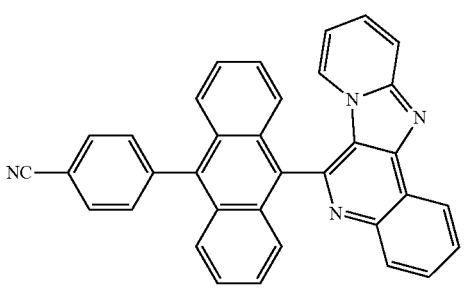

34

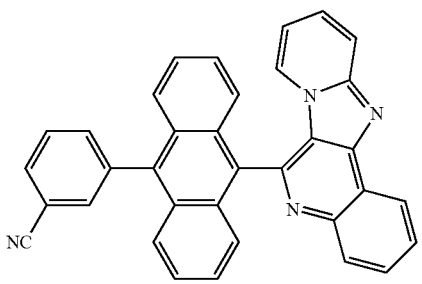

35

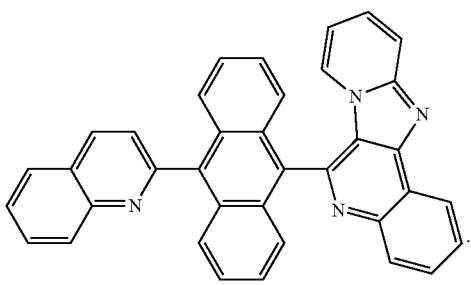

36

6. An organic light-emitting device comprising:
a first electrode;
a second electrode facing the first electrode; and
an organic layer between the first electrode and the second electrode, the organic layer comprising an emission layer,
wherein the organic layer comprises the compound of claim 1.

7. The organic light-emitting device of claim 6, wherein:
the first electrode is an anode,
the second electrode is a cathode, and
the organic layer further comprises:
i) a hole transport region between the first electrode and the emission layer, the hole transport region comprising at least one selected from a hole transport layer, a hole injection layer, and an electron blocking layer, and
ii) an electron transport region between the emission layer and the second electrode, the electron transport region comprising an electron transport layer and at least one selected from a hole blocking layer and an electron injection layer.

8. The organic light-emitting device of claim 7, wherein the electron transport region comprises the compound represented by Formula 1.

9. The organic light-emitting device of claim 7, wherein the electron transport layer comprises the compound represented by Formula 1.

10. The organic light-emitting device of claim 7, wherein the hole transport region comprises a charge-generating material.

11. The organic light-emitting device of claim 10, wherein the charge-generating material is a p-dopant.

12. The organic light-emitting device of claim 10, wherein the charge-generating material is selected from HT-D1 and F4-TCNQ:

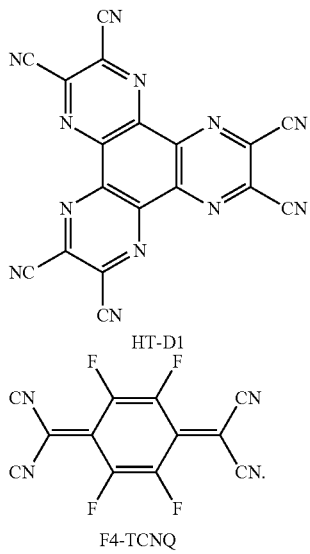

HT-D1

F4-TCNQ

13. The organic light-emitting device of claim 7, wherein the electron transport region comprises a metal-containing material.

14. The organic light-emitting device of claim 7, wherein the electron transport region comprises a Li complex.

15. The organic light-emitting device of claim 7, wherein the electron transport region comprises ET-D1 and/or ET-D2:

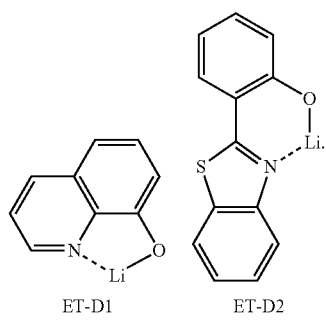

ET-D1          ET-D2

16. A display apparatus comprising the organic light-emitting device of claim 6, wherein the first electrode of the organic light-emitting device is electrically connected to a source electrode or a drain electrode of a thin film transistor.

17. A compound represented by Formula 3 or Formula 4:

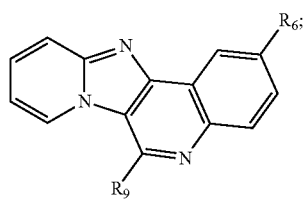

Formula 3

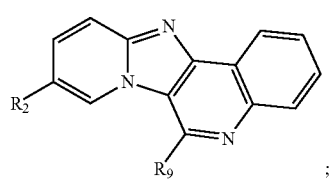

Formula 4 wherein $R_6$ is represented by one selected from Formulae 3a to 3g:

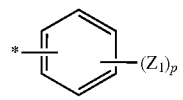

3a

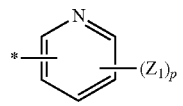

3b

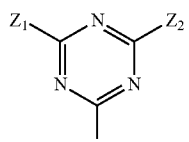

3c

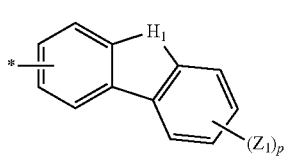

3d

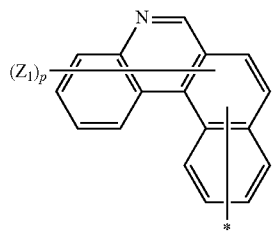

3e

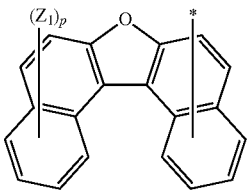

3f

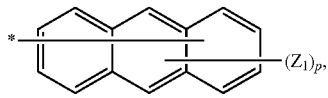

3g wherein, in Formulae 3a to 3g,
  $H_1$ is selected from $CR_{11}R_{12}$, $NR_{13}$, O, and S,
  $R_{11}$ to $R_{13}$, $Z_1$, and $Z_2$ are each independently selected from hydrogen, deuterium, a halogen atom, a cyano group, a nitro group, a hydroxyl group, a carboxyl group, a substituted or unsubstituted $C_1$-$C_{20}$ alkyl group, a substituted or unsubstituted $C_{6-20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group;
  when the number of $Z_1$ groups is 2 or more, a plurality of $Z_1$ groups are identical to or different from each other;
  p is an integer selected from 1 to 9; and
  * indicates a binding site; and
wherein $R_2$ in Formula 4 and $R_9$ in Formulae 3 and 4 are each independently represented by one selected from Formulae 2a to 2e:

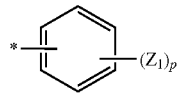

2a

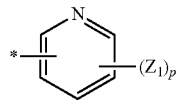

2b

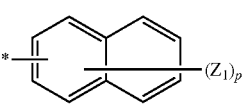

2c

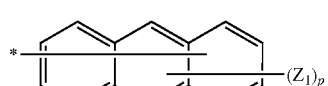

2d

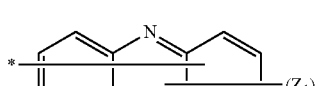

2e wherein, in Formulae 2a to 2e,
  $Z_1$ is selected from hydrogen, deuterium, a halogen atom, a cyano group, a nitro group, a hydroxyl group, a carboxyl group, a substituted or unsubstituted $C_1$-$C_{20}$ alkyl group, a substituted or unsubstituted $C_6$-$C_{20}$ aryl group, a substituted or unsubstituted C$_1$-C$_{20}$ heteroaryl group, a substituted or unsubstituted monovalent non-aromatic condensed polycyclic group, and a substituted or unsubstituted monovalent non-aromatic condensed heteropolycyclic group;

when the number of Z$_1$ groups is 2 or more, a plurality of Z$_1$ groups are identical to or different from each other;

p is an integer selected from 1 to 9; and

* indicates a binding site.

18. The compound of claim 13, wherein the compound represented by Formula 3 or 4 is represented by one selected from Compounds 37 to 90:

37

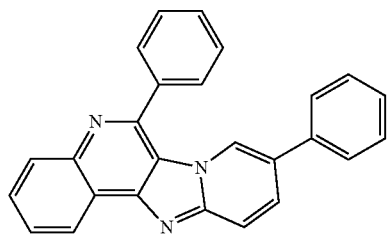

38

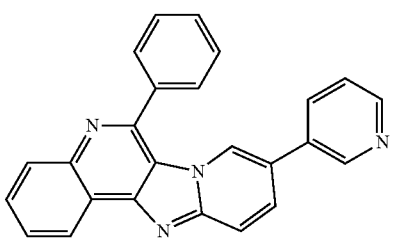

39

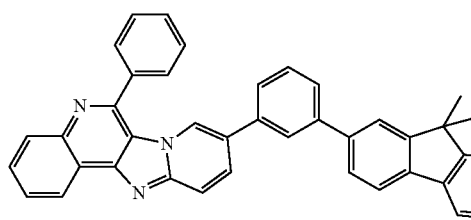

40

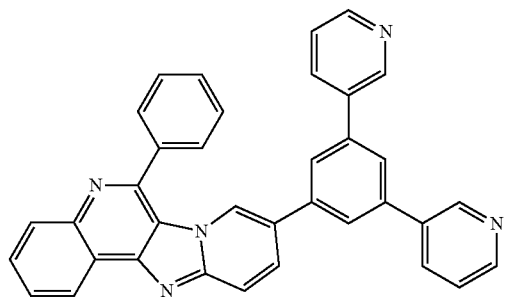

-continued

41

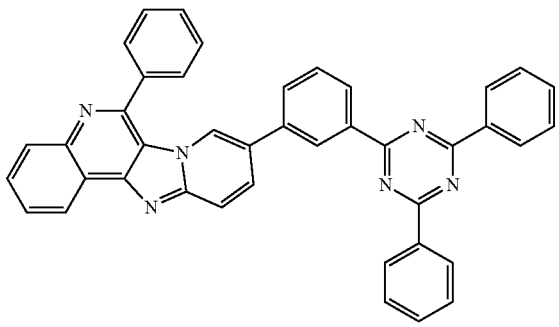

42

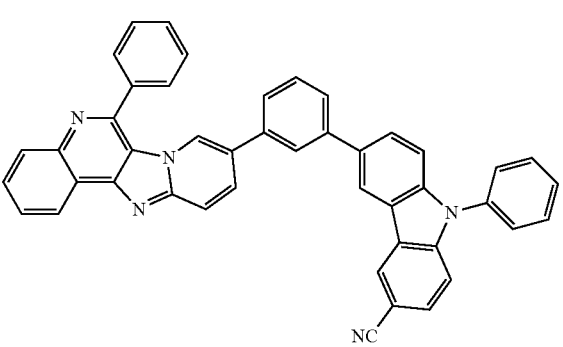

43

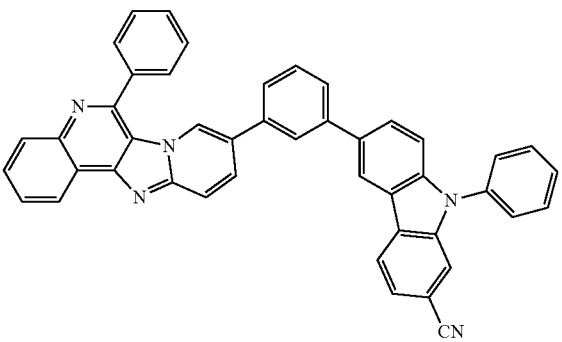

44

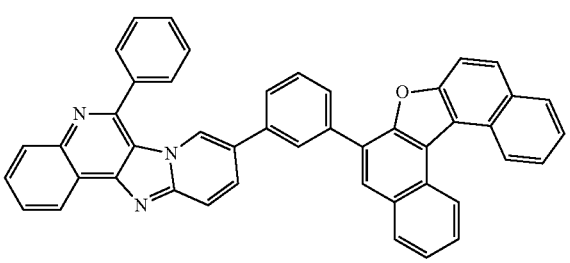

45

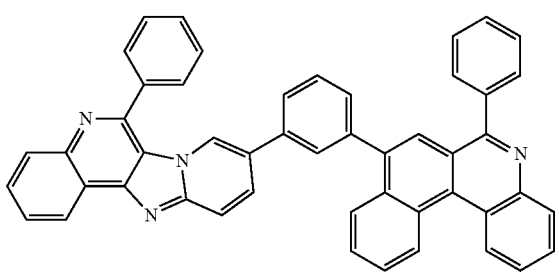

119
-continued
46
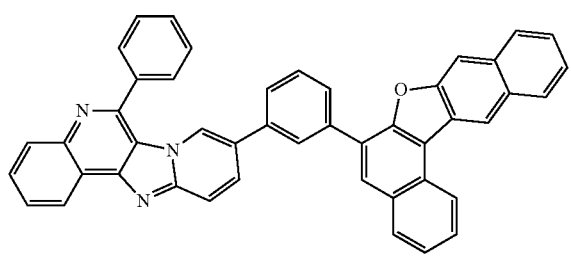
47
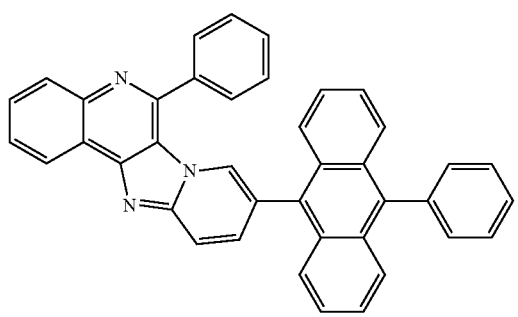
48
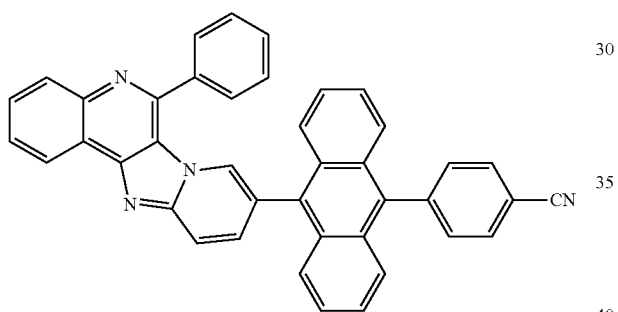
49
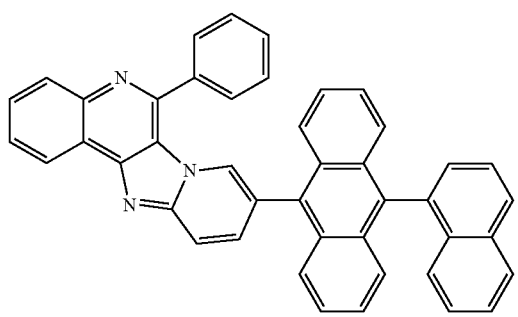
50
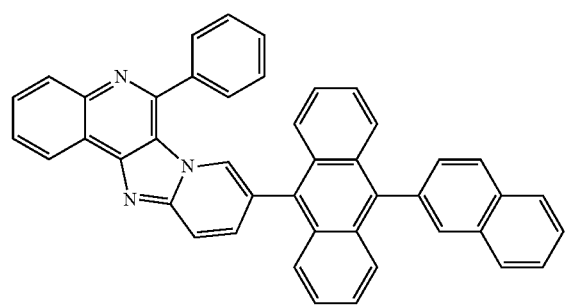
120
-continued
51
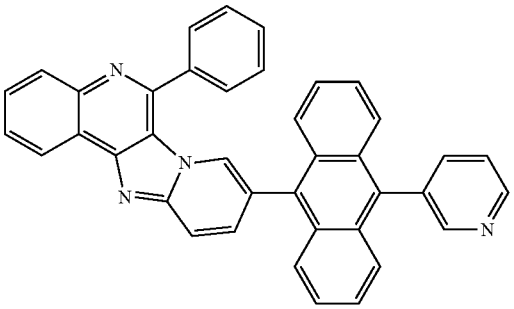
52
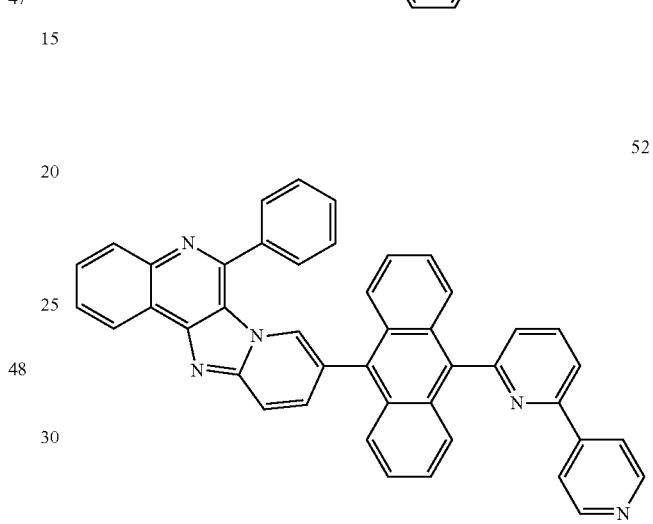
53
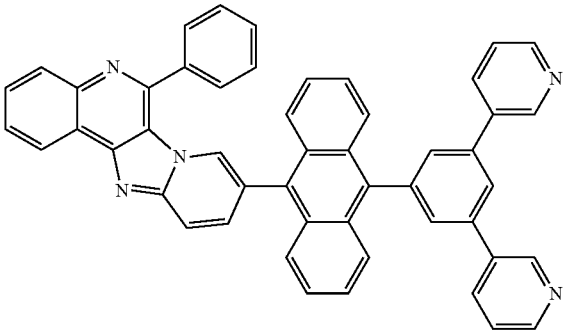
54
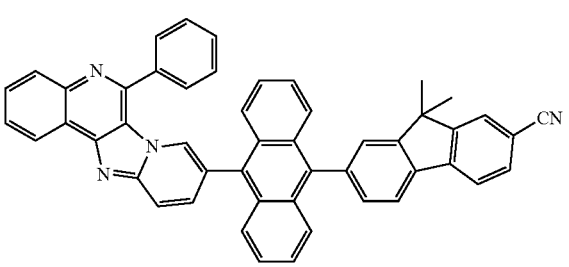

121
-continued
55
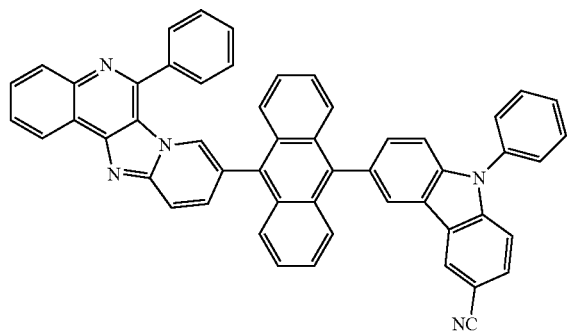
56
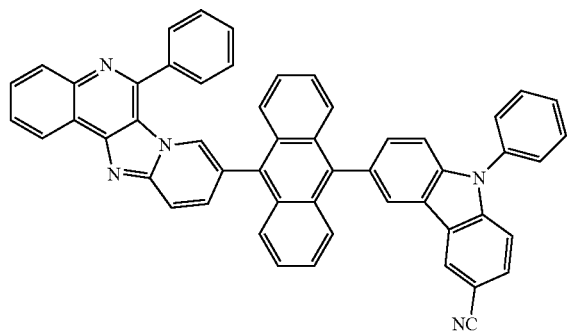
57
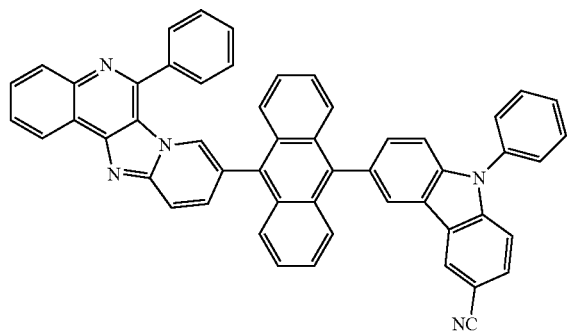
58
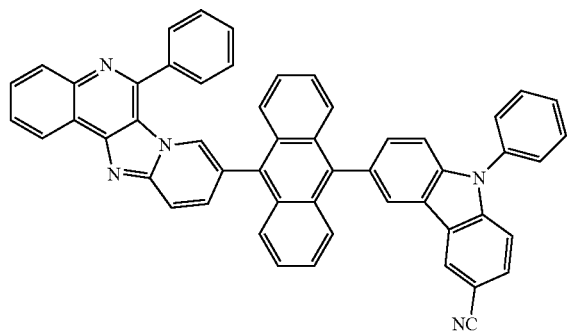
122
-continued
59
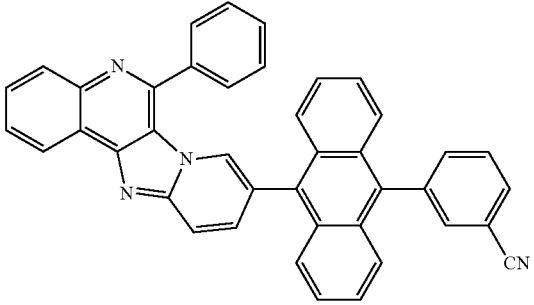
60
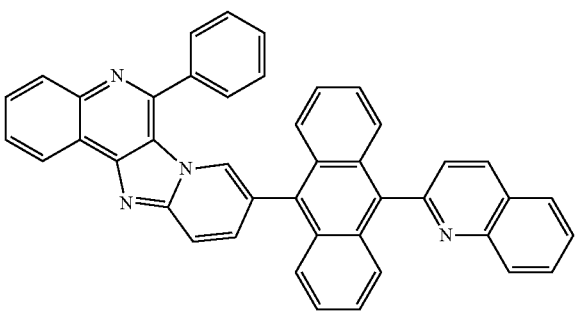
61
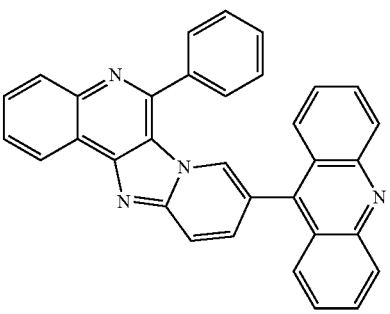
62
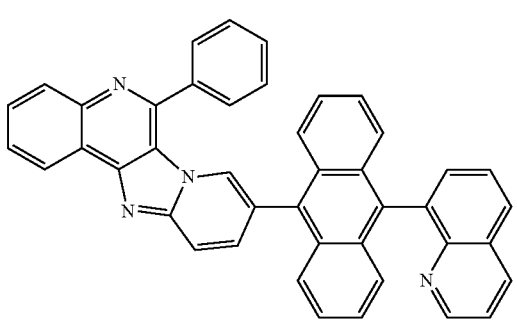
63
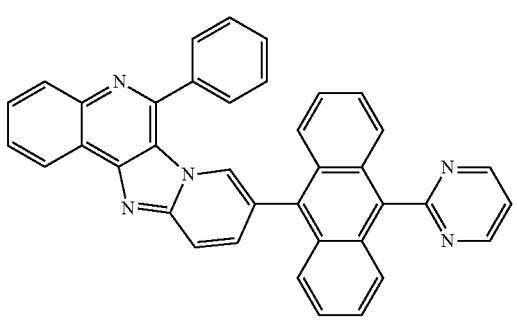

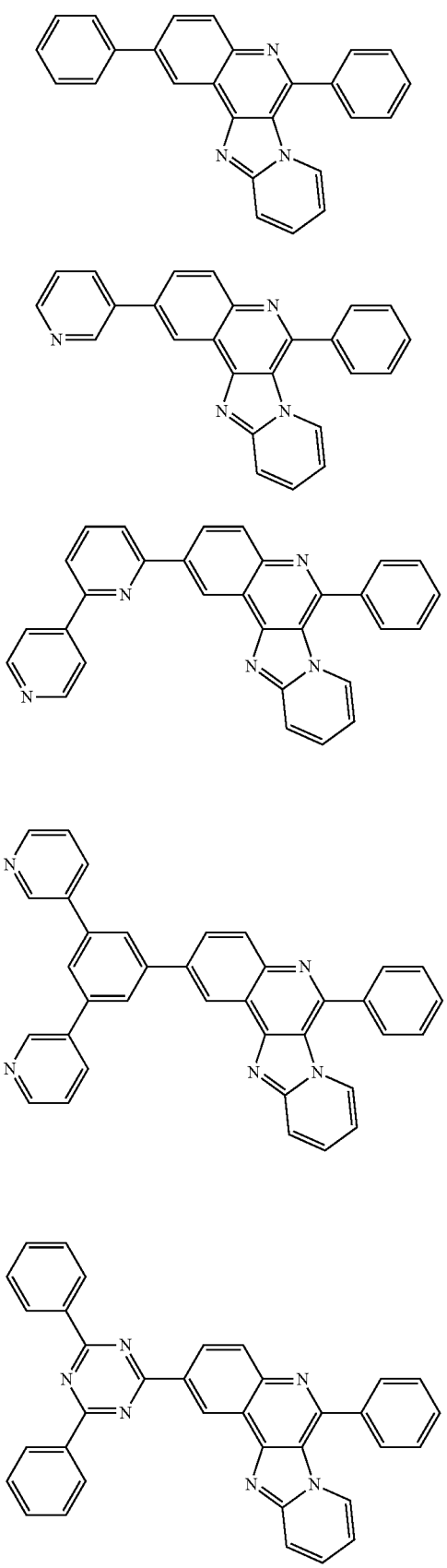
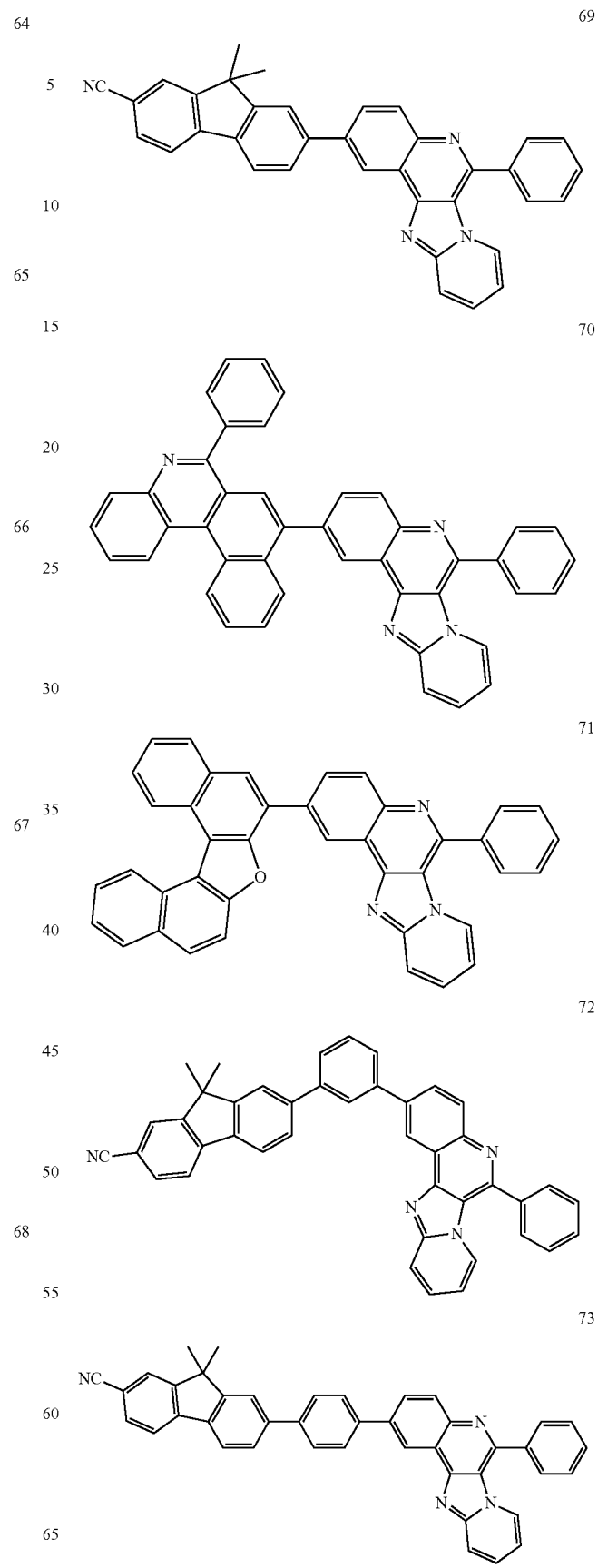

74
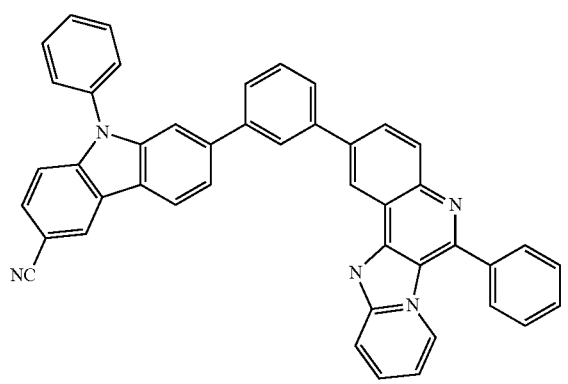
75
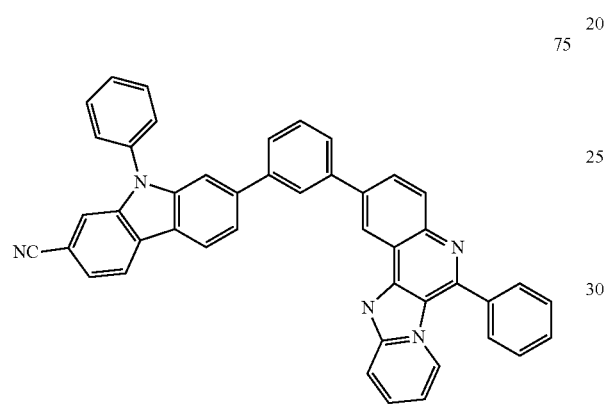
76
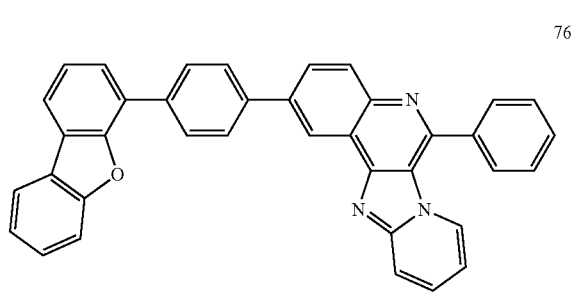
77
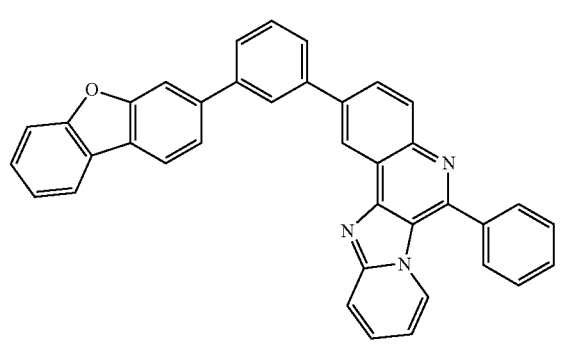
78
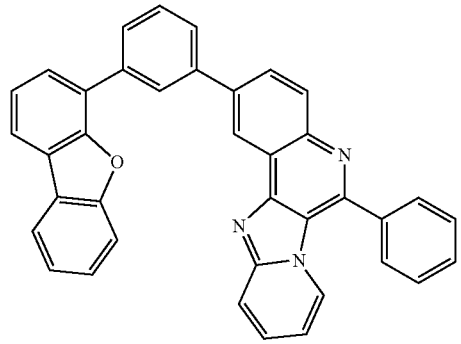
79
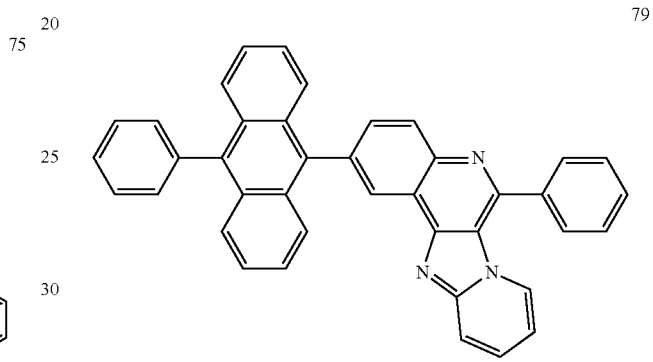
80
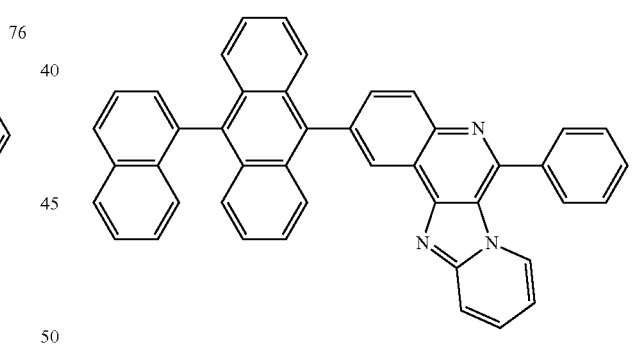
81
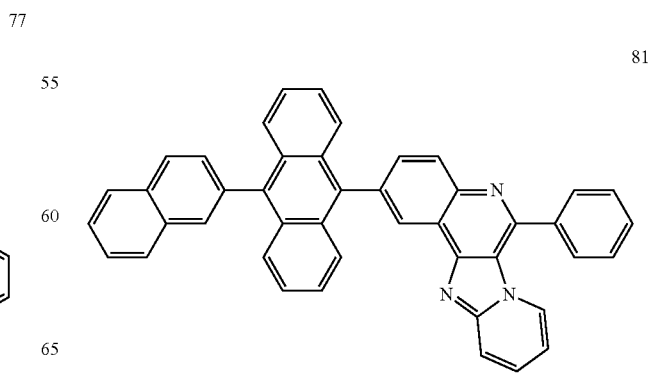

82
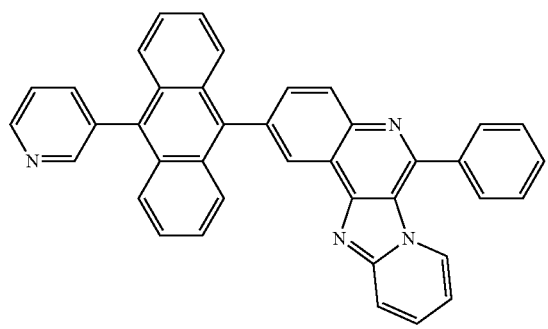
83
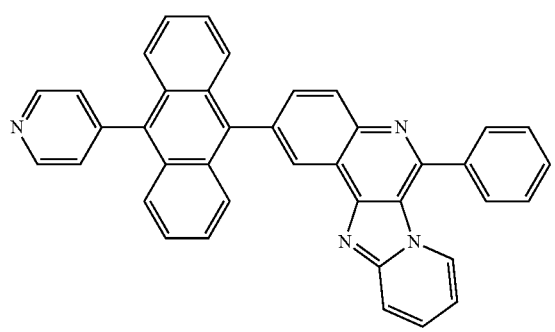
84
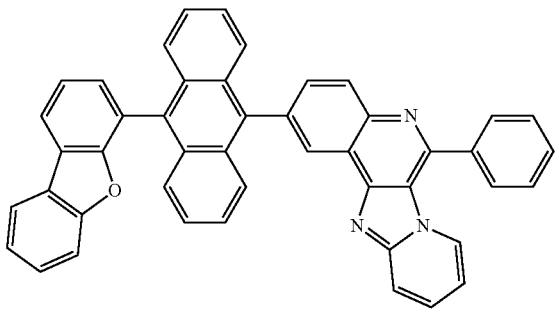
85
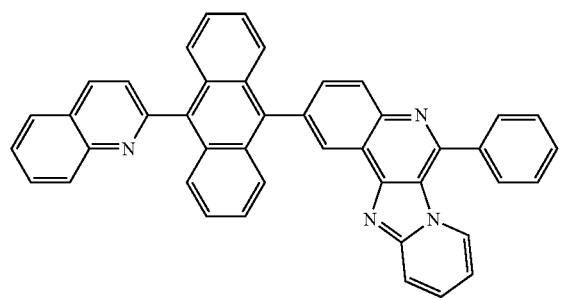
86
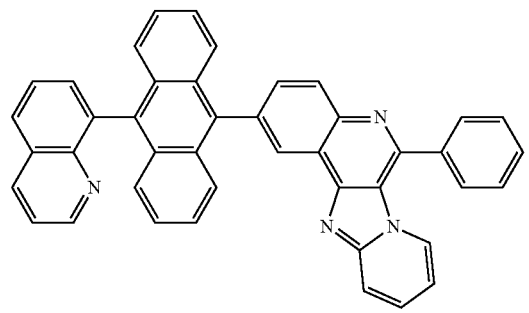
87
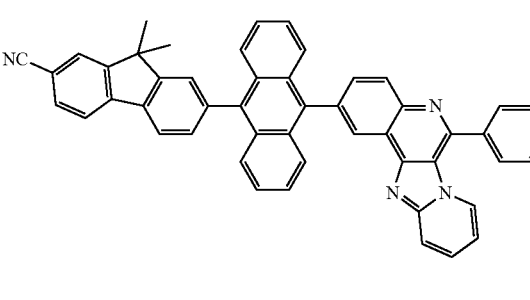
88
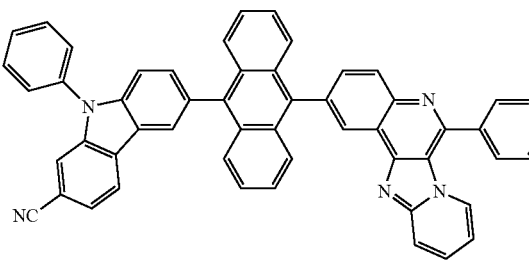
89
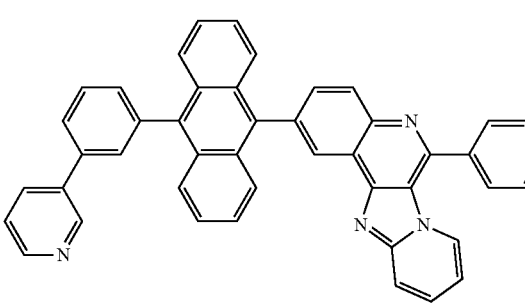
90
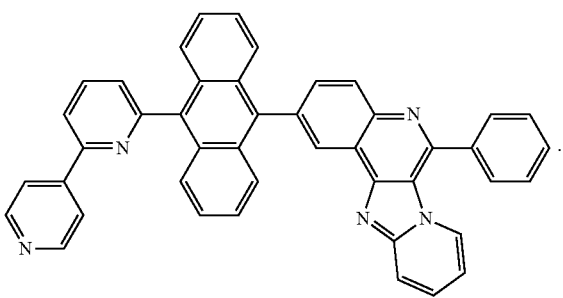
* * * * *